(12) United States Patent
Noelle et al.

(10) Patent No.: US 8,501,915 B2
(45) Date of Patent: Aug. 6, 2013

(54) REGULATORY T CELL MEDIATOR PROTEINS AND USES THEREOF

(75) Inventors: Randolph J. Noelle, Plainfield, NH (US); Li Wang, Norwich, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/546,098

(22) Filed: Jul. 11, 2012

(65) Prior Publication Data

US 2012/0301484 A1 Nov. 29, 2012

Related U.S. Application Data

(60) Division of application No. 12/732,371, filed on Mar. 26, 2010, now Pat. No. 8,231,872, which is a continuation-in-part of application No. 11/912,397, filed as application No. PCT/US2006/015239 on Apr. 24, 2006, now Pat. No. 8,236,304.

(60) Provisional application No. 60/674,567, filed on Apr. 25, 2005.

(51) Int. Cl.
*C07K 16/00* (2006.01)

(52) U.S. Cl.
USPC ...................................................... 530/387.1

(58) Field of Classification Search
None
See application file for complete search history.

(56) References Cited

U.S. PATENT DOCUMENTS

| | | | |
|---|---|---|---|
| 6,924,355 B2 | 8/2005 | Baker et al. | |
| 6,936,436 B2 | 8/2005 | Baker et al. | |
| 6,936,697 B2 | 8/2005 | Desnoyers et al. | |
| 7,026,448 B2 | 4/2006 | Baker et al. | |
| 7,655,778 B2 | 2/2010 | Yang | |
| 2003/0054406 A1 | 3/2003 | Baker et al. | |
| 2008/0248007 A1 | 10/2008 | Chen | |
| 2008/0287358 A1 | 11/2008 | Noelle et al. | |
| 2011/0027278 A1 | 2/2011 | Noelle et al. | |
| 2011/0245468 A1* | 10/2011 | Chen | 530/387.2 |

FOREIGN PATENT DOCUMENTS

WO 2011/120013 9/2011

OTHER PUBLICATIONS

Sequence alignment, 2012, 1 page.*
NCBI Accession No. XI_233720 [gi:109475938] with Revision History—Jan. 13, 2003-Jun. 22, 2006.
Lederman et al.; Molecular Immunology,1991, 28: 1171-1181.
Sequence Alignment, 2010, 1 page.
NCBI Accession No. NM_028732 [gi:31980769] with Revision History—Mar. 20, 2001-May 7, 2006. 143249860 which replaced 31980768 is provided.
NCBI Accession No. NP_080401 [gi:13385632] with Revision History—Mar. 20, 2001-May 7, 2006.
NCBI Accession No. NM_022153 [gi: 62339431] with Revision History—Apr. 7, 2005-Jun. 26, 2007.
NCBI Accession No. NP_071436 [gi: 62339432] with Revision History—Apr. 7, 2005-Aug. 13, 2006.
NCBI Accession No. NM_138530 [gi:51491892] with Revision History—Apr. 4, 2002-Nov. 18, 2006.
NCBI Accession No. AK004116 [gi:12835174] with Revision History—Feb. 8, 2011-Sep. 2, 2005.
NCBI Accession No. NM_026125 [gi:13385631] with Revision History—Mar. 20, 2001-May 7, 2006. 142365660 which replaced 13385631 is provided.
NCBI Accession No. BC089443 [gi:59807840] with Revision History—Feb. 15, 2005-Jun. 6, 2006.
NCBI Accession No. AAH89443 [gi:59807841] with Revision History—Feb. 15, 2005-Jun. 6, 2006.
Di Maro et al., Isolation and characterization of four typ-1 ribosome-inactivating proteins, with polynucleotide:adenosine glycosidase activity, from leaves of *Phytolacca dioica*L., Planta 1999; 208: 125-131.
Boon et al., Human T Cell Responses Against Melanoma, Annu. Rev. Immunol., 2006, 24: 175-208.
Nielsen et al., Melanoma vaccines: the paradox of T cell activation without clinical response, 2000, Cancer Chemother, Pharmacol., 46 (Suppl.): S62-S66.
Lae et al., Increased Vaccine-Specific T Cell Frequency After Peptide-Based Vaccination Correlates with Increased Susceptibility to In Vitro Stimulation But Does Not Lead to Tumor Regression., 1999, J. Immunol., 163: 6292-6300.
GenBank Accession No. NP_083008 (Mar. 3, 3010) platelet receptor Gi24 isoform 1 precursor [*Mus musculus*].
GenBank Accession No. NP_071436 (Sep. 3, 2009), platelet receptor Gi24 precursor [*Homo spaiens*].
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Wang, L. et al., VISTA, a novel mouse Ig superfamily ligand that negatively regulates T cell response. J. Exp. Med. Mar. 7, 2011, vol. 208. No. 3, pp. 577-592.

* cited by examiner

*Primary Examiner* — Ilia Ouspenski
(74) *Attorney, Agent, or Firm* — Hunton & Williams LLP

(57) ABSTRACT

The present invention relates to novel regulatory T cell proteins. One protein, designated PD-L3, resembles members of the PD-L1 family, and co-stimulates αCD3 proliferation of T cells in vitro. A second, TNF-like, protein has also been identified as being upregulated upon αCD3/αGITR stimulation. This protein has been designated $T^{reg}$-sTNF. Proteins, antibodies, activated T cells and methods for using the same are disclosed.

Figure 1D:
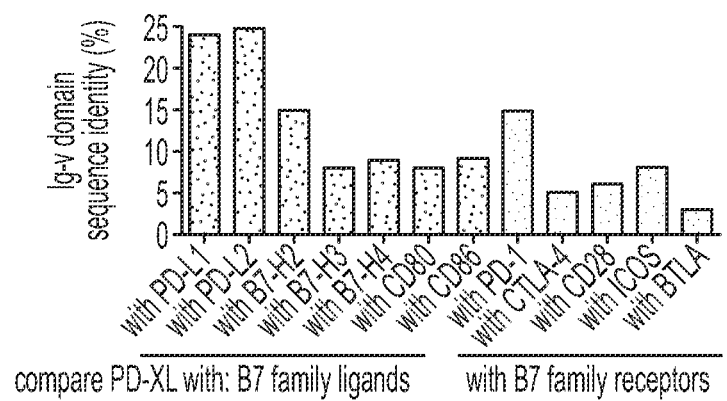

In particular methods of using these proteins and compounds, preferably antibodies, which bind or modulate (agonize or antagonize) the activity of these proteins, as immune modulators and for the treatment of cancer, autoimmune disease, allergy, infection and inflammatory conditions, e.g. multiple sclerosis is disclosed.

8 Claims, 25 Drawing Sheets

A. Full length sequence of murine PD-XL

```
MGVPAVPEASSPRWGTLLLAIFLAASRGLVAAFKVTTPYSLYVCPEGQNA     50
TLTCRILGPVSKGHDVTIYKTWYLSSRGEVQMCKEHRPIRNFTLQHLQHH    100
GSHLKANASHDQPQKHGLELASDHHGNFSITLRNVTPRDSGLYCCLVIEL    150
KNHHPEQRFYGSMELQVQAGKGSGSTCMASNEQDSDSITAAALATGACIV    200
GILCLPLILLLVYKQRQVASHRRAQELVRMDSSNTQGIENPGFETTPPFQ    250
GMPEAKTRPPLSYVAQRQPSESGRYLLSDPSTPLSPPGPGDVFFPSLDPV    300
PDSPNSEAI*
```

FIG. 1A

B. Alignment of extracellular domains of murine PD-XL with B7-H1 (PD-L1), B7-DC (PD-L2), B7-H3, and B7S1.

```
PD-XL         ----FKVITPYSLYVC------PEGQNATILCRILGPVSKGHDVTIYKWYLSSRGEVQM
B7-H1_(PD-L1) ----FTITAPKDLYVV------EYGSNVTMECRF--PVERELDLLALVVYWEKE-DEQ--
B7-DC_(PD-L2) L---FIVTAPKEVYTV------DVGSSVSLECDF---------------------DRRE
B7-H3_(CD276) ----VEVQVSEDPVVA------LVDTDATLRCSF--SPEPGFSLAQLNLIWQLT-DTKQL
B7-H4_(B7S1)  LIIGEGISGKHFITVTTFTSAGNIGEDGTISCTF----EPDIKLNGIVIQWLKE-GIKGL

PD-XL         CKEHRPIRN-FTLQHLQHHGSHLKANASHDQPQKHGLELASDHHGNFSITLRNVTPRSSG
B7-H1_(PD-L1) VIQFVAGEEDLKPQHSNFRG---RASLPKDQLLK----------GNAALQITDVKLQDAG
B7-DC_(PD-L2) CTELEGIRASLQKVENDTSLQSERATLLEEQLPL----------GKALFHIPSVQVRDSG
B7-H3_(CD276) VHSFTEGRD----QGSAYSN---RTALFPDLLVQ----------GNASLRLQPVRYTDEG
B7-H4_(B7S1)  VHEFKEGKDDLSQQHEMFRG---RTAVFADQVVV----------GNASLRLKNVQLTDAG

PD-XL         LYCCLV---------IELKNHHPEQRF-------YGSMELQVQAGKG-----
B7-H1_(PD-L1) VYRCMISYGGA-DYKRITLKVNAPYRKINQRISVDPA-----ISEHELICQA-EGYPEAE
B7-DC_(PD-L2) QYRCLVICGAAWDYKYLTVKVKASYMRIDTRILEVPG-----IGEVQLTCQA-RGYPLAE
B7-H3_(CD276) SYTCFVSIQDF-DSAAVSLQVAAPYSK--PSMTLEPNKDLRPGNMVTITCSSYQGYPEAE
B7-H4_(B7S1)  TYTCYIRTSKGKGNANLEYKTGAFSM---PEINVDYN------ASSESLRCEAPRWFPQPT

PD-XL         -------------SGST------------------------MASNEQDSDSITA
B7-H1_(PD-L1) VIWTN--SDHQPVSGKRSVTTSRTEGMLLNVTSSLRVNATANDVFYCTFWRSQPGQNHTA
B7-DC_(PD-L2) VSWQN-------VSVPANTSHIRTPEGLYQVTSVLRLKPQRSRNFSCMFWNAHMKELTSA
B7-H3_(CD276) VFWKD--GQGVPLTGNVTTSQMANERGLFDVHSVLRVVLGANGTYSCLVRNPVLQQDAHG
B7-H4_(B7S1)  VAWASQVDQGANFSEVSNTSFELNSENVTMKVVSVLTNVTINNTYSCMIENDIAK--ATG

PD-XL         A----------------
B7-H1_(PD-L1) ELIIPELPATHPPQNRTH---
B7-DC_(PD-L2) IIDPLSRMEPKVPRTW-----
B7-H3_(CD276) SVTITGQPLTFPPEA------
B7-H4_(B7S1)  DIKVTDSEVKRRSQLQLLNSG
```

FIG. 1B

C. Alignment of extracellular domains of murine PD-XL with
receptors PD-1, CTLA-4, CD28, BTLA, and ICOS.

```
PD-XL   ---FKVTTPY----------SLYVCPEGQNATLTCRILGPVSKGHDVTIYKTWYLSSRGE
PD-1    -SGWLLEVPNGPWRSLTFYPAWLTVSEGANATFTCSLS----------------NWSEDLM
CTLA-4  -EAIQVTQPS----------VVLASSHG-VASFPCEYS----------------PSHNTDE
CD28    ------------------------------RSNAEFNCD---------------------
BTLA    EKATKRNDEECPVQLTITRNSKQSARTGELFKIQCPVK----------------YCVHRPN
ICOS    --EINGSADH----------RMFSFHNG-GVQISCKYP----------------ETVQQLK

PD-XL   VQMCKEHRPIR---NFTLQHLQHHGSHLKANASHDQPQKHGLELASDHHGNFSITLRNVT
PD-1    LNWNRLSPSNQ-------TEKQAAFCNGLSQPVQDARFQIIQLPN----RHDFHMNILDTR
CTLA-4  VRVTVLRQTND---QMTEVCATTFTEKNTVGFLDYPFCSGTFNE-----SRVNLTIQGLR
CD28    ------------------------------------GDFDN-----ETVTFRLWNLH
BTLA    VTWCKHNGTICVPLEVSPQLYTSWEENQSVPVFVLHFKPIHLSDNGSYSCSTNFNSQVIN
ICOS    MRLFREREVLC---ELT----KTKGSGNAVSIKNPMLCLYHLSN-----NSVSFFLNNPD

PD-XL   PRDSGLYCCLVIELKNHHPEQRFYGSMELQVQAGKGSGSTCMASNEQDSDSITAA-----
PD-1    RNDSGIYLC---GAISLHPKAKIEES----------PGAELVVTERILETSTRYPSPSPK
CTLA-4  AVDTGLYLC---KVELMYPPPYFVGM--------GNGTQIYVIDPEPCPDSD-------
CD28    VNHTDIYFC---KIEFMYPPPYLDNE--------RSNGTIIHIKEKHLCHTQSSPKL---
BTLA    SHSVTIHVRERTQNSSEHPLITVSDI----------PDATNASGPSTMEERPGRTWLLY--
ICOS    SSQGSYYFC---SLSIFDPPPFQERN----------LSGGYLHIYESQLCCQLKLWL----

PD-XL   ---------
PD-1    PEGRFQGM
CTLA-4  --------
CD28    --------
BTLA    --------
ICOS    --------
```

FIG. 1C

FIG. 1E

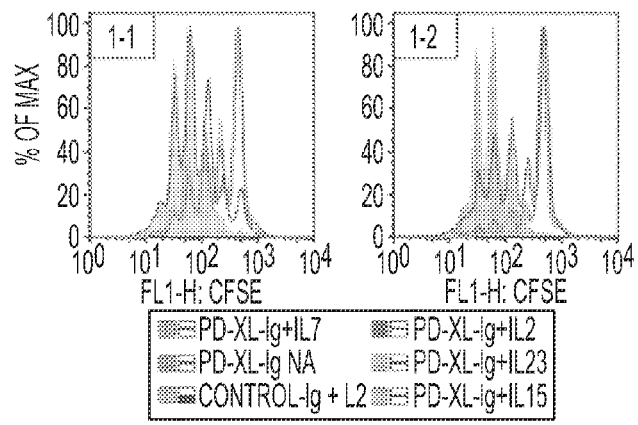
FIG. 14A
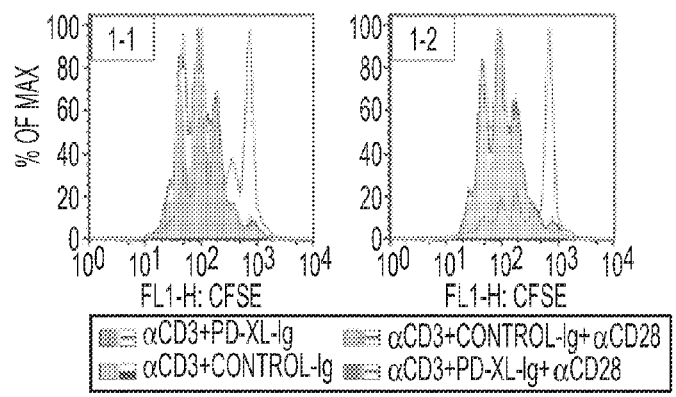
FIG. 14B
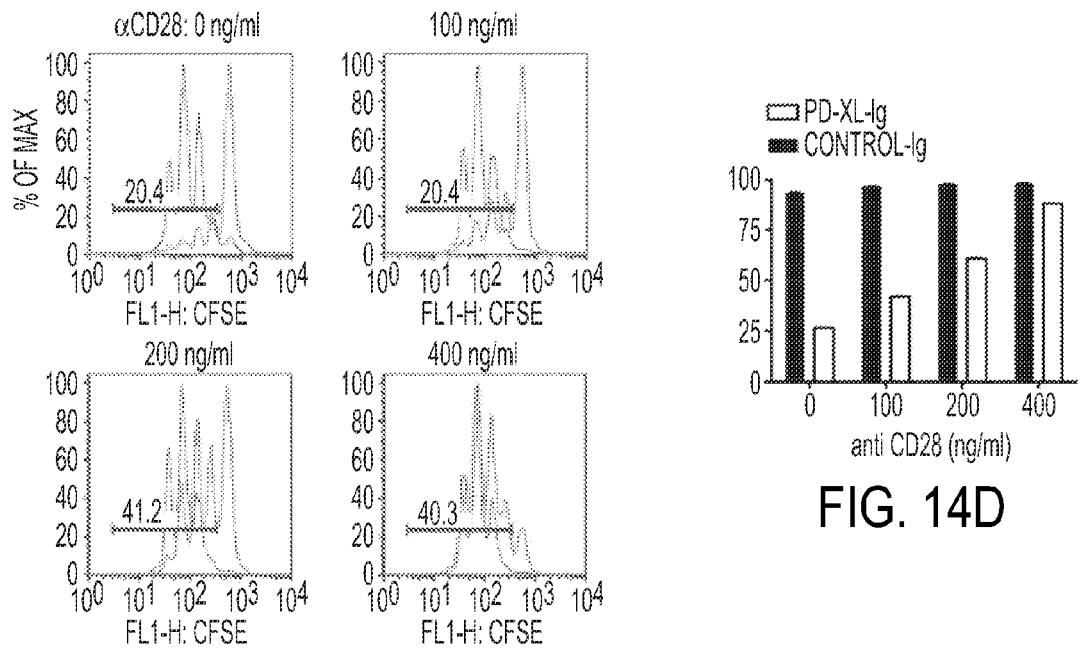
FIG. 14C
FIG. 14D

SEQUENCE LISTING

```
<160> NUMBER OF SEQ ID NOS: 10

<210> SEQ ID NO 1
<211> LENGTH: 4795
<212> TYPE: DNA
<213> ORGANISM: Mus musculus

<400> SEQUENCE: 1
gagcattcac tctagcgagc gagcggcgtg tacagccggc tccctgggct cctggagtcc      60
cgcttgctcc aagcgcactc cagcagtctc tttctgctct tgcccggctc gacggcgaca     120
tgggtgtccc cgcggtccca gaggccagca gcccgcgctg gggaaccctg ctccttgcta     180
ttttcctggc tgcatccaga ggtctggtag cagccttcaa ggtcaccact ccatattctc     240
tctatgtgtg tcccgaggga cagaatgcca ccctcacctg caggattctg ggccccgtgt     300
ccaaagggca cgatgtgacc atctacaaga cgtggtacct cagctcacga ggcgaggtcc     360
agatgtgcaa agaacaccgg cccatacgca acttcacatt gcagcacctt cagcaccacg     420
gaagccacct gaaagccaac gccagccatg accagcccca gaagcatggg ctagagctag     480
cttctgacca ccacggtaac ttctctatca ccctgcgcaa tgtgacccca agggacagcg     540
gcctctactg ctgtctagtg atagaattaa aaaaccacca cccagaacaa cggttctacg     600
ggtccatgga gctacaggta caggcaggca aaggctcggg gtccacatgc atggcgtcta     660
atgagcagga cagtgacagc atcacggctg cggccctggc caccggcgcc tgcatcgtgg     720
gaatcctctg cctcccccctt atcctgctgc tggtctataa gcagagacag gtggcctctc     780
accgccgtgc ccaggagttg gtgaggatgg acagcagcaa cacccaagga atcgaaaacc     840
caggcttcga gaccactcca cccttccagg ggatgcctga ggccaagacc aggccgccac     900
tgtcctatgt ggcccagcgg caaccttcgg agtcaggacg gtacctgctc tctgacccca     960
gcacacctct gtcgcctcca ggccctgggg acgtcttttt cccatcccta gatccagtcc    1020
ctgactcccc taactctgaa gccatctaaa ccagctgggg aaccatgaac catggtacct    1080
gggtcaggga tatgtgcact tgatctatgg ctggcccttg gacagtcttt taggcactga    1140
ctccagcttc cttgctcctg ctctgagcct agactctgct tttacaagat gcacagaccc    1200
tcccctatct ctttcagacg ctacttgggg ggcagggaga agatgttgga ttgctcattg    1260
ctgttctcaa gatcttggga tgctgagttc tccctagaga cttgacttcg acagccacag    1320
atgtcagatg acctgcatcc tatgaacgtc cggcttggca agagcctttc ttcatggaaa    1380
ccagtagccc ggaggggatg aggtaggcac cttgccaccc tcccgggaga gagacacaag    1440
atgtgagaga ctcctgctca ctgtgggggt gtggctggcc tgcttgtttg cctgaggatg    1500
```

```
ctcctctgtt ggactgactc tatcccctg gattctggag cttggctggc ctatgtccca    1560
ccagaggagc atctcagcag ccttccacca gcaacctgag ggcctgccag cttcgtggct    1620
ctgggctctc attacctgta tggccgtcca cagagctcag tggccagagg ctttgaaaca    1680
ggaagtacat gtcaggttca ggaaccactg tgagctcatt agtgtcttga gcaatgtgag    1740
gcctggacca gtggacacgg agggagggtg gcgagaggat gatgggatg atgaggggaa     1800 cacgctccct tcctgtcctt gtcatccacc actaccacta ttcagtgtgg agcagtggca    1860
aaggtgaccg acctccacaa tgtcctagtg atgctggacc atttctaagt gtgaaagaga    1920
tgctattaaa aacagtatgt ggcaatggct gccaacagct gagtggactg gaggcactgg    1980
ctttaaggcc ctggaggtgc agggcccggt atggggatag ggatgggagt ttcagtgagg    2040
gcctagggat cactccgctt ctgaccactc ttcttctgag cctcacctca gggtgacctt    2100
caggcacaca gaagagcttg cccctggtcc gatactactc ttggctctca tctccagggt    2160
ttggcatgac ctgggcacac aggggagtc ttcagaaagg attttaaagc atgaaaagaa     2220
agggtagttc ttgtgaggta gggatgggca gctgatgttt gagagtgagg agggatacgg    2280
ctgggcagat cactctccag tctctagagg gaaagtagct ctaagtctgg gagagcagca    2340
gcccagtggt accatatgtc ttcttgcagc ttccactggc tgggctgaac tgggcatggg    2400
taggaaagct cctgttctgg gcctgcagcc agggagaacc ccattcattc cctgaggaca    2460
gatgggtggg gagagaagag agagtttcag gccgggaagc agcaataagc tatctgctgg    2520
ggacccagac aagttgtctg atgaggtcca agatgtggga tgccagttat acctggggct    2580
tggggatcct tagaggcttt gtatcatcat cataggagtg tcgggtggc cagggcatca     2640 aagccatgac ccctgttta tcctcagggt ccactcttct gcaccatcca ttgctctaga    2700
tctatgcagt tactatagac agaatgtgtt gttctgtttg gctttgggga taatggcctg    2760
gcgaactgcc agctgttcag tggcagggct gtgaggccag tcaaagacta gaacccacag    2820
accagctgaa cgatgagtat agcctgtccc ctgggggagc ctgacctgtc tccagcccta    2880
agcttcagac ctcaccactc agatgacttc taagaatttg cctgtgggga ccctgcatg     2940 gctgcagctc cgtggaaagg agaggaggcc cccagcagaa gaaccactcg cttcctgccc    3000
agcttcctcc tgtagggctc taagtctctt cttcttggga ccctgcaagc aaaggcatgt    3060
cagcttggtg gtttcctgtt tgggtgaag ttttgtgtgg tccgggttct gtctacatcc     3120
atgaacttgg ggtgctacca ccttgctgct gctgtagaga cagctgcagg atcttagggt    3180
ggaaaatgga ggtgccctga ggtgctagcc cttgggcaa agatggggt ggcaatgaga      3240 cacagtgggg aactgagttc cccaagagga gggaggagcc ctgtagcctc aagggccata    3300
ttgggttcct ggtaccagca aaagcctaga gagcgaagtc tgtattttga ggaggtaatt    3360
gatccttacg gaatccatca gaaatttgga gcgggtgctt tatctatctc tggagggtct    3420
ctacctatct ccgatgaagc tctccctggg cctgggatgg gagaaaccag gaggaaaggt    3480
gtctgataaa gcagggcttt cttgacaagc caaagggcca ctggtagctg ttgtggaccg    3540
agctgaccct gctgaagtat tgtagtgtgc cttggaccaa cttctcaaaa gagcaacccc    3600
ggggctaccc tacttctgcc aggaagaggc ggagaagggg ctgagaggcc tggaaggggc    3660
tagctccttc tttgagaact gctccccgga ggacttggag gaggcggcta ggctacgggc    3720
tgctgagggc ccttttgtctt tcctaacctg ggcactgtta ggatgctccc tcctggaaaa   3780
ggctttcctg ggtgtgagct agagcagtgt ccatgccagc gctgaacctg ccatggtggg    3840
agctgaacta aaaatttctc agggaactaa aataggcaaa agaggaactg ggggaggagg    3900
```

```
gtgccaggca ggatgggggg aagggagggc agtgcaaaag tctcttgaaa cacagacagc    3960
ccagctgagt gccagtccca gatcacagag aatacggctc atctggctca tgttctgcat    4020
gcttgctgct ttaccctggc actttccttc tccaccatga gtgcgagtcc tgggagtcct    4080
gggagggtga ggattaatgc cagcctgggg agcagatagc tgacagagtc cttgggtaac    4140
tggcttgaac caggacctca ggattccact ctggggatct agctttgtct gggccagtga    4200
agatctctat aatggcatta ttgcaggggg ataaacattt cactgggttc tgatctgttg    4260
ggtgtggctt cctggaaaat atggtgagag gaattctgct aaggatacag ttgataagaa    4320
agttctgaga ttgattagta atgcctgcct tggactcagg aagggaagtg gcagtatgaa    4380
tgccatgtct taatcatttt ggttaaaata tgcttcccaa aagatttcca cgtgtgttct    4440
tgtttatttg acatctgtct ccatatcagt cttgaaagcc tttctgtgtg tatatatatg    4500
atgtttgcgt gtatatatgt ttttgtgtgt gcatatggaa gtcagaaatc actgggtgtc    4560
ttcctccatt cctttgcaat gtatgttttt tttttttta cgatttattt actatatgaa    4620
tgttttgcct gaatacatgc ataggtgtca cgtacatgcc tgctggaacg cttggaactg    4680
gagttacagg tggctatgag ctacagtgtg agcactggga atcaaacctg ggtcttctgc    4740
aagagcaaca aattaaaagt cagctcttaa ctacttgagc tattttttcca actcc         4795
```

<210> SEQ ID NO 2
<211> LENGTH: 309
<212> TYPE: PRT
<213> ORGANISM: Mus musculus

<400> SEQUENCE: 2

```
Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
        195                 200                 205

Leu Leu Leu Val Tyr Lys Gln Arg Gln Val Ala Ser His Arg Arg Ala
    210                 215                 220
```

```
Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
            245                 250                 255

Thr Arg Pro Pro Leu Ser Tyr Val Ala Gln Arg Gln Pro Ser Glu Ser
        260                 265                 270

Gly Arg Tyr Leu Leu Ser Asp Pro Ser Thr Pro Leu Ser Pro Pro Gly
    275                 280                 285

Pro Gly Asp Val Phe Phe Pro Ser Leu Asp Pro Val Pro Asp Ser Pro
290                 295                 300

Asn Ser Glu Ala Ile
305

<210> SEQ ID NO 3
<211> LENGTH: 4774
<212> TYPE: DNA
<213> ORGANISM: Homo sapiens

<400> SEQUENCE: 3
```

| | | | | | |
|---|---|---|---|---|---|
| gggggcgggt | gcctggagca | cggcgctggg | gccgcccgca | gcgctcactc | gctcgcactc | 60 |
| agtcgcggga | ggcttccccg | cgccggccgc | gtcccgcccg | ctccccggca | ccagaagttc | 120 |
| ctctgcgcgt | ccgacggcga | catgggcgtc | ccacggccc | tggaggccgg | cagctggcgc | 180 |
| tggggatccc | tgctcttcgc | tctcttcctg | gctgcgtccc | taggtccggt | ggcagccttc | 240 |
| aaggtcgcca | cgccgtattc | cctgtatgtc | tgtcccgagg | ggcagaacgt | caccctcacc | 300 |
| tgcaggctct | tgggccctgt | ggacaaaggg | cacgatgtga | ccttctacaa | gacgtggtac | 360 |
| cgcagctcga | ggggcgaggt | gcagacctgc | tcagagcgcc | ggcccatccg | caacctcacg | 420 |
| ttccaggacc | ttcacctgca | ccatggaggc | caccaggctg | ccaacaccag | ccacgacctg | 480 |
| gctcagcgcc | acgggctgga | gtcggcctcc | gaccaccatg | gcaacttctc | catcaccatg | 540 |
| cgcaacctga | ccctgctgga | tagcggcctc | tactgctgcc | tggtggtgga | gatcaggcac | 600 |
| caccactcgg | agcacagggt | ccatggtgcc | atggagctgc | aggtgcagac | aggcaaagat | 660 |
| gcaccatcca | actgtgtggt | gtacccatcc | tcctcccagg | atagtgaaaa | catcacggct | 720 |
| gcagccctgg | ctacgggtgc | ctgcatcgta | ggaatcctct | gcctcccct | catcctgctc | 780 |
| ctggtctaca | gcaaaggca | ggcagcctcc | aaccgccgtg | cccaggagct | ggtgcggatg | 840 |
| gacagcaaca | ttcaagggat | tgaaaacccc | ggctttgaag | cctcaccacc | tgcccagggg | 900 |
| atacccgagg | ccaaagtcag | gcaccccctg | tcctatgtgg | cccagcggca | gccttctgag | 960 |
| tctgggcggc | atctgctttc | ggagcccagc | accccctgt | ctcctccagg | ccccggagac | 1020 |
| gtcttcttcc | catccctgga | ccctgtccct | gactctccaa | actttgaggt | catctagccc | 1080 |
| agctggggga | cagtgggctg | ttgtggctgg | gtctgggca | ggtgcatttg | agccagggct | 1140 |
| ggctctgtga | gtggcctcct | tggcctcggc | cctggttccc | tccctcctgc | tctgggctca | 1200 |
| gatactgtga | catcccagaa | gcccagcccc | tcaacccctc | tggatgctac | atgggatgc | 1260 |
| tggacggctc | agcccctgtt | ccaaggattt | tggggtgctg | agattctccc | ctagagacct | 1320 |
| gaaattcacc | agctacagat | gccaaatgac | ttacatctta | agaagtctca | gaacgtccag | 1380 |
| cccttcagca | gctctcgttc | tgagacatga | gccttgggat | gtggcagcat | cagtgggaca | 1440 |
| agatggacac | tgggccaccc | tcccaggcac | cagacacagg | gcacggtgga | gagacttctc | 1500 |
| ccccgtggcc | gccttggctc | cccgttttg | ccgaggctg | ctcttctgtc | agacttcctc | 1560 |
| tttgtaccac | agtggctctg | ggccaggcc | tgcctgccca | ctggccatcg | ccaccttccc | 1620 |

```
cagctgcctc ctaccagcag tttctctgaa gatctgtcaa caggttaagt caatctgggg    1680
cttccactgc ctgcattcca gtccccagag cttggtggtc ccgaaacggg aagtacatat    1740
tggggcatgg tggcctccgt gagcaaatgg tgtcttgggc aatctgaggc caggacagat    1800
gttgccccac ccactggaga tggtgctgag ggaggtgggg ggggccttct gggaaggtga    1860
gtggagaggg gcacctgccc cccgccctcc ccatccccta ctcccactgc tcagcgcggg    1920
ccattgcaag ggtgccacac aatgtcttgt ccaccctggg acacttctga gtatgaagcg    1980
ggatgctatt aaaaactaca tggggaaaca ggtgcaaacc ctggagatgg attgtaagag    2040
ccagtttaaa tctgcactct gctgctcctc ccccaccccc accttccact ccatacaatc    2100
tgggcctggt ggagtcttcg cttcagagcc attcggccag gtgcgggtga tgttcccatc    2160
tcctgcttgt gggcatgccc tggctttgtt tttatacaca taggcaaggt gagtcctctg    2220
tggaattgtg attgaaggat tttaaagcag gggaggagag taggggggcat ctctgtacac    2280 tctgggggta aaacagggaa ggcagtgcct gagcatgggg acaggtgagg tggggctggg    2340 cagacccccct gtagcgttta gcaggatggg ggccccaggt actgtggaga gcatagtcca    2400
gcctgggcat ttgtctccta gcagcctaca ctggctctgc tgagctgggc ctgggtgctg    2460
aaagccagga tttgggggcta ggcgggaaga tgttcgccca attgcttggg gggttggggg    2520
gatggaaaag gggagcacct ctaggctgcc tggcagcagt gagccctggg cctgtggcta    2580
cagccaggga accccacctg gacacatggc cctgcttcta agccccccag ttaggcccaa    2640
aggaatggtc cactgagggc ctcctgctct gcctgggctg ggccagggggc tttgaggaga    2700 gggtaaacat aggcccggag atggggctga cacctcgagt ggccagaata tgcccaaacc    2760
ccggcttctc ccttgtccct aggcagaggg gggtcccttc ttttgttccc tctggtcacc    2820
acaatgcttg atgccagctg ccataggaag agggtgctgg ctggccatgg tggcacacac    2880
ctgtcctccc agcactttgc agggctgagg tggaaggacc gcttaagccc aggtgttcaa    2940
ggctgctgtg agctgtgttc gagccactac actccagcct ggggacggag caaaactttg    3000
cctcaaaaca aattttaaaa agaaagaaag aaggaaagag ggtatgtttt tcacaattca    3060
tgggggcctg catggcagga gtggggacag gacacctgct gttcctggag tcgaaggaca    3120
agcccacagc ccagattccg gttctcccaa ctcaggaaga gcatgccctg ccctctgggg    3180
aggctggcct ggccccagcc ctcagctgct gaccttgagg cagagacaac ttctaagaat    3240
ttggctgcca gaccccaggc ctggctgctg ctgtgtggag agggaggcgg cccgcagcag    3300
aacagccacc gcacttcctc ctcagcttcc tctggtgcgg ccctgccctc tcttctctgg    3360 accctttttac aactgaacgc atctgggctt cgtggtttcc tgttttcagc gaaatttact    3420
ctgagctccc agttccatct tcatccatgg ccacaggccc tgcctacaac gcactaggga    3480
cgtccctccc tgctgctgct ggggaggggc aggctgctgg agccgccctc tgagttgccc    3540
gggatggtag tgcctctgat gccagccctg gtggctgtgg gctggggtgc atgggagagc    3600
tgggtgcgag aacatggcgc ctccagggggg cgggaggagc actaggggct ggggcaggag    3660
gctcctggag cgctggattc gtggcacagt ctgaggccct gagagggaaa tccatgctttt    3720 taagaactaa ttcattgtta ggagatcaat caggaattag gggccatctt acctatctcc    3780
tgacattcac agtttaatag agacttcctg cctttattcc ctcccaggga gaggctgaag    3840
gaatggaatt gaaagcacca tttggagggt tttgctgaca cagcggggac tgctcagcac    3900
tccctaaaaa cacaccatgg aggccactgg tgactgctgg tgggcaggct ggccctgcct    3960
gggggagtcc gtggcgatgg gcgctggggt ggaggtgcag gagccccagg acctgctttt    4020
```

```
caaaagactt ctgcctgacc agagctccca ctacatgcag tggcccaggg cagaggggct      4080
gatacatggc cttttttcagg gggtgctcct cgcggggtgg acttgggagt gtgcagtggg      4140
acagggggct gcaggggtcc tgccaccacc gagcaccaac ttggcccctg ggtcctgcc       4200 tcatgaatga ggccttcccc agggctggcc tgactgtgct gggggctggg ttaacgtttt      4260
ctcagggaac acaatgcac gaaagaggaa ctggggttgc taaccaggat gctgggaaca      4320
aaggcctctt gaagcccagc cacagcccag ctgagcatga ggcccagccc atagacggca      4380
caggccacct ggcccattcc ctgggcattc cctgctttgc attgctgctt ctcttcaccc      4440
catgagggct atgtcaccct aactatcctg gaatgtgttg agagggattc tgaatgatca      4500
atatagcttg gtgagacagt gccgagatag atagccatgt ctgccttggg cacgggagag      4560
ggaagtggca gcatgcatgc tgtttcttgg ccttttctgt tagaatactt ggtgctttcc      4620
aacacacttt cacatgtgtt gtaacttgtt tgatccaccc ccttccctga aaatcctggg      4680
aggttttatt gctgccattt aacacagagg gcaatagagg ttctgaaagg tctgtgtctt      4740
gtcaaaacaa gtaaacggtg gaactacgac taaa                                 4774
```

<210> SEQ ID NO 4
<211> LENGTH: 311
<212> TYPE: PRT
<213> ORGANISM: Homo sapiens

<400> SEQUENCE: 4

```
Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
```

```
                        245                 250                 255
Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
            275                 280                 285

Pro Gly Pro Gly Asp Val Phe Phe Pro Ser Leu Asp Pro Val Pro Asp
            290                 295                 300

Ser Pro Asn Phe Glu Val Ile
305                 310

<210> SEQ ID NO 5
<211> LENGTH: 30
<212> TYPE: PRT
<213> ORGANISM: Artificial Sequence
<220> FEATURE:
<223> OTHER INFORMATION: Consensus sequence for PD-L3

<400> SEQUENCE: 5

Ile Thr Ala Ala Ala Leu Ala Thr Gly Ala Cys Ile Val Gly Ile Leu
1               5                   10                  15

Cys Leu Pro Leu Ile Leu Leu Val Tyr Lys Gln Arg Gln
            20                  25                  30

<210> SEQ ID NO 6
<211> LENGTH: 1316
<212> TYPE: DNA
<213> ORGANISM: Mus musculus

<400> SEQUENCE: 6
ggagtcctcc ccttggagcc tgggaggcct agggagaaag tagttctctt tcggtggcag      60
ggttgctgtc gagggcaccg agcaggagga taggtcgaca gagacgagga gttctggctc     120
ctcctgcaga catgcaccag cggctgctgg gctcgtccct gggcctcgcc ccgcgcgggg     180
ggctctgaat gcctgccgcc gcccccatga gcaccggc ctgggctccc gcccctaagc      240
ctctgctcgc ggagactgag ccatgtgggc ctggggctgg gccgctgcag cgctcctctg     300
gctacagact gcaggagccg ggcccggca ggagctcaag aagtctcggc agctgtttgc      360
gcgtgtggat ccccccaata ttaccacgtc caaccgtgag ggattcccag ctccgtcaa      420 gccccccggaa gcctctggac ctgagctctc agatgcccac atgacgtggt tgaactttgt     480
ccgacggcca gatgatgggt cctctagaaa acggtgtcgt ggccgggaca agaagtcgcg     540
aggcctctca ggtctcccag ggcccccagg acctcctggc cctcctggtc ccctggctc     600 ccctggtgtg ggcgttaccc cagaggcctt actgcaggaa tttcaggaga tactgaaaga     660
ggccacagaa cttcgattct cagggctacc agacacattg ttaccccagg aacccagcca     720
acggctggtg gttgaggcct tctactgccg tttgaaaggc cctgtgctgg tggacaagaa     780
gactctggtg gaactgcaag gattccaagc tcctactact cagggcgcct tcctgcgggg     840
atctggcctg agcctgtcct tgggccgatt cacagcccca gtctctgcca tcttccagtt     900
ttctgccagc ctgcacgtgg accacagtga actgcagggc agaggccggt tgcgtacccg     960
ggatatggtc cgtgttctca tctgtattga gtccttgtgt catcgtcata cgtccctgga    1020
ggctgtatca ggtctggaga gcaacagcag ggtcttcaca gtgcaggttc agggggctgct    1080 gcatctacag tctggacagt atgtctctgt gttcgtggac aacagttctg gggcagtcct    1140
caccatccag aacacttcca gcttctcggg aatgcttttg ggtacctagc ggagctgaag    1200
aaacgattgt ggattgagga accaacacct tgcttcttag aggagctgaa aaggactact    1260
```
cactcccctt ttaatagttt tcatagcaat aaagaactcc aaacttcttc atcgct      1316

<210> SEQ ID NO 7
<211> LENGTH: 308
<212> TYPE: PRT
<213> ORGANISM: Mus musculus

<400> SEQUENCE: 7

```
Met Trp Ala Trp Gly Trp Ala Ala Ala Leu Leu Trp Leu Gln Thr
1               5                   10                  15

Ala Gly Ala Gly Ala Arg Gln Glu Leu Lys Lys Ser Arg Gln Leu Phe
            20                  25                  30

Ala Arg Val Asp Ser Pro Asn Ile Thr Thr Ser Asn Arg Glu Gly Phe
        35                  40                  45

Pro Gly Ser Val Lys Pro Glu Ala Ser Gly Pro Glu Leu Ser Asp
    50                  55                  60

Ala His Met Thr Trp Leu Asn Phe Val Arg Arg Pro Asp Asp Gly Ser
65              70                  75                  80

Ser Arg Lys Arg Cys Arg Gly Arg Asp Lys Lys Ser Arg Gly Leu Ser
                85                  90                  95

Gly Leu Pro Gly Pro Gly Pro Gly Pro Gly Pro Gly
            100                 105                 110

Ser Pro Gly Val Gly Val Thr Pro Glu Ala Leu Leu Gln Glu Phe Gln
            115                 120                 125

Glu Ile Leu Lys Glu Ala Thr Glu Leu Arg Phe Ser Gly Leu Pro Asp
        130                 135                 140

Thr Leu Leu Pro Gln Glu Pro Ser Gln Arg Leu Val Val Glu Ala Phe
145                 150                 155                 160

Tyr Cys Arg Leu Lys Gly Pro Val Leu Val Asp Lys Lys Thr Leu Val
                165                 170                 175

Glu Leu Gln Gly Phe Gln Ala Pro Thr Thr Gln Gly Ala Phe Leu Arg
            180                 185                 190

Gly Ser Gly Leu Ser Leu Ser Leu Gly Arg Phe Thr Ala Pro Val Ser
        195                 200                 205

Ala Ile Phe Gln Phe Ser Ala Ser Leu His Val Asp His Ser Glu Leu
    210                 215                 220

Gln Gly Arg Gly Arg Leu Arg Thr Arg Asp Met Val Arg Val Leu Ile
225                 230                 235                 240

Cys Ile Glu Ser Leu Cys His Arg His Thr Ser Leu Glu Ala Val Ser
                245                 250                 255

Gly Leu Glu Ser Asn Ser Arg Val Phe Thr Val Gln Val Gln Gly Leu
            260                 265                 270

Leu His Leu Gln Ser Gly Gln Tyr Val Ser Val Phe Val Asp Asn Ser
        275                 280                 285

Ser Gly Ala Val Leu Thr Ile Gln Asn Thr Ser Ser Phe Ser Gly Met
    290                 295                 300

Leu Leu Gly Thr
305
```

<210> SEQ ID NO 8
<211> LENGTH: 1055
<212> TYPE: DNA
<213> ORGANISM: Homo sapiens

<400> SEQUENCE: 8
ctcgccgcgc tgagccgcct cgggacggag ccatgcggcg ctgggcctgg gccgcggtcg      60

```
tggtcctcct cgggccgcag ctcgtgctcc tcggggcgt cggggcccgg cgggaggcac      120
agaggacgca gcagcctggc cagcgcgcag atcccccaa cgccaccgcc agcgcgtcct      180
cccgcgaggg gctgcccgag gcccccaagc catcccaggc ctcaggacct gagttctccg     240
acgcccacat gacatggctg aactttgtcc ggcggccgga cgacggcgcc ttaaggaagc     300
ggtgcggaag cagggacaag aagccgcggg atctcttcgg tccccagga cctccaggtg     360 cagaagtgac cgcggagact ctgcttcacg agtttcagga gctgctgaaa gaggccacgg     420
agcgccggtt ctcagggctt ctggacccgc tgctgcccca gggggcgggc ctgcggctgg     480
tgggcgaggc ctttcactgc cggctgcagg tccccgccg ggtggacaag cggacgctgg      540
tggagctgca tggtttccag gctcctgctg cccaaggtgc cttcctgcga ggctccggtc     600
tgagcctggc ctcgggtcgg ttcacggccc ccgtgtccgg catcttccag ttctctgcca     660
gtctgcacgt ggaccacagt gagctgcagg gcaaggcccg gctgcgggcc cgggacgtgg     720
tgtgtgttct catctgtatt gagtccctgt gccagcgcca cacgtgcctg gaggccgtct     780
caggcctgga gagcaacagc agggtcttca cgctacaggt gcaggggctg ctgcagctgc     840
aggctggaca gtacgcttct gtgtttgtgg acaatggctc cggggccgtc ctcaccatcc     900
aggcgggctc cagcttctcc gggctgctcc tgggcacgtg agggcgccca ggggggctgg     960
cgaggagctg ccgccggatc ccggggaccc tcctactgat gcccgtggtc accacaataa    1020
agagccctcc accctcaaaa aaaaaaaaaa aaaaa                                1055

<210> SEQ ID NO 9
<211> LENGTH: 302
<212> TYPE: PRT
<213> ORGANISM: Homo sapiens

<400> SEQUENCE: 9

Met Arg Arg Trp Ala Trp Ala Ala Val Val Leu Leu Gly Pro Gln
1               5                   10                  15

Leu Val Leu Leu Gly Gly Val Gly Ala Arg Arg Glu Ala Gln Arg Thr
            20                  25                  30

Gln Gln Pro Gly Gln Arg Ala Asp Pro Pro Asn Ala Thr Ala Ser Ala
        35                  40                  45

Ser Ser Arg Glu Gly Leu Pro Glu Ala Pro Lys Pro Ser Gln Ala Ser
    50                  55                  60

Gly Pro Glu Phe Ser Asp Ala His Met Thr Trp Leu Asn Phe Val Arg
65                  70                  75                  80

Arg Pro Asp Asp Gly Ala Leu Arg Lys Arg Cys Gly Ser Arg Asp Lys
                85                  90                  95

Lys Pro Asp Leu Phe Gly Pro Pro Gly Pro Pro Gly Ala Glu Val
            100                 105                 110

Thr Ala Glu Thr Leu Leu His Glu Phe Gln Glu Leu Leu Lys Glu Ala
        115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
            180                 185                 190

Ala Ser Gly Arg Phe Thr Ala Pro Val Ser Gly Ile Phe Gln Phe Ser
        195                 200                 205
```

```
Ala Ser Leu His Val Asp His Ser Glu Leu Gln Gly Lys Ala Arg Leu
    210                 215                 220

Arg Ala Arg Asp Val Val Cys Val Leu Ile Cys Ile Glu Ser Leu Cys
225                 230                 235                 240

Gln Arg His Thr Cys Leu Glu Ala Val Ser Gly Leu Glu Ser Asn Ser
                245                 250                 255

Arg Val Phe Thr Leu Gln Val Gln Gly Leu Leu Gln Leu Gln Ala Gly
            260                 265                 270

Gln Tyr Ala Ser Val Phe Val Asp Asn Gly Ser Gly Ala Val Leu Thr
        275                 280                 285

Ile Gln Ala Gly Ser Ser Phe Ser Gly Leu Leu Leu Gly Thr
    290                 295                 300

<210> SEQ ID NO 10
<211> LENGTH: 17
<212> TYPE: PRT
<213> ORGANISM: Artificial Sequence
<220> FEATURE:
<223> OTHER INFORMATION: Consensus sequence for Treg-sTNF

<400> SEQUENCE: 10

Ile Phe Gln Phe Ser Ala Ser Leu His Val Asp His Ser Glu Leu Gln
1               5                   10                  15

Gly
```

REGULATORY T CELL MEDIATOR PROTEINS AND USES THEREOF

INTRODUCTION

This application is a U.S. Divisional Patent Application of U.S. patent application Ser. No. 12/732,371 filed Mar. 26, 2010, now U.S. Pat. No. 8,231,872 which is a Continuation-in-Part of U.S. patent application Ser. No. 11/912,397 filed Jun. 4, 2008, now U.S. Pat. No. 8,236,304 which claims benefit of PCT/US2006/015239, filed Apr. 24, 2006 and U.S. Provisional Patent Application No. 60/674,567, filed Apr. 25, 2005, the contents of which including the sequence listing are incorporated herein by reference in their entireties.

BACKGROUND OF THE INVENTION

Induction of an immune response requires T cell expansion, differentiation, contraction and establishment of T cell memory. T cells must encounter antigen presenting cells (APCs) and communicate via T cell receptor (TCR)/major histocompatibility complex (MHC) interactions on APCs. Once the TCR/MHC interaction is established, other sets of receptor-ligand contacts between the T cell and the APC are required, i.e. co-stimulation via CD154/CD40 and CD28/B7.1-B7.2. The synergy between these contacts is suggested to result, in vivo, in a productive immune response capable of clearing pathogens and tumors, and in some cases capable of inducing autoimmunity.

Another level of control has been identified, namely regulatory T cells (Treg). This specific subset of T cells is generated in the thymus, delivered into the periphery, and is capable of constant and inducible control of T cells responses in vitro and in vivo (Sakaguchi (2000) Cell 101(5):455-8; Shevach (2000) Annu. Rev. Immunol. 18:423-49; Bluestone and Abbas (2003) Nat. Rev. Immunol. 3(3):253-7). Treg are represented by a CD4+ CD25+ phenotype and also express high levels of cytotoxic T lymphocyte-associated antigen-4 (CTLA-4), OX-40, 4-1BB and the glucocorticoid inducible TNF receptor-associated protein (GITR) (McHugh, et al. (2002) Immunity 16(2):311-23; Shimizu, et al. (2002) Nat. Immun. 3(2):135-42). Elimination of Treg cells by 5 day neonatal thymectomy or antibody depletion using anti-CD25, results in the induction of autoimmune pathology and exacerbation of T cells responses to foreign and self-antigens, including heightened anti-tumor responses (Sakaguchi, et al. (1985) J. Exp. Med. 161(1):72-87; Sakaguchi, et al. (1995) J. Immunol. 155(3):1151-64; Jones, et al. (2002) Cancer Immun. 2:1). In addition, Treg have also been involved in the induction and maintenance of transplantation tolerance (Hara, et al. (2001) J. Immunol. 166(6):3789-3796; Wood and Sakaguchi (2003) Nat. Rev. Immunol. 3:199-210), since depletion of Treg with anti-CD25 monoclonal antibodies results in ablation of transplantation tolerance and rapid graft rejection (Jarvinen, et al. (2003) Transplantation 76:1375-9). Among the receptors expressed by Treg, GITR seems to be an important component since in vitro or in vivo ligation of GITR on the surface of Treg with an agonistic monoclonal antibody results in rapid termination of Treg activity (McHugh, et al. (2002) supra; Shimizu, et al. (2002) supra), also resulting in autoimmune pathology (Shimizu, et al. (2002) supra) and ablation of transplantation tolerance.

DNA microarray analysis has been conducted with a population of Treg to identify genes differentially expressed by Treg (Gavin, et al. (2002) Nat. Immunol. 3(1):33-41; McHugh, et al. (2002) supra). The expression pattern of genes of CD4+ CD25- and CD4+ CD25+ T cells was compared (Gavin, et al. (2002) supra) as was the expression pattern of these two populations of cells after activation by anti-CD3 antibody and IL-2 for 12 and 48 hours (McHugh, et al. (2002) supra). However, gene regulation by GITR signaling was not assessed.

T cell activation is dependent upon signs transferred through antigen-specific T cells receptor recognition and accessory receptors on the T cell. As the maintenance of immunologic peripheral homeostatis is regulated by co-stimulatory molecules, which play a critical role in suppressing autoreactive lymphocytes, identification of these co-stimulatory molecules and co-inhibitory ligands is needed.

Costimulatory and co-inhibitory ligands and receptors not only provide a "2nd signal" for T cell activation, but also a balanced network of positive and negative signal to maximize immune responses against infection while limiting immunity to self. The best characterized costimulatory ligands are B7.1 and B7.2, which are expressed by professional APCs, and whose receptors are CD28 and CTLA-4 (Greenwald, R. J., Freeman, G. J., and Sharpe, A. H. (2005). Annu Rev Immunol 23, 515-548; Sharpe, A. H., and Freeman, G. J. (2002) Nat Rev Immunol 2, 116-126). CD28 is expressed by naïve and activated T cells and is critical for optimal T cell activation. In contrast, CTLA-4 is induced upon T cell activation and inhibits T cell activation by binding to B7.1/B7.2, thus impairing CD28-mediated costimulation. CTLA-4 also transduces negative signaling through its cytoplasmic ITIM motif (Teft, W. A., Kirchhof, M. G., and Madrenas, J. (2006). Annu Rev Immunol 24, 65-97; Teft, W. A., Kirchhof, M. G., and Madrenas, J. (2006). Annu Rev Immunol 24, 65-97. B7.1/B7.2 KO mice are impaired in adaptive immune response Borriello, F., Sethna, M. P., Boyd, S. D., Schweitzer, A. N., Tivol, E. A., Jacoby, D., Strom, T. B., Simpson, E. M., Freeman, G. J., and Sharpe, A. H. (1997)) Immunity 6, 303-313; Freeman, G. J., Borriello, F., Hodes, R. J., Reiser, H., Hathcock, K. S., Laszlo, G., McKnight, A. J., Kim, J., Du, L., Lombard, D. B., and et al. (1993). Science 262, 907-909), whereas CTLA-4 KO mice can not adequately control inflammation and develop systemic autoimmune diseases (Chambers, C. A., Sullivan, T. J., and Allison, J. P. (1997) Immunity 7, 885-895; Tivol, E. A., Borriello, F., Schweitzer, A. N., Lynch, W. P., Bluestone, J. A., and Sharpe, A. H. (1995) Immunity 3, 541-547; Waterhouse, P., Penninger, J. M., Timms, E., Wakeham, A., Shahinian, A., Lee, K. P., Thompson, C. B., Griesser, H., and Mak, T. W. (1995). Science 270, 985-988.

The B7 family ligands have expanded to include costimulatory B7-H2 (ICOS Ligand) and B7-H3, as well as co-inhibitory B7-H1 (PD-L1), B7-DC (PD-L2), B7-H4 (B7S1 or B7x), and B7-H6 Brandt, C. S., Baratin, M., Yi, E. C., Kennedy, J., Gao, Z., Fox, B., Haldeman, B., Ostrander, C. D., Kaifu, T., Chabannon, C., et al. (2009) J Exp Med 206, 1495-1503; Greenwald, R. J., Freeman, G. J., and Sharpe, A. H. (2005) Annu Rev Immunol 23, 515-548.

Inducible costimulatory (ICOS) molecule is expressed on activated T cells and binds to B7-H2 Yoshinaga, S. K., Whoriskey, J. S., Khare, S. D., Sarmiento, U., Guo, J., Horan, T., Shih, G., Zhang, M., Coccia, M. A., Kohno, T., et al. (1999). Nature 402, 827-832. ICOS is important for T cell activation, differentiation and function, as well as essential for T-helper-cell-induced B cell activation, Ig class switching, and germinal center (GC) formation Dong, C., Juedes, A. E., Temann, U. A., Shresta, S., Allison, J. P., Ruddle, N. H., and Flavell, R. A. (2001) Nature 409, 97-101; Tafuri, A., Shahinian, A., Bladt, F., Yoshinaga, S. K., Jordana, M., Wakeham, A., Boucher, L. M., Bouchard, D., Chan, V. S., Duncan, G., et al. (2001) Nature 409, 105-109; Yoshinaga, S. K., Whoriskey, J. S., Khare, S. D., Sarmiento, U., Guo, J., Horan, T., Shih, G., Zhang, M., Coccia, M. A., Kohno, T., et al. (1999) Nature 402, 827-832. Programmed Death 1 (PD-1) on the other hand, negatively regulates T cell responses. PD-1 KO mice develop lupus-like autoimmune disease, or autoimmune dilated cardiomyopathy depending upon the genetic background Nishimura, H., Nose, M., Hiai, H., Minato, N., and Honjo, T. (1999) Immunity 11, 141-151. Nishimura, H., Okazaki, T., Tanaka, Y., Nakatani, K., Hara, M., Matsumori, A., Sasayama, S., Mizoguchi, A., Hiai, H., Minato, N., and Honjo, T. (2001) Science 291, 319-322. The autoimmunity most likely results from the loss of signaling by both ligands PD-L1 and PD-L2. Recently, CD80 was identified as a second receptor for PD-L1 that transduces inhibitory signals into T cells Butte, M. J., Keir, M. E., Phamduy, T. B., Sharpe, A. H., and Freeman, G. J. (2007) Immunity 27, 111-122. The receptor for B7-H3 and B7-H4 still remain unknown.

B7-H6 is a newly identified B7 family ligand, which binds to an activating receptor NKp30 on natural killer cells in humans Brandt, C S., Baratin, M., Yi, E. C., Kennedy, J., Gao, Z., Fox, B., Haldeman, B., Ostrander, C D., Kaifu, T., Chabannon, C., et al. (2009). J Exp Med 206, 1495-1503.

The two inhibitory B7 family ligands, PD-L1 and PD-L2, have distinct expression patterns. PD-L2 is inducibly expressed on DCs and macrophages, whereas PD-L1 is broadly expressed on both hematopoietic cells (i.e. T cells, DCs, B cells, macrophages, and mesenchymal stem cells) and non-hematopoietic cell types (i.e. endothelial cells, pancreatic islet cells, and muscle cells) Keir, M. E., Butte, M. J., Freeman, G. J., and Sharpe, A. H. (2008) Annu Rev Immunol 26, 677-704; Okazaki, T., and Honjo, T. (2006). The PD-1-PD-L pathway in immunological tolerance. Trends Immunol 27, 195-201. Consistent with the immune-suppressive role of PD-1 receptor, studies using PD-L1−/− and PD-L2−/− mice have shown that both ligands have overlapping roles in inhibiting T cell proliferation and cytokine production Keir, M. E., Liang, S. C., Guleria, I., Latchman, Y. E., Qipo, A., Albacker, L. A., Koulmanda, M., Freeman, G. J., Sayegh, M. H., and Sharpe, A. H. (2006). Tissue expression of PD-L1 mediates peripheral T cell tolerance. J Exp Med 203, 883-895. PD-L1 in particular, contributes significantly to tempering the development of autoimmunity and promoting peripheral tolerance Keir, M. E., Butte, M. J., Freeman, G. J., and Sharpe, A. H. (2008). PD-1 and its ligands in tolerance and immunity. Annu Rev Immunol 26, 677-704. PD-L1 deficiency enhances disease progression in both the NOD model of autoimmune diabetes and the murine model of multiple sclerosis (EAE) Ansari, M. J., Salama, A. D., Chitnis, T., Smith, R. N., Yagita, H., Akiba, H., Yamazaki, T., Azuma, M., Iwai, H., Khoury, S. J., et al. (2003). The programmed death-1 (PD-1) pathway regulates autoimmune diabetes in nonobese diabetic (NOD) mice. J Exp Med 198, 63-69; Fife, B. T., Guleria, I., Gubbels Hupp, M., Eagar, T. N., Tang, Q., Bour-Jordan, H., Yagita, H., Azuma, M., Sayegh, M. H., and Bluestone, J. A. (2006). Insulin-induced remission in new-onset NOD mice is maintained by the PD-1-PD-L1 pathway. J Exp Med 203, 2737-2747; Latchman, Y. E., Liang, S. C., Wu, Y., Chemova, T., Sobel, R. A., Klemm, M., Kuchroo, V. K., Freeman, G. J., and Sharpe, A. H. (2004). PD-L1-deficient mice show that PD-L1 on T cells, antigen-presenting cells, and host tissues negatively regulates T cells. Proc Natl Acad Sci USA 101, 10691-10696; Salama, A. D., Chitnis, T., Imitola, J., Ansari, M. J., Akiba, H., Tushima, F., Azuma, M., Yagita, H., Sayegh, M. H., and Khoury, S. J. (2003). Critical role of the programmed death-1 (PD-1) pathway in regulation of experimental autoimmune encephalomyelitis. J Exp Med 198, 71-78.

PD-L1−/− T cells produce elevated levels of the pro-inflammatory cytokines in both disease models. In addition, the tissue expression of PD-L1 uniquely contributes to its capacity of regionally controlling inflammation. Studies in NOD mice have demonstrated that PD-L1 expression on hematopoietic cells alone is insufficient to prevent autoimmune diabetes. Instead, its expression within pancreas is critical for protection against self-reactive CD4+ T cells Keir, M. E., Liang, S. C., Guleria, I., Latchman, Y. E., Qipo, A., Albacker, L. A., Koulmanda, M., Freeman, G. J., Sayegh, M. H., and Sharpe, A. H. (2006). Tissue expression of PD-L1 mediates peripheral T cell tolerance. J Exp Med 203, 883-895. PD-L1 is also highly expressed on placental syncytiotrophoblasts, which critically control the maternal immune responses to allogeneic fetus Guleria, I., Khosroshahi, A., Ansari, M. J., Habicht, A., Azuma, M., Yagita, H., Noelle, R. J., Coyle, A., Mellor, A. L., Khoury, S. J., and Sayegh, M. H. (2005). A critical role for the programmed death ligand 1 in fetomaternal tolerance. J Exp Med 202, 231-237.

Consistent with its immune-suppressive role, PD-L1 potently suppresses anti-tumor immune responses and aids tumor escape from immune surveillance. PD-L1 can induce apoptosis of infiltrating cytotoxic CD8+ T cells, which express high level of PD-1 (Dong, H., and Chen, L. (2003). J Mol Med 81, 281-287; Dong, H. et al., (2002), Nat Med 8, 793-800). Studies in murine tumor models have shown that blocking the PD-L1:PD-1 signaling pathway, in conjunction with other immune therapies, prevents tumor progression by enhancing anti-tumor CTL activity and cytokine production Blank et al., (2004), Cancer Res 64, 1140-1145; Blank et al., (2005), Cancer Immunol Immunother 54, 307-314. Blank et al., (2006). Int J Cancer 119, 317-327; Geng et al., (2006), Int J Cancer 118, 2657-2664; Iwai et al., (2002), Proc Natl Acad Sci USA 99, 12293-12297. Iwai et al., (2005). Int Immunol 17, 133-144. Moreover, a recent study by the inventors shows that PD-L1 expression on DCs promotes the induction of adaptive Foxp3+ CD4+ regulatory T cells (aTregs), and PD-L1 is a potent inducer of aTregs within the tumor microenvironment (Wang et al., (2008), Proc Natl Acad Sci USA 105, 9331-9336. Disruption of this pathway by PD-L1 mAb or PD-L1 KO mice reduced tumor-mediated induction of aTregs and reduced tumor growth.

Based on the foregoing, the elucidation of other novel B7 type family members and ligands and modulators thereof would be useful given the role of these family members in regulating immunity.

SUMMARY OF THE INVENTION

The present invention relates to novel regulatory T cell proteins. One protein, designated PD-L3, is a new member of the PD-L1 family, and co-stimulates αCD3 proliferation of T cells in vitro. A second, TNF-like, protein has also been identified which is upregulated upon αCD3/αGITR stimulation. This protein has been designated $T^{reg}$-sTNF. Proteins, antibodies, method of using these proteins and ligands specific thereto in modulating activated T cells and methods for using the same as therapeutics, especially in treating cancer, autoimmune diseases, viral infection, allergy and inflammatory conditions are disclosed.

In particular the invention relates to methods of using these proteins and binding agent compounds, preferably antibodies, which bind or modulate (agonize or antagonize) the activity of these proteins, as immune modulators and for the treatment of cancer, autoimmune disease, allergy, infection and inflammatory conditions, e.g. multiple sclerosis.

As described in detail infra, this invention relates to a novel T cell co-stimulatory molecule, which is a member of the B7 family of ligands, referred to herein as PD-L3. This protein is a novel inhibitory ligand, which extracellular Ig-V domain bears homology to the two known B7 family ligands Programmed Death Ligand 1 and 2 (PD-L1 and PD-L2) and exhibits unique sequence features and distinctive expression patterns in vitro and in vivo on subsets of APCs and T cells, (which distinguishes PD-L3 from other B7 family ligands). This protein has been shown to have a functional impact on CD4+ and CD8+ T cell proliferation and differentiation (suppresses CD4+ and CD8+ T cell proliferation, as well as cytokine production). Based on its expression pattern and inhibitory impact on T cells, PD-L3 apparently functions as a regulatory ligand that negatively regulates T cell responses during cognate interactions between T cells and myeloid derived APCs.

While PD-L3 appears to be a member of the B7 family of ligands, unlike other B7 family ligands, this molecule contains only an Ig-V domain without an Ig-C domain, and is phylogenically closer to the B7 family receptor Programmed Death-1 (PD-1). Based thereon, PD-L3, and agonists or antagonists specific thereto can be used to regulate T cell activation and differentiation, and more broadly to modulate the regulatory network that controls immune responses. In particular PD-L3 proteins and PD-L3 agonists or antagonists, preferably antibodies specific to PD-L3 are useful in modulating immune responses in autoimmunity, inflammatory responses and diseases, allergy, cancer, infectious disease and transplantation.

Therefore, the present invention in part relates to compositions e.g., for therapeutic, diagnostic or immune modulatory usage containing an isolated PD-L3 protein or fusion protein, e.g., an PD-L3-Ig fusion protein, comprising an amino acid sequence that preferably is at least 70-90% identical to the human or murine PD-L3 polypeptide set forth in SEQ ID NO:2, 4 or 5 or an ortholog, or fragment thereof that modulates PD-L3 in vivo and a pharmaceutically acceptable carrier. In some embodiments, the PD-L3 protein may be directly or indirectly linked to a heterologous (non-PD-L3) protein.

The present invention also provides expression vectors comprising an isolated nucleic acid encoding a PD-L3 protein that is at least 70-90% identical to the human PD-L3 amino acid sequence set forth in SEQ ID NO:2, 4 or 5 or a fragment thereof, which optionally is fused to a sequence encoding another protein such as an Ig polypeptide, e.g., an Fc region or a reporter molecule; and host cells containing said vectors.

The present invention also specifically relates to an isolated binding agent, preferably an antibody or antibody fragment which specifically binds to a PD-L3 protein comprising the amino acid sequence set forth in SEQ ID NO:2, 4 or 5 or a variant, fragment or ortholog thereof. In a preferred embodiment, the binding agent modulates (agonizes or antagonizes) PD-L3 activity in vitro or in vivo. In most preferred embodiments, the binding agent is an agonistic or antagonistic antibody.

The present invention further provides methods for modulating an immune cell response by contacting an immune cell in vitro or in vivo with a PD-L3 protein, or binding agent specific thereto, in the presence of a primary signal so that a response of the immune cell is modulated. (Interaction of PD-L3 or a modulator thereof transmits a signal to immune cells, regulating immune responses. PD-L3 protein is expressed at high levels on myeloid antigen presenting cells, including myeloid dendritic cells (DCs) and macrophages, and at lower densities on CD4+ and CD8+ T cells. Upon immune activation, PD-L3 expression is upregulated on myeloid APCs, but downregulated on CD4+ T cells). Therefore, the PD-L3 nucleic acids and polypeptides of the present invention, and agonists or antagonists thereof are useful, e.g., in modulating the immune response.

In another aspect this invention provides isolated nucleic acid molecules encoding PD-L3 polypeptides, as well as nucleic acid fragments suitable as primers or hybridization probes for the detection of PD-L3-encoding nucleic acids. In one embodiment, a PD-L3 nucleic acid molecule of the invention is at least about 70%, 75%, 80%, 85%, 90%, 91%, 92%, 93%, 94%, 95%, 96%, 97%, 98%, 99% or more identical to the nucleotide sequence (e.g., to the entire length of the nucleotide sequence) encoding PD-L3 in SEQ ID NO:1 or 3 shown herein or a complement thereof.

In another embodiment, a PD-L3 nucleic acid molecule includes a nucleotide sequence encoding a polypeptide having an amino acid sequence having a specific percent identity to the amino acid sequence of SEQ ID NO: 2, 4 or 5. In a preferred embodiment, a PD-L3 nucleic acid molecule includes a nucleotide sequence encoding a polypeptide having an amino acid sequence at least about 71%, 75%, 80%, 85%, 90%, 95%, 96%, 97%, 98%, 99% or more identical to the entire length of the amino acid sequence of SEQ ID NO: 2, 4 or 5.

In another preferred embodiment, an isolated nucleic acid molecule encodes the amino acid sequence of human or murine PD-L3 or a conserved region or functional domain therein. In yet another preferred embodiment, the nucleic acid molecule includes a nucleotide sequence encoding a polypeptide having the amino acid sequence of SEQ ID NO: 2, 4 or 5. In yet another preferred embodiment, the nucleic acid molecule is at least about 50, 100, 150, 200, 250, 300, 350, 400, 450, 500, 550, 600, 650, 700, 750, 800, 850, 900, 950, 1000, 1050, 1100, 1150 or more nucleotides in length. In a further preferred embodiment, the nucleic acid molecule is at least about 50, 100, 150, 200, 250, 300, 350, 400, 450, 500, 550, 600, 650, 700, 750, 800, 850, 900, 950, 1000, 1050, 1100, 1150 or more nucleotides in length and encodes a polypeptide having a PD-L3 activity or modulating PD-L3 function (as described herein).

Another embodiment of the invention features nucleic acid molecules, preferably PD-L3 nucleic acid molecules, which specifically detect PD-L3 nucleic acid molecules relative to nucleic acid molecules encoding non-PD-L3 polypeptides. For example, in one embodiment, such a nucleic acid molecule is at least about 880, 900, 950, 1000, 1050, 1100, 1150 or more nucleotides in length and hybridizes under stringent conditions to a nucleic acid molecule encoding the polypeptide shown in SEQ ID NO: 2, 4 or 5, or a complement thereof. In another embodiment, such a nucleic acid molecule is at least 20, 30, 40, 50, 100, 150, 200, 250, 300 or more nucleotides in length and hybridizes under stringent conditions to a nucleic acid molecule encoding a fragment of PD-L3, e.g., comprising n at least 20, 30, 40, 50, 100, 150, 200, 250, 300, 350, 400, 450, 500, 550, 600, 650, 700, 750, 800, 850, 900, 950, 1000, 1050, 1100, 1150 or more nucleotides in length, includes at least 15 (i.e., 15 contiguous) nucleotides of the disclosed nucleic acid sequence in SEQ ID NO:1 and 3 encoding the PD-L3 polypeptides in SEQ ID NO: 2, 4 or 5, or a complement thereof, and hybridizes under stringent conditions to a nucleic acid molecule comprising the nucleotide sequence shown in SEQ ID NO: 1, or 3 or a complement thereof.

In still other preferred embodiments, the nucleic acid molecule encodes a naturally occurring allelic variant of a polypeptide comprising the amino acid sequence of SEQ ID NO: 2 or 4 or 5, wherein the nucleic acid molecule hybridizes to a complement of a nucleic acid molecule comprising SEQ ID NO: 1 or 3, or a complement thereof, under stringent conditions.

Another embodiment of the invention provides an isolated nucleic acid molecule which is antisense to a PD-L3 nucleic acid molecule, e.g., is antisense to the coding strand of a PD-L3 nucleic acid molecule as shown in SEQ ID NO: 1 or 3.

Another aspect of the invention provides a vector comprising a PD-L3 nucleic acid molecule. In certain embodiments, the vector is a recombinant expression vector.

In another embodiment, the invention provides a host cell containing a vector of the invention. In yet another embodiment, the invention provides a host cell containing a nucleic acid molecule of the invention. The invention also provides a method for producing a polypeptide, preferably a PD-L3 polypeptide, by culturing in a suitable medium, a host cell, e.g., a mammalian host cell such as a non-human mammalian cell, of the invention containing a recombinant expression vector, such that the polypeptide is produced.

Another aspect of this invention features isolated or recombinant PD-L3 polypeptides (e.g., proteins, polypeptides, peptides, or fragments or portions thereof). In one embodiment, an isolated PD-L3 polypeptide or PD-L3 fusion protein includes at least one or more of the following domains: a signal peptide domain, an IgV domain, an extracellular domain, a transmembrane domain, and a cytoplasmic domain.

In a preferred embodiment, a PD-L3 polypeptide includes at least one or more of the following domains: a signal peptide domain, an IgV domain, an extracellular domain, a transmembrane domain, and a cytoplasmic domain, and has an amino acid sequence at least about 71%, 75%, 80%, 85%, 90%, 91%, 92%, 93%, 94%, 95%, 96%, 97%, 98%, 99% or more identical to the amino acid sequence of SEQ ID NO: 2 or 4 or 5. In another preferred embodiment, a PD-L3 polypeptide includes at least one or more of the following domains: a signal peptide domain, an IgV domain, an extracellular domain, a transmembrane domain, and a cytoplasmic domain, and has a PD-L3 activity (as described herein).

In yet another preferred embodiment, a PD-L3 polypeptide includes at least one or more of the following domains: a signal peptide domain, an IgV domain, an extracellular domain, a transmembrane domain, and a cytoplasmic domain, and is encoded by a nucleic acid molecule having a nucleotide sequence which hybridizes under stringent hybridization conditions to a complement of a nucleic acid molecule comprising the nucleotide sequence of SEQ ID NO: 1 or 3.

In another embodiment, the invention features fragments or portions of the polypeptide having the amino acid sequence of SEQ ID NO: 2 or 4 or 5, wherein the fragment comprises at least 15 amino acids (i.e., contiguous amino acids) of the amino acid sequence of SEQ ID NO: 2 or 4. In another embodiment, a PD-L3 polypeptide comprises or consists of the amino acid sequence of SEQ ID NO: 2, 4 or 5. In another embodiment, the invention features a PD-L3 polypeptide which is encoded by a nucleic acid molecule consisting of a nucleotide sequence at least about 70%, 75%, 80%, 85%, 90%, 91%, 92%, 93%, 94%, 95%, 96%, 97%, 98%, 99% or more identical to a nucleotide sequence of SEQ ID NO: 1 or 3, or a complement thereof. This invention further features a PD-L3 polypeptide which is encoded by a nucleic acid molecule consisting of a nucleotide sequence which hybridizes under stringent hybridization conditions to a complement of a nucleic acid molecule comprising the nucleotide sequence of SEQ ID NO: 1 or 3.

The polypeptides of the present invention or portions thereof, e.g., biologically active portions thereof, can be operatively linked to a non-PD-L3 polypeptide (e.g., heterologous amino acid sequences) to form fusion polypeptides. The invention further features antibodies, such as monoclonal or polyclonal antibodies, that specifically bind polypeptides of the invention, preferably human PD-L3 polypeptides.

The invention also relates to methods of selecting anti-PD-L3 antibodies having desired functional properties from panels of monoclonal antibodies produced against this protein or a PD-L3-Ig fusion protein based on desired functional properties, e.g., modulating specific effects of PD-L3 on immunity such as the suppressive effect of the protein on TCR activation, the suppressive effect of the protein on CD4 T cell proliferative responses to anti-CD3, suppression of antigen specific proliferative responses of cognate CD4 T cells, the suppressive effects of PD-L3 on the expression of specific cytokines such as IL-2 and gamma interferon, et al. In a particularly preferred embodiment anti-PD-L3 antibodies for use as therapeutics will be selected that in vitro, in the presence of soluble PD-L3-proteins, e.g., PD-L3-Ig fusion protein enhance the suppressive effects of PD-L3-Ig on PD-L3 related immune functions. This is preferred as quite unexpectedly (shown infra) these antibodies in vivo behave opposite to what would be expected from their in vitro effect on immunity, i.e., these anti-PD-L3 monoclonal antibodies are immunosuppressive.

In addition, the PD-L3 polypeptides (or biologically active portions thereof) or modulators of the PD-L3 molecules, i.e., antibodies such as selected using the foregoing methods can be incorporated into pharmaceutical compositions, which optionally include pharmaceutically acceptable carriers.

In another embodiment, a PD-L3 protein is used as an inhibitory signal for inhibiting or decreasing immune cell activation. In this embodiment, the inhibitory signal binds to an inhibitory receptor (e.g., CTLA4 or PD-1) on an immune cell thereby antagonizing the primary signal which binds to an activating receptor (e.g., via a TCR, CD3, BCR, or Fc polypeptide). Inhibition includes, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

In particular embodiments, the primary signal is a ligand (e.g., CD3 or anti-CD3) that binds TCR and initiates a primary stimulation signal. Such TCR ligands are readily available from commercial sources and specific examples include anti-CD3 antibody OKT3, prepared from hybridoma cells obtained from the American Type Culture Collection, and anti-CD3 monoclonal antibody G19-4. In an alternative embodiment, a primary signal is delivered to a T cell through other mechanisms including a protein kinase C activator, such as a phorbol ester (e.g., phorbol myristate acetate), and a calcium ionophore (e.g., ionomycin, which raises cytoplasmic calcium concentrations), or the like. The use of such agents bypasses the TCR/CD3 complex but delivers a stimulatory signal to T cells. Other agents acting as primary signals can include natural and synthetic ligands. A natural ligand can include MHC with or without a peptide presented. Other ligands can include, but are not limited to, a peptide, polypeptide, growth factor, cytokine, chemokine, glycopeptide, soluble receptor, steroid, hormone, mitogen, such as PHA, or other superantigens, peptide-MHC tetramers (Altman, et al.

(1996) Science 274(5284):94-6) and soluble MHC dimers (Dal Porto, et al (1993) Proc Natl. Acad. Sci. USA 90: 6671-5).

Immune cells activated in accordance with the method of the instant invention can subsequently be expanded ex vivo and used in the treatment and prevention of a variety of diseases; e.g., human T cells which have been cloned and expanded in vitro maintain their regulatory activity (Groux, et al. (1997) Nature 389(6652):737-42). Prior to expansion, a source of T cells is obtained from a subject (e.g., a mammals such as a human, dog, cat, mouse, rat, or transgenic species thereof). T cells can be obtained from a number of sources, including peripheral blood mononuclear cells, bone marrow, lymph node tissue, cord blood, thymus tissue, tissue from a site of infection, spleen tissue, tumors or T cell lines. T cells can be obtained from a unit of blood collected from a subject using any number of techniques known to the skilled artisan, such as Ficoll™ separation.

In another aspect, the present invention provides a method for detecting the presence of a PD-L3 nucleic acid molecule, protein, or polypeptide in a biological sample by contacting the biological sample with an agent capable of detecting a PD-L3 nucleic acid molecule, protein, or polypeptide, such that the presence of a PD-L3 nucleic acid molecule, protein or polypeptide is detected in the biological sample. This PD-L3 expression can be used to detect certain disease sites such as inflammatory sites.

In another aspect, the present invention provides a method for detecting the presence of PD-L3 activity in a biological sample by contacting the biological sample with an agent capable of detecting an indicator of PD-L3 activity, such that the presence of PD-L3 activity is detected in the biological sample.

In another aspect, the invention provides a method for modulating PD-L3 activity, comprising contacting a cell capable of expressing PD-L3 with an agent that modulates PD-L3 activity, preferably an anti-PD-L3 antibody such that PD-L3 activity in the cell is modulated. In one embodiment, the agent inhibits PD-L3 activity. In another embodiment, the agent stimulates PD-L3 activity. In a further embodiment, the agent interferes with or enhances the interaction between a PD-L3 polypeptide and its natural binding partner(s). In one embodiment, the agent is an antibody that specifically binds to a PD-L3 polypeptide. In another embodiment, the agent is a peptide, peptidomimetic, or other small molecule that binds to a PD-L3 polypeptide.

In still another embodiment, the agent modulates expression of PD-L3 by modulating transcription of a PD-L3 gene, translation of a PD-L3 mRNA, or post-translational modification of a PD-L3 polypeptide. In another embodiment, the agent is a nucleic acid molecule having a nucleotide sequence that is antisense to the coding strand of a PD-L3 mRNA or a PD-L3 gene.

In one embodiment, the methods of the present invention are used to treat a subject having a disorder or condition characterized by aberrant, insufficient, or unwanted PD-L3 polypeptide or nucleic acid expression or activity by administering an agent which is a PD-L3 modulator to the subject. In one embodiment, the PD-L3 modulator is a PD-L3 polypeptide. In another embodiment the PD-L3 modulator is a PD-L3 nucleic acid molecule. In another embodiment, the invention further provides treating the subject with an additional agent that modulates an immune response.

In still another embodiment, the invention provides a vaccine comprising an antigen and an agent that modulates (enhances or inhibits) PD-L3 activity. In a preferred embodiment, the vaccine inhibits the interaction between PD-L3 and its natural binding partner(s).

The present invention also provides diagnostic assays for identifying the presence or absence of a genetic alteration characterized by at least one of (i) aberrant modification or mutation of a gene encoding a PD-L3 polypeptide; (ii) misregulation of the gene; and (iii) aberrant post-translational modification of a PD-L3 polypeptide, wherein a wild-type form of the gene encodes a polypeptide with a PD-L3 activity.

In another aspect the invention provides methods for identifying a compound that binds to or modulates the activity of a PD-L3 polypeptide, by providing an indicator composition comprising a PD-L3 polypeptide having PD-L3 activity, contacting the indicator composition with a test compound, and determining the effect of the test compound on PD-L3 activity in the indicator composition to identify a compound that modulates the activity of a PD-L3 polypeptide.

In one aspect, the invention features a method for modulating the interaction of PD-L3 with its natural binding partner(s) on an immune cell comprising contacting an antigen presenting cell which expresses PD-L3 with an agent selected from the group consisting of: a form of PD-L3, or an agent that modulates the interaction of PD-L3 and its natural binding partner(s) such that the interaction of PD-L3 with it natural binding partner(s) on an immune cell is modulated. In a preferred embodiment, an agent that modulates the interaction of PD-L3 and its natural binding partner(s) is an antibody that specifically binds to PD-L3. In one embodiment, the interaction of PD-L3 with its natural binding partner(s) is upregulated. In another embodiment, the interaction of PD-L3 with its natural binding partner(s) is downregulated. In one embodiment, the method further comprises contacting the immune cell or the antigen presenting cell with an additional agent that modulates an immune response.

In one embodiment, the step of contacting is performed in vitro. In another embodiment, the step of contacting is performed in vivo. In one embodiment, the immune cell is selected from the group consisting of: a T cell, a monocyte, a macrophage, a dendritic cell, a B cell, and a myeloid cell.

In another aspect, the invention pertains to a method for inhibiting or increasing activation in an immune cell comprising increasing or inhibiting the activity or expression of PD-L3 in a cell such that immune cell activation is inhibited or increased.

In yet another aspect, the invention pertains to a vaccine comprising an antigen and an agent that inhibits the interaction between PD-L3 and its natural binding partner(s).

In still another aspect, the invention pertains to a vaccine comprising an antigen and an agent that promotes the interaction between PD-L3 and its natural binding partner(s).

In another aspect, the invention pertains to a method for treating a subject having a condition that would benefit from upregulation of an immune response comprising administering an agent that inhibits the interaction between PD-L3 and its natural binding partner(s) on cells of the subject such that a condition that would benefit from upregulation of an immune response is treated. In one embodiment, the agent comprises a blocking antibody or a small molecule that binds to PD-L3 and inhibits the interaction between PD-L3 and its natural binding partner(s). In another embodiment, the method further comprises administering a second agent that upregulates an immune response to the subject. In another aspect, the invention pertains to a method for treating a subject having a condition that would benefit from downregulation of an immune response comprising administering an agent that stimulates the interaction between PD-L3 and its natural binding partner(s) on cells of the subject such that a condition that would benefit from downregulation of an immune response is treated.

For example the condition treated with the PD-L3 protein or binding agents is selected from the group consisting of: a tumor, a pathogenic infection, an inflammatory immune response or condition, preferably less pronounced inflammatory conditions, or an immunosuppressive disease.

In one embodiment agent comprises an antibody or a small molecule that stimulates the interaction between PD-L3 and its natural binding partner(s). In another embodiment, the method further comprises administering a second agent that down-regulates an immune response to the subject.

Exemplary conditions treatable using PD-L3 proteins, binding agents or PD-L3 antagonists or agonists according to the invention include by way of example transplant, an allergy, infectious disease, cancer, and inflammatory or autoimmune disorders, e.g., an inflammatory immune disorder. Specific examples of the foregoing include type 1 diabetes, multiple sclerosis, rheumatoid arthritis, psoriatic arthritis, systemic lupus erythematosis, rheumatic diseases, allergic disorders, asthma, allergic rhinitis, skin disorders, gastrointestinal disorders such as Crohn's disease and ulcerative colitis, transplant rejection, poststreptococcal and autiommune renal failure, septic shock, systemic inflammatory response syndrome (SIRS), adult respiratory distress syndrome (ARDS) and envenomation; autoinflammatory diseases as well as degenerative bone and joint diseases including osteoarthritis, crystal arthritis and capsulitis and other arthropathies. Further, the methods and compositions can be used for treating tendonitis, ligamentitis and traumatic joint injury.

In another aspect, the invention pertains to a cell-based assay for screening for compounds which modulate the activity of PD-L3 comprising contacting a cell expressing a PD-L3 target molecule with a test compound and determining the ability of the test compound to modulate the activity of the PD-L3 target molecule In still another aspect, the invention pertains to a cell-free assay for screening for compounds which modulate the binding of PD-L3 to a target molecule comprising contacting a PD-L3 polypeptide or biologically active portion thereof with a test compound and determining the ability of the test compound to bind to the PD-L3 polypeptide or biologically active portion thereof.

In another embodiment, the invention pertains to a method of identifying a compound, e.g. an anti-PD-L3 antibody which modulates the effect of PD-L3 on T cell activation or cytokine production at a first and second antigen concentration comprising contacting a T cell expressing a PD-L3 target molecule with a test compound at a first antigen concentration, determining the ability of the test compound to modulate T cell proliferation or cytokine production at the first antigen concentration, contacting a T cell expressing a PD-L3 target molecule with the test compound at a second antigen concentration, and determining the ability of the test compound to modulate T cell proliferation or cytokine production at the second antigen concentration, thereby identifying a compound which modulates T cell activation or cytokine production at a first and second antigen concentration.

In other specific embodiments panels of anti-PD-L3 antibodies and PD-L3 proteins are screened to select those of which inhibit or promote the effects of PD-L3 on CD4+ and CD8+ T cell differentiation, proliferation and/or cytokine production in vitro or in vivo.

In preferred embodiments the subject PD-L3 proteins, nuclei acids, and ligands specific to PD-L3, preferably antibodies having desired effects on PD-L3 functions are used to treat conditions such a cancer, autoimmune diseases, allergy, inflammatory disorders or infection and more specifically immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias)

DETAILED DESCRIPTION OF THE DRAWINGS

Figure 1E:
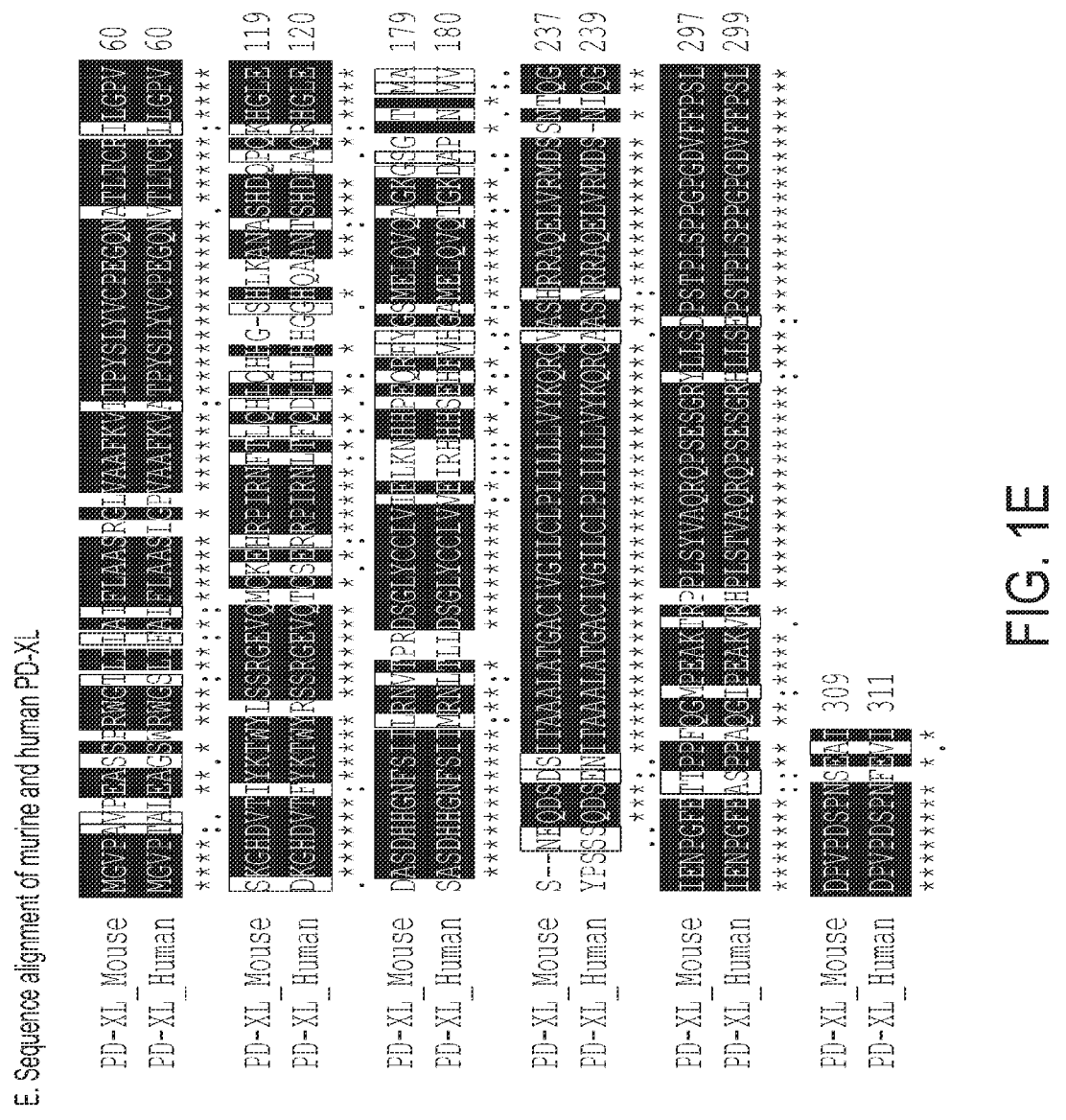

FIG. 1. Sequence analysis. A. Full length amino acid sequence of murine PD-L3. B. Amino acid sequence alignment of extracellular Ig domains between murine PD-L3 and selected B7 family ligands, including B7-H1 (PD-L1), B7-DC (PD-L2), B7-H3, and B7-H4. C Alignment of PD-L31 g domain with B7 family receptors, including PD-1, CTLA-4, CD28, BTLA, and ICOS. Ig-v domain, " . . . "; Ig-c domain, "_". Alignment was performed using the MUSCLE algorithm (MUltiple Sequence Comparison by Log-Expectation). D. Sequence identity (%) of the Ig-V domains between PD-L3 and other B7 family ligands and receptors is calculated using ClustalW2 program. E. Sequence homology between human and murine PD-L3. Identical residues are shaded in black. Highly conserved and semi-conserved residues are shaded in dark and light shade of gray respectively.

Figure 2:
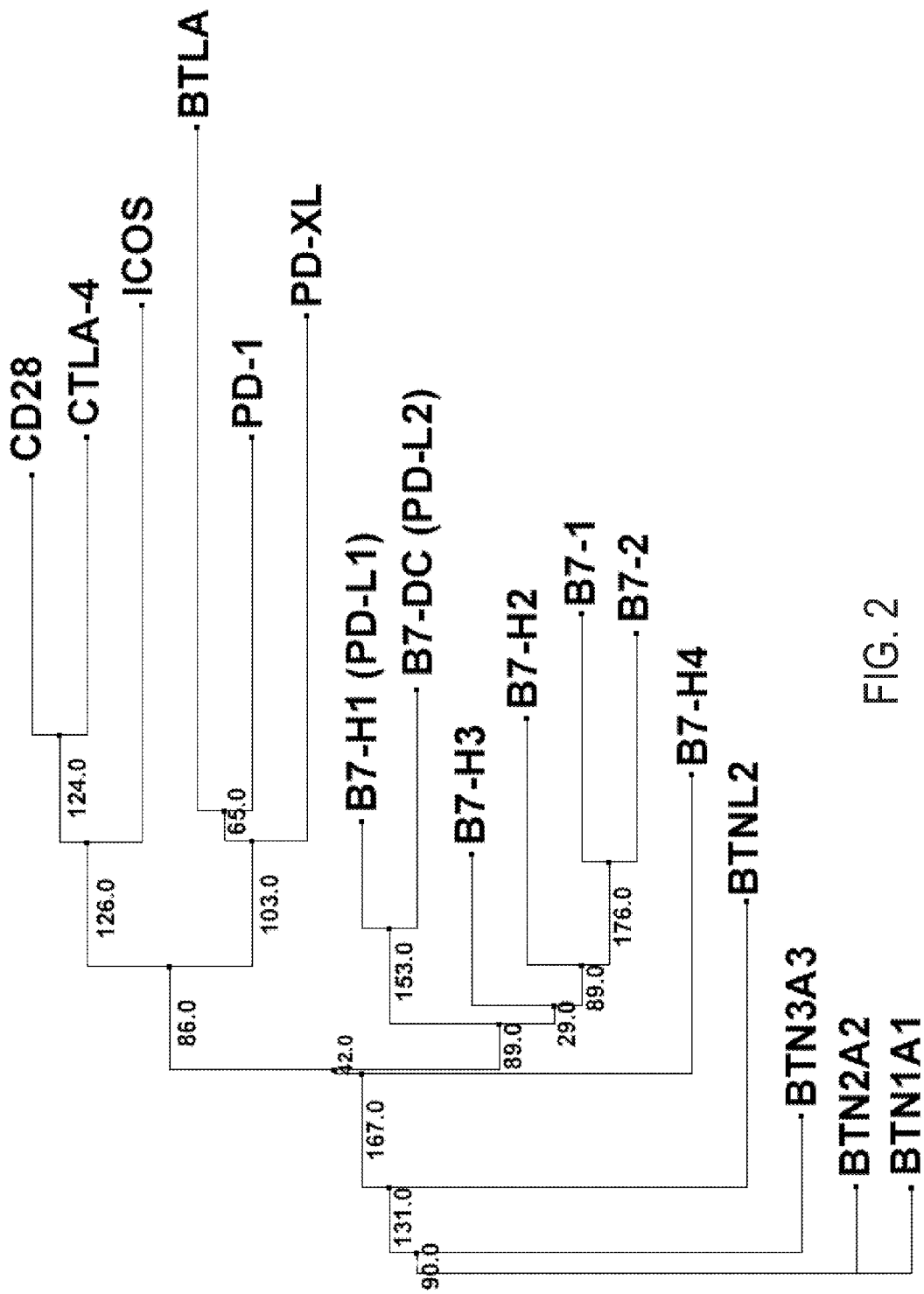

FIG. 2. Phylogenic analysis of mouse PD-L3 with other Immunoglobulin (Ig) superfamily members. Full-length sequence of mouse PD-L3 and other Ig superfamily members, including CD28, CTLA-4, ICOS, BTLA, PD-1, B7-H1 (PD-L1), B7-DC (PD-L2), B7-H2, B7-H3, B7-H4, B7-1, B7-2, BTNL2, BTN3A3, BTN2A2, and BTN1A1, were analyzed using PhyML algorithm (Phylogenetic Maximum Likelihood). Branch distances were shown at tree branch joints.

FIG. 3. Tissue expression and hematopoietic cell expression patterns of PD-L3 A. RT-PCR of full length PD-L3 from mouse tissues. Lanes: (1) muscle (2) heart (3) eye (4) thymus (5) spleen (6) small intestine (7) kidney (8) liver (9) brain (10) mammary gland (11) lung (12) ovary (13) bone marrow. B. RT-PCR of full-length PD-L3 from purified hematopoietic cell types. Lanes (1) peritoneal macrophages (2) splenic CD11b+ monocytes (3) splenic CD11c+DCs (4) splenic CD4+ T cells (5) splenic CD8+ T cells (6) splenic B cells. C-E. Flow cytometry analysis of PD-L3 expression on splenic CD4+ and CD8+ T cells from thymus and spleen (C), on CD11b+ monocytes (D), and on CD11c+DC subsets from spleen and peritoneal cavity (E). F. Splenic B cells, NK cells and granulocytes are also analyzed. G. The differential expression of PD-L3 on hematopoietic cells from different tissue sites, including mesenteric LN, peripheral LN, spleen, blood and peritoneal cavity. Representative data from at least 3 independent experiments are shown.

FIG. 4. Gene array data of PD-L3 from the GNF (Genomics Institute of Novartis Research Foundation) gene array database, as well as the NCBI GEO (gene expression omnibus) database.

Figure 5:
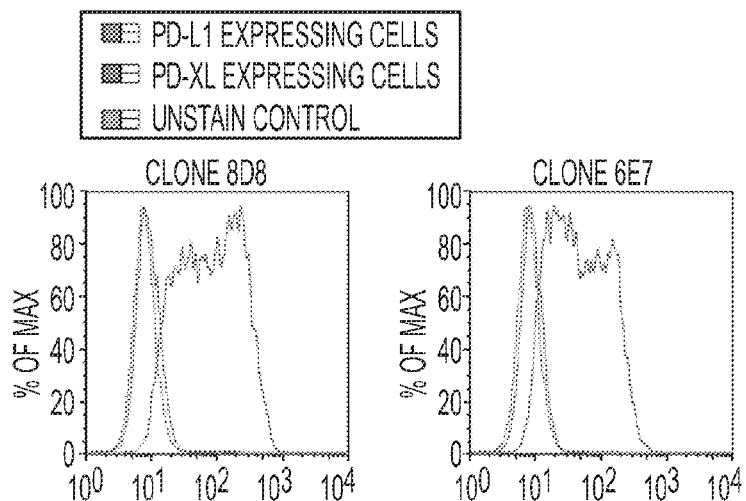

FIG. 5. Specificity of PD-L3 hamster monoclonal antibodies. Mouse EL4 cell lines over-expressing either PD-L1 or PD-L3 fused to RFP were stained using the supernatants from hybridoma cultures and analyzed by flow cytometry. Two representative positive clones are shown.

Figure 6:
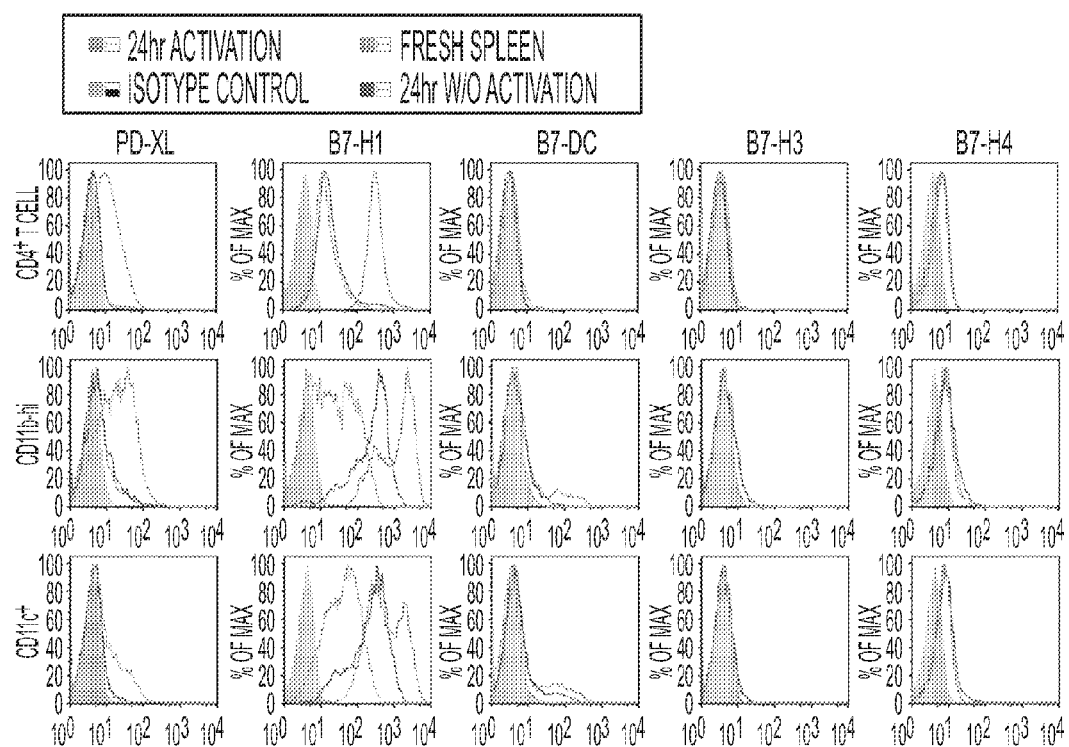

FIG. 6. Comparison of PD-L3 expression with other B7 family ligands on in vitro cultured spleen cells. Expression of PD-L3 and other B7 family ligands (i.e. PD-L1, PD-L2, B7-H3, and B7-H4) on hematopoietic cell types, including CD4+ T cells, CD11bhi monocytes, and CD11c+DCs were compared. Cells were either freshly isolated, or in vitro cultured for 24 hrs, with and without activation. CD4+ T cells were activated with plate-bound CD3 (5 ug/ml), CD11bhi monocytes and CD11c+DCs were activated with IFN (20 ng/ml) and LPS (200 ng/ml). Representative results from three independent experiments are shown.

FIG. 7. Comparison of in vivo expression patterns of PD-L3 and other B7 family ligands during immunization. DO11.10 TCR transgenic mice were immunized with chicken ovalbumin (OVA) emulsified in complete Freund's adjuvant (CFA) on the flank. Draining and non-draining lymph node cells were collected 24 hr post immunization, and analyzed by flow cytometry for the expression of PD-L3, PD-L1 and PD-L2. Shown are representative results from at least four independent experiments. A. A population of CD11b+ cells expressing a high level of PD-L3 was induced at 24 hr post immunization with CFA/OVA, but not with CFA alone within the draining lymph node. These cells are of mixed phenotype of F4/80+ macrophages and CD11C+ dendritic cells. B. Expression of PD-L3, PD-L1 and PD-L2 on CD11bhi monocytes, CD11c+DCs and CD4+ T cells were analyzed at 24 hr post immunization.

Figure 8:
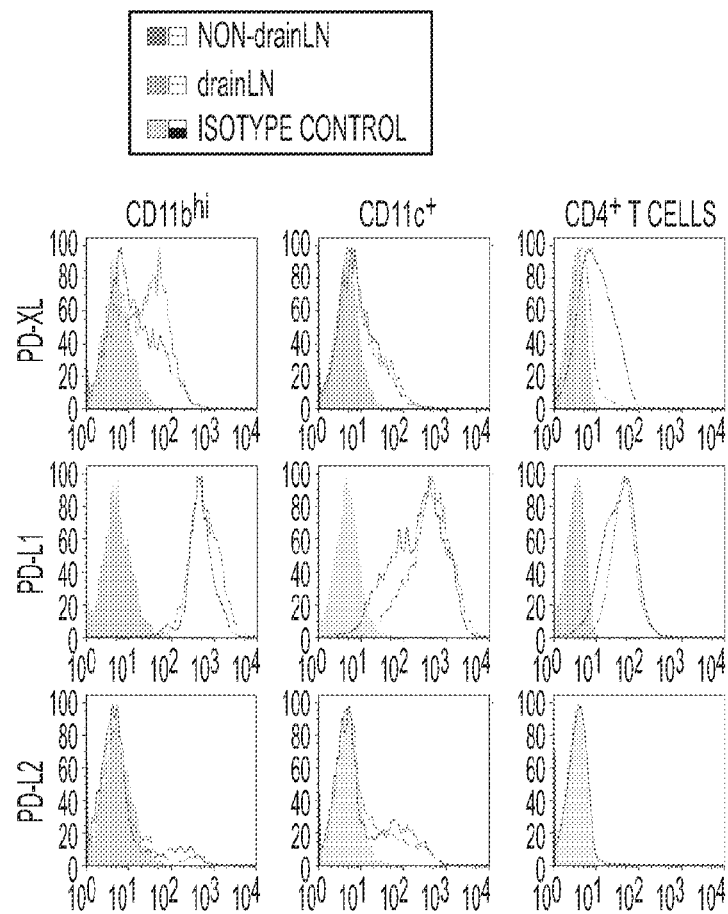

FIG. 8 Loss of PD-L3 expression on activated CD4+ T cells in response to immunization. DO11.10 mice were immunized with chicken ovalbumin (OVA) emulsified in complete Freund's adjuvant (CFA) on the flank. Draining and non-draining lymph node cells were collected 48 hr post immunization, and analyzed for PD-L3 expression by flow cytometry. Shown are representative results from 2 independent experiments.

FIG. 9. Immobilized PD-L3-Ig fusion protein inhibited CD4+ and CD8+ T cell proliferation. A. CFSE labeled CD4+ and CD8+ T cells were stimulated by plate-bound CD3 with or without co-absorbed PD-L3-Ig. The percentage of CFSE-low cells was quantified and shown in B. C CD4+ T cells from PD-1 ko mice were also suppressed by PD-L3-Ig. D. PD-L3-Ig-mediated suppression is persistent and can act late. CD4+ T cells were activated in the presence of PD-L3-Ig or control-Ig for either 72 hrs (i), or for 24 hrs (ii, iii and iv). 24 hr-preactivated cells were harvested and re-stimulated under specified conditions for another 48 hrs. Cell proliferation was analyzed at the end of the 72 hr culture. (ii) Pre-activation with PD-L3-Ig and re-stimulation with antiCD3; (iii) Pre-activation with antiCD3 and re-stimulation with PD-L3-Ig. (iv) Pre-activation with PD-L3-Ig and re-stimulation with PD-L3-Ig. Duplicated wells were analyzed for all conditions. Shown are representative results from at least four experiments.

Figure 10:
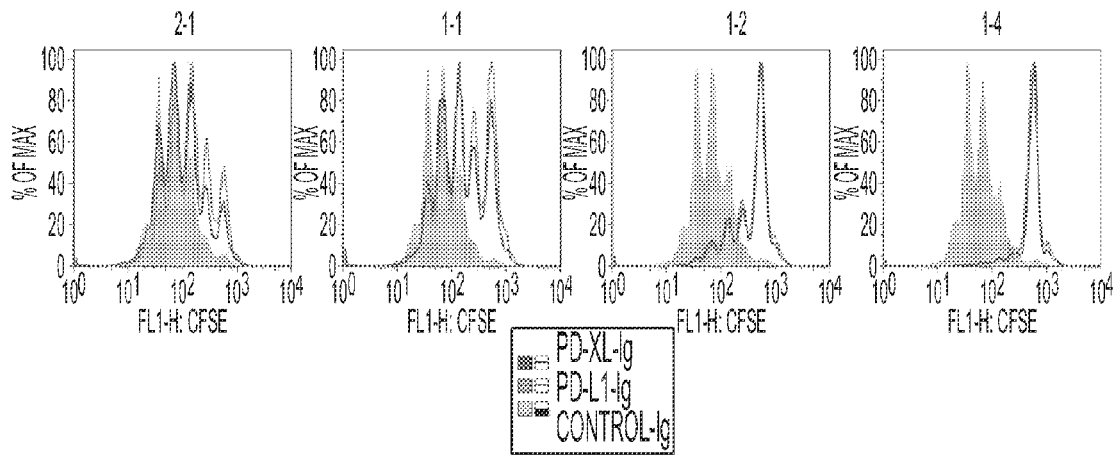

FIG. 10. Similar inhibitory effect of PD-L1-Ig and PD-L3-Ig fusion proteins on CD4+ T cell proliferation. Bulk purified CD4+ T cells were CFSE labeled and stimulated with plate-bound CD3 together with titrated amount of PD-L1-Ig or PD-L3-Ig fusion proteins. CFSE dilution was analyzed at 72 hrs and the percentage of CFSElow cells was quantified. Duplicated wells were analyzed for all conditions. Shown are representative results from 2 independent experiments.

Figure 11A:
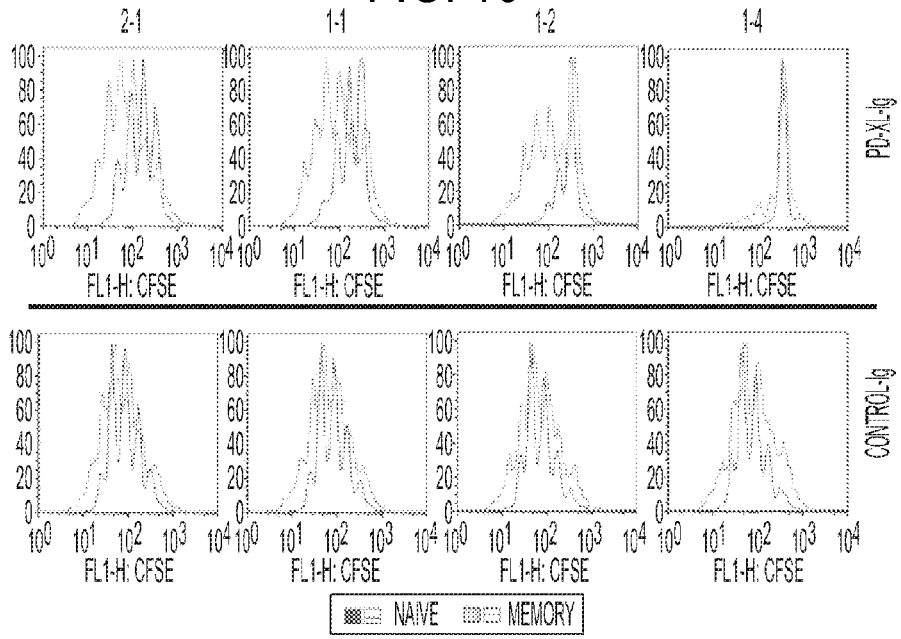
Figure 11B:
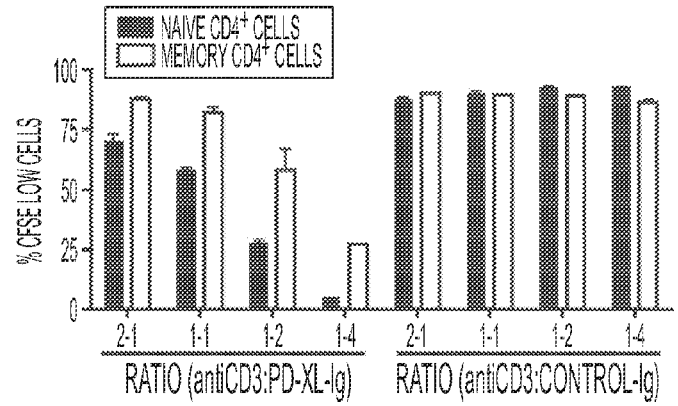

FIG. 11. Suppressive impact of PD-L3-Ig on the proliferation of naïve and memory CD4+ T cells. A. Naïve (CD25-CD44lowCD62Lhi) and memory (CD25-CD44hiCD62Llow) CD4+ T cell subsets were sorted, CFSE labeled, and stimulated with plate-bound anti-CD3 (2.5 µg/ml) together with PD-L3-Ig or control-Ig at indicated ratios. Cell proliferation was analyzed at 72 hrs by examining the CFSE division profile. The percentage of proliferated cells, as determined by percentage of CFSElow cells, is calculated and shown in B. Duplicated wells were analyzed for all conditions. Shown are representative results from two independent experiments.

Figure 12A:
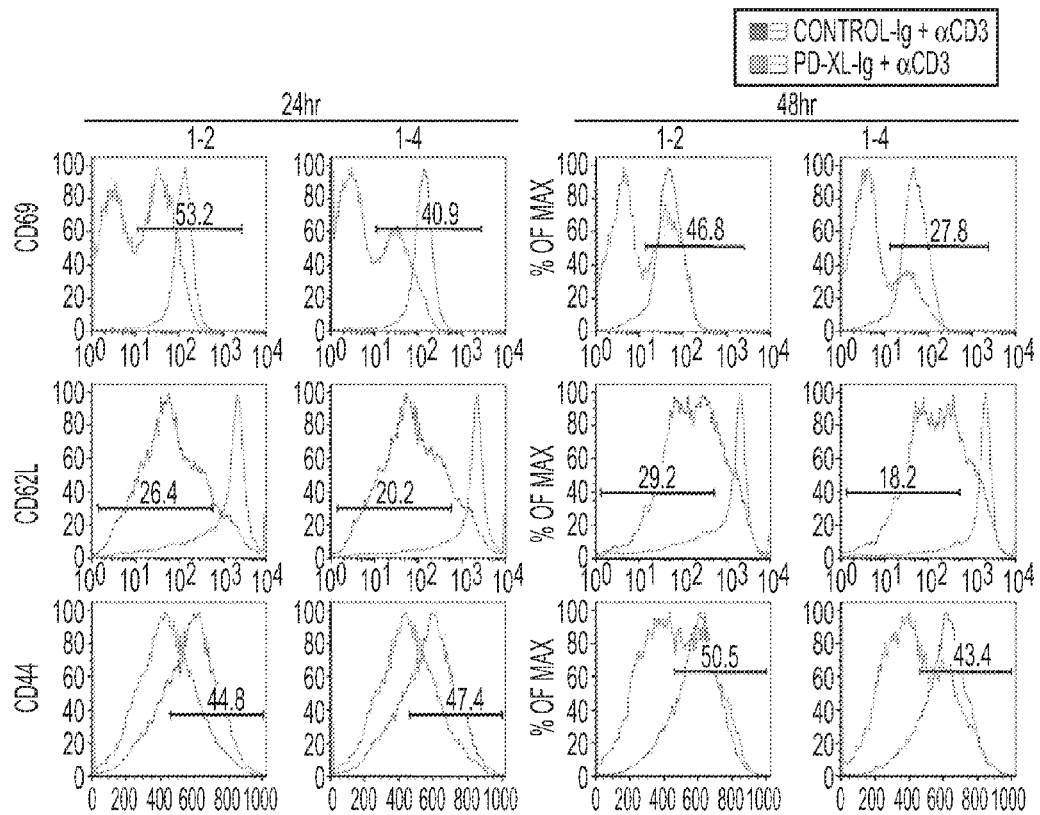

FIG. 12. PD-L3-Ig fusion protein suppressed early TCR activation and cell proliferation, but did not directly induce apoptosis. Bulk purified CD4+ T cells were stimulated with plate-bound anti-CD3 together with PD-L3-Ig or control-Ig at 1-2 ratio (2.5 µg/ml and 5 µg/ml respectively). Cells were analyzed at 24 hr and 48 hrs for the expression of CD69, CD62L, and CD44 by flow cytometry. Cells were also stained for early apoptosis marker annexin-V, and cell death marker 7-Aminoactinomycin D (7-AAD). Shown are representative results from two independent experiments.

FIG. 13. PD-L3-Ig inhibited cytokine production by CD4+ and CD8+ T cells. A-B. Bulk purified CD4+ T cells were stimulated with plate-bound anti-CD3, and PD-L3-Ig or control-Ig at stated ratios. Culture supernatants were collected after 24 hrs and 48 hrs. Levels of IL-2 and IFN were analyzed by ELISA. C-D. CD4+ T cells were sorted into naïve (CD25-CD44lowCD62Lhi) and memory (CD25-CD44hiCD62Llow) cell populations. Cells were stimulated with plate-bound CD3 and PD-L3-Ig or control-Ig at a ratio of 1:2. Culture supernatants were collected at 48 hrs and analyzed for the level of IL-2 and IFN by ELISA. E. Bulk purified CD8+ T cells were stimulated with plate-bound CD3, and PD-L3-Ig or control-Ig at indicated ratios. IFN in the culture supernatant was analyzed by ELISA. For all conditions, supernatant for six duplicated wells were pooled for ELISA analysis. Shown are representative results from at least three experiments.

FIG. 14. PD-L3-Ig-mediated suppression could overcome a moderate level of costimulation provided by CD28, but was completely reversed by a high level of costimulation, as well as partially rescued by exogenous IL-2. A-B. CD4+ T cells were activated by plate-bound CD3 together with either PD-L3-Ig or control-Ig at 1-1 ratio and 1-2 ratios. For cytokine rescue, soluble mIL-2, mIL7, mIL15 and mIL-23 (all at 40 ng/ml) were added to the cell culture (A). To examine the effects of costimulation, CD28 (1 µg/ml) was immobilized together with CD3 and Ig proteins at indicated ratios (B). Cell proliferation was analyzed at 72 hr by examining CFSE division profiles. C-D. To examine the suppressive activity of PD-L3 in the presence of lower levels of costimulation, titrated amounts of CD28 were coated together with anti-CD3 (2.5 µg/ml) and PD-L3-Ig fusion proteins or control-Ig fusion protein (10 µg/ml) to stimulate CD4+ T cell proliferation. Cell proliferation was analyzed at 72 hr. Percentages of proliferated CFSElow cells were quantified and shown in D. Duplicated wells were analyzed for all conditions. Representative CFSE profiles from three independent experiments are shown.

FIG. 15. PD-L3 expressed on antigen presenting cells suppressed CD4 T cell proliferation. A-C The CHO cell line that stably expresses MHCII molecule I-Ad and costimulation molecule B7-2 was used as the parent cell line. Cells were transduced with retrovirus expressing either PD-L3-RFP or RFP control molecules. Transduced cells were sorted to achieve homogenous level of expression. To test their ability as antigen presenting cells, CHO-PD-L3 or CHO-RFP cells were mitomycin C treated and mixed with OVA-specific transgenic CD4+ T cells DO11.10, in the presence of titrated amount of OVA peptide. Proliferation of DO11 cells was analyzed at 72 hrs, either by CFSE division profiles (A-B), or by tritium incorporation (C). D. bone marrow derived dendritic cells were transduced with RFP or B7B-H5-RFP retrovirus during 10-day culture period. Transduced CD11c+ RFP+ DCs and non-transduced CD11c+ RFP− DCs were sorted and used to stimulate OVA-specific transgenic CD4+ T cells OTII in the presence of titrated amount of OVA peptide. Cell proliferation was analyzed on day 3 by examining CFSE division. For all experiments, duplicated wells were analyzed for all conditions, and representative results from three independent experiments are shown.

Figure 16:
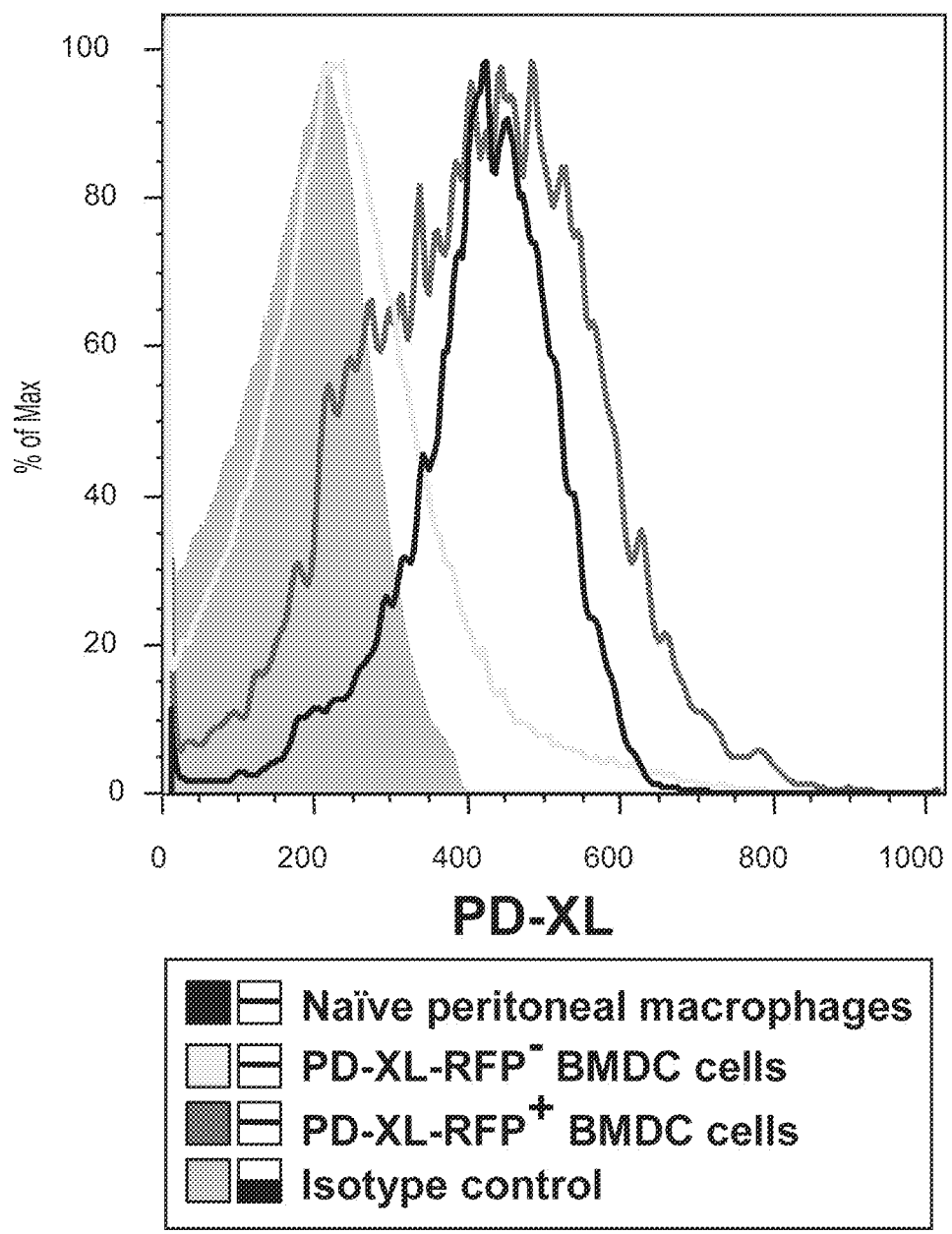

FIG. 16. Surface expression level of PD-L3 in retrovirally transduced bone marrow derived DCs. Bone marrow derived DCs (BMDC) were cultured in the presence of GM-CSF (20 ng/mml) and transduced with either RFP or PD-L3-RFP retrovirus as described in Methods. On day 10, surface expression level of PD-L3 were analyzed on cultured BMDCs, and compared to freshly-isolated peritoneal macrophages.

Figure 17:
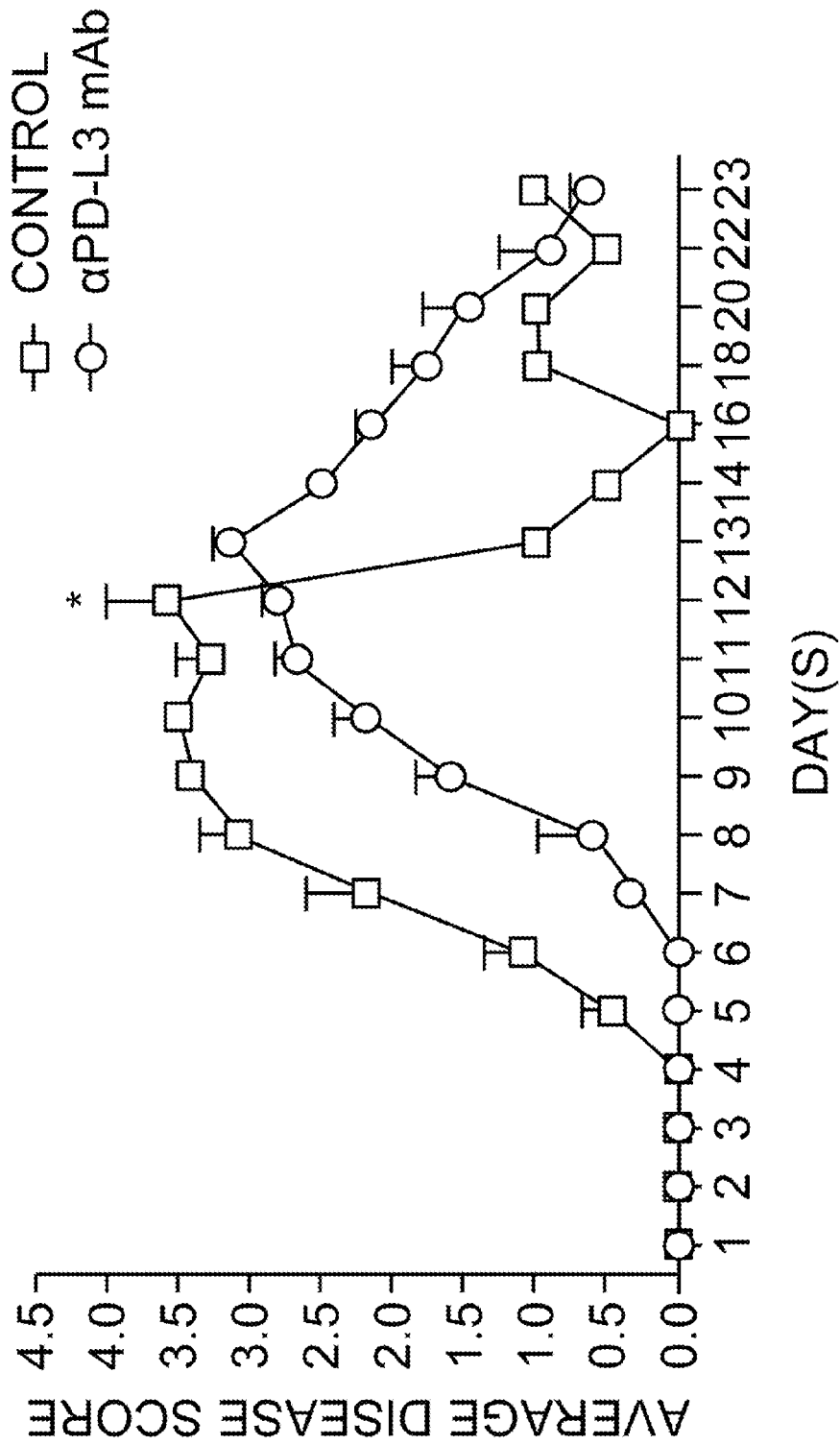

FIG. 17 shows that anti-PDL3 mAb exhibits efficacy in a passive transfer EAE model. In this adoptive transfer EAE model, donor SJL mice were immunized with CFA and PLP peptide. On day 10, total lymphocytes from draining LN were isolated, and cultured in vitro with PLP peptide, IL-23 (20 ng/ml) and anti-IFNg (10 µg/ml) for 4 days. Expanded CD4 T cells were then purified and adoptively transferred into naïve recipient mice. Disease progression was monitored and scored with: 0, no disease; 0.5 loss of tail tone; 1: limp tail; 2: limp tail+hind limb paresis; 2.5: 1 hind limb paralysis; 3: both hind limb paralysis; 3.5: forelimb weakness; 4: hind limb paralysis+ unilateral forelimb paralysis. Mice were sacrificed when disease score reached 4. *, mice were sacrificed.

Figure 18:
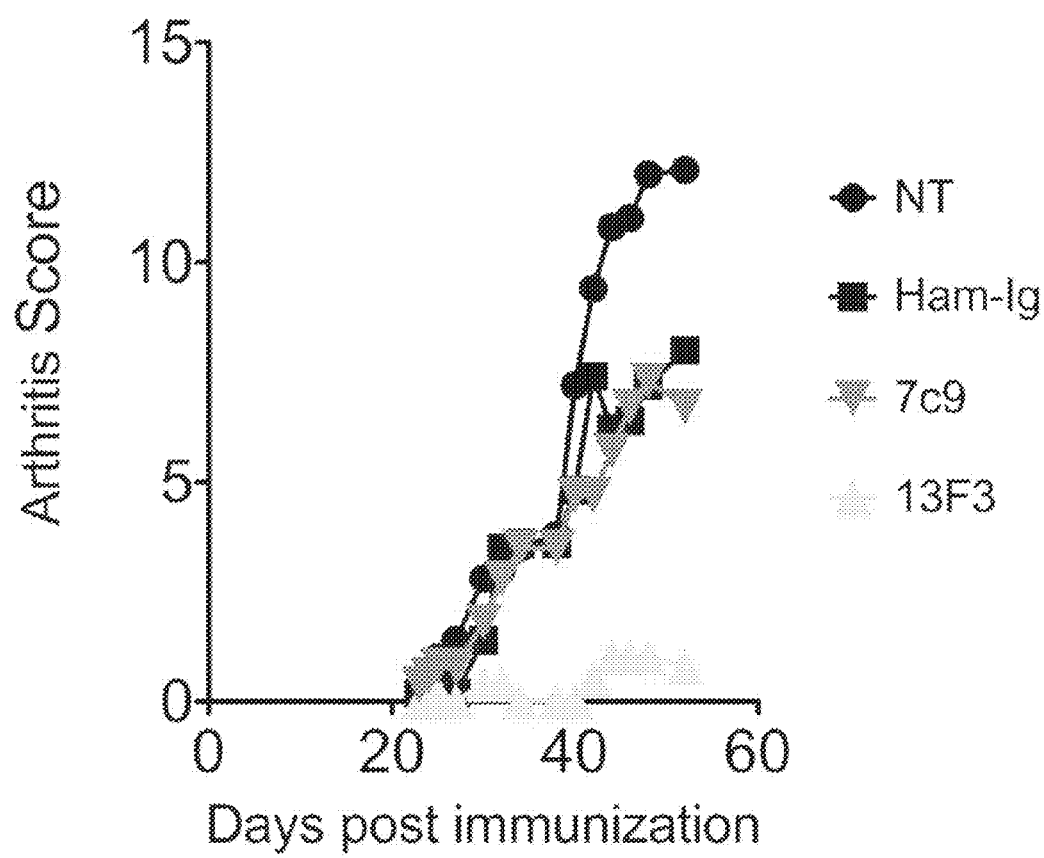

FIG. 18 shows than anti-PD-L3 antibodies exhibit efficacy (reduce symptoms of arthritis) in a collagen-induced arthritis animal model.

DETAILED DESCRIPTION OF THE INVENTION

Definitions

Prior to describing the invention in more detail the following definitions are provided.

As used herein, the term "immune cell" includes cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

As used herein, the term "T cell" includes CD4+ T cells and CD8+ T cells. The term T cell also includes both T helper 1 type T cells and T helper 2 type T cells.

The term "antigen presenting cell" includes professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "immune response" includes T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

As used herein, the term "costimulatory receptor" includes receptors which transmit a costimulatory signal to an immune cell, e.g., CD28 or ICOS. As used herein, the term "inhibitory receptors" includes receptors which transmit a negative signal to an immune cell As used herein, the term "costimulate", with reference to activated immune cells, includes the ability of a costimulatory molecule to provide a second, non-activating, receptor-mediated signal (a "costimulatory signal") that induces proliferation or effector function. For example, a costimulatory signal can result in cytokine secretion, e.g., in a T cell that has received a T cell-receptor-mediated signal. Immune cells that have received a cell receptor-mediated signal, e.g., via an activating receptor, are referred to herein as "activated immune cells."

An inhibitory signal as transduced by an inhibitory receptor can occur even if a costimulatory receptor (such as CD28 or ICOS) in not present on the immune cell and, thus, is not simply a function of competition between inhibitory receptors and costimulatory receptors for binding of costimulatory molecules (Fallarino et al. (1998) J. Exp. Med. 188:205). Transmission of an inhibitory signal to an immune cell can result in unresponsiveness, anergy or programmed cell death in the immune cell. Preferably, transmission of an inhibitory signal operates through a mechanism that does not involve apoptosis.

As used herein the term "apoptosis" includes programmed cell death which can be characterized using techniques which are known in the art. Apoptotic cell death can be characterized, e.g., by cell shrinkage, membrane blebbing, and chromatin condensation culminating in cell fragmentation. Cells undergoing apoptosis also display a characteristic pattern of internucleosomal DNA cleavage.

Depending upon the form of the PD-L3 molecule that binds to a receptor, a signal can be either transmitted (e.g., by a multivalent form of a PD-L3 molecule that results in crosslinking of the receptor or by a soluble form of PD-L3 that binds to Fc receptors on antigen presenting cells) or inhibited (e.g., by a soluble, monovalent form of a PD-L3 molecule or a soluble form of PD-L3 that is altered using methods known in the art such that it does not bind to Fc receptors on antigen presenting cells), e.g., by competing with activating forms of PD-L3 molecules for binding to the receptor. However, there are instances in which a soluble molecule can be stimulatory. The effects of the various modulatory agents can be easily demonstrated using routine screening assays as described herein.

As used herein, the term "activating receptor" includes immune cell receptors that bind antigen, complexed antigen (e.g., in the context of MHC molecules), or antibodies. Such activating receptors include T cell receptors (TCRs), B cell receptors (BCRs), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g, protein phosphorylation, membrane lipid changes, ion fluxes, cyclic nucleotide alterations, RNA transcription changes, protein synthesis changes, and cell volume changes.

The term "B cell receptor" (BCR) as used herein includes the complex between membrane Ig (mIg) and other transmembrane polypeptides (e.g., Ig alpha and Ig beta) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

The term "Fc receptor" (FcRs) include cell surface receptors for the Fc portion of immunoglobulin molecules (Igs). Fc receptors are found on many cells which participate in immune responses. Among the human FcRs that have been identified so far are those which recognize IgG (designated Fc gamma. R), IgE (Fc epsilon R1), IgA (Fc alpha R), and polymerized IgM/A (Fc.mu. .alpha. R). FcRs are found in the following cell types: Fc epsilon R I (mast cells), Fc epsilon. RII (many leukocytes), Fc alpha. R (neutrophils), and Fc mu alpha. R (glandular epithelium, hepatocytes) (Hogg, N. (1988) Immunol. Today 9:185-86). The widely studied Fc gamma Rs are central in cellular immune defenses, and are responsible for stimulating the release of mediators of inflammation and hydrolytic enzymes involved in the pathogenesis of autoimmune disease (Unkeless, J. C (1988) Annu. Rev. Immunol. 6:251-87). The Fc gammaRs provide a crucial link between effector cells and the lymphocytes that secrete Ig, since the macrophage/monocyte, polymorphonuclear leukocyte, and natural killer (NK) cell Fc gamma Rs confer an element of specific recognition mediated by IgG. Human leukocytes have at least three different receptors for IgG: h Fc gamma. R1 (found on monocytes/macrophages), hFc gamma RII (on monocytes, neutrophils, eosinophils, platelets, possibly B cells, and the K562 cell line), and Fc.gamma. III (on NK cells, neutrophils, eosinophils, and macrophages).

With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor molecule on an immune cell. Such a signal antagonizes a signal via an activating receptor (e.g., via a TCR, CD3, BCR, or Fc molecule) and can result, e.g., in inhibition of: second messenger generation; proliferation; or effector function in the immune cell, e.g., reduced phagocytosis, antibody production, or cellular cytotoxicity, or the failure of the immune cell to produce mediators (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or high doses of antigen.

As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

Modulation of a costimulatory signal results in modulation of effector function of an immune cell. Thus, the term "PD-L3 activity" includes the ability of a PD-L3 polypeptide to bind its natural binding partner(s), the ability to modulate immune cell costimulatory or inhibitory signals, and the ability to modulate the immune response.

Modulation of an inhibitory signal in an immune cell results in modulation of proliferation of and/or cytokine secretion by an immune cell.

As used herein, a "naturally-occurring" nucleic acid molecule refers to an RNA or DNA molecule having a nucleotide sequence that occurs in nature (e.g., encodes a natural protein).

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

An "isolated" or "purified" protein or biologically active portion thereof is substantially free of cellular material or other contaminating proteins from the cell or tissue source from which the PD-L3 protein is derived, or substantially free from chemical precursors or other chemicals when chemically synthesized. The language "substantially free of cellular material" includes preparations of PD-L3 protein in which the protein is separated from cellular components of the cells from which it is isolated or recombinantly produced. In one embodiment, the language "substantially free of cellular material" includes preparations of PD-L3 protein having less than about 30% (by dry weight) of non-PD-L3 protein (also referred to herein as a "contaminating protein"), more preferably less than about 20% of non-PD-L3 protein, still more preferably less than about 10% of non-PD-L3 protein, and most preferably less than about 5% non-PD-L3 protein. When the PD-L3 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PD-L3 protein in which the protein is separated from chemical precursors or other chemicals which are involved in the synthesis of the protein. In one embodiment, the language "substantially free of chemical precursors or other chemicals" includes preparations of PD-L3 protein having less than about 30% (by dry weight) of chemical precursors or non-PD-L3 chemicals, more preferably less than about 20% chemical precursors or non-PD-L3 chemicals, still more preferably less than about 10% chemical precursors or non-PD-L3 chemicals, and most preferably less than about 5% chemical precursors or non-PD-L3 chemicals.

The term "antibody", as used herein, includes an "antigen-binding portion" of an antibody (or simply "antibody portion"), as well as whole antibody molecules. The term "antigen-binding portion", as used herein, refers to one or more fragments of an antibody that retain the ability to specifically bind to an antigen (e.g, PD-L3). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al. (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc Natl. Acad. Sci. USA 85:5879-5883; and Osbourn et al. 1998 Nat. Biotechnol. 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and Vl can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) Proc Natl. Acad. Sci. USA 90:6444-6448; Poljak, R. J. et al. (1994) Structure 2:1121-1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M. et al. (1995) Hum. Antibodies Hybridomas 6:93-101) and use of a cysteine residue, a marker peptide and a C-terminal polyhistidine tag to make bivalent and biotinylated scFv molecules (Kipriyanov, S. M. et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g., humanized, chimeric, etc Preferably, antibodies of the invention bind specifically or substantially specifically to PD-L3 molecules. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds PD-L3 is substantially free of antibodies that specifically bind antigens other than PD-L3). Moreover, an isolated antibody may be substantially free of other cellular material and/or chemicals.

PD-L3 Nucleic Acid and Polypeptide Molecules

The term "family" when referring to the polypeptide and nucleic acid molecules of the invention is intended to mean two or more polypeptide or nucleic acid molecules having a common structural domain or motif and having sufficient amino acid or nucleotide sequence homology as defined herein. Such family members can be naturally or non-naturally occurring and can be from either the same or different species. For example, a family can contain a first polypeptide of human origin, as well as other, distinct polypeptides of human origin or alternatively, can contain homologues of non-human origin, e.g., monkey polypeptides. Members of a family may also have common functional characteristics.

For example, the family of PD-L3 polypeptides of the present invention preferably comprises least one "signal peptide domain". As used herein, a "signal sequence" or "signal peptide" includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., Valine, Leucine, Isoleucine or Phenylalanine). Such a "signal sequence", also referred to in the art as a "signal peptide", serves to direct a polypeptide containing such a sequence to a lipid bilayer, and is cleaved in secreted and membrane bound polypeptides. As described infra a signal sequence was identified in the amino acid sequence of native human PD-L3 and was also identified in the amino acid sequence of native mouse PD-L3

In another embodiment of the invention, a PD-L3 polypeptide of the present invention is identified based on the presence of a "transmembrane domain". As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19:235-263, the contents of which are incorporated herein by reference. The transmembrane domain region of PDL3 are identified herein (see e.g., FIG. 1).

In another embodiment, a PD-L3 molecule of the present invention is identified based on the absence of an "IgC domain" and the presence of an "IgV domain" in the polypeptide or corresponding nucleic acid molecule. As used herein, IgV and IgC domains are recognized in the art as Ig superfamily member domains. These domains correspond to structural units that have distinct folding patterns called Ig folds. Ig folds are comprised of a sandwich of two beta sheets, each consisting of antiparallel beta strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of beta strands. The amino acid residues of the native human and murine PD-L3 polypeptide, constituting the IgV domain can be seen in FIG. 1. The presence of an IgV domain is likely required for binding of PD-L3 to its natural binding partner(s)

In another embodiment, a PD-L3 molecule of the present invention is identified based on the presence of a "extracellular domain" in the polypeptide or corresponding nucleic acid molecule. As used herein, the term "extracellular domain" represents the N-terminal amino acids which extend as a tail from the surface of a cell. An extracellular domain of the present invention includes an IgV domain and may include a signal peptide domain. (See FIG. 1).

In still another embodiment, a PD-L3 molecule of the present invention is identified based on the presence of a "cytoplasmic domain" in the polypeptide or corresponding nucleic acid molecule. As used herein, the term "cytoplasmic domain" represents the C-terminal amino acids which extend as a tail into the cytoplasm of a cell. predicted to comprise cytoplasmic domains.

In a preferred embodiment, the PD-L3 molecules of the invention include at least one or more of the following domains: a signal peptide domain, an IgV domain, an extracellular domain, a transmembrane domain, and a cytoplasmic domain.

Isolated polypeptides of the present invention, preferably PD-L3 polypeptides, have an amino acid sequence sufficiently identical to the amino acid sequence of SEQ ID NO: 2 or 4, or 5 or are encoded by a nucleotide sequence sufficiently identical to SEQ ID NO: 1 or 3 or fragment or complement thereof. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% homology and share a common functional activity are defined herein as sufficiently identical.

As used interchangeably herein, "PD-L3 activity", "biological activity of PD-L3" or "functional activity of PD-L3", refers to an activity exerted by a PD-L3 protein, polypeptide or nucleic acid molecule on a PD-L3-responsive cell or tissue, or on a PD-L3 polypeptide binding partner, as determined in vivo, or in vitro, according to standard techniques. These activities include modulating CD4+ and CD8+ T cell proliferation and cytokine production. In another embodiment, a PD-L3 activity is a direct activity, such as an association with a PD-L3 binding partner. As used herein, a "target molecule" or "binding partner" is a molecule with which a PD-L3 polypeptide binds or interacts in nature, i.e., expressed on a T cell, such that PD-L3-mediated function is achieved. Alternatively, a PD-L3 activity is an indirect activity, such as a cellular signaling activity mediated by the PD-L3 polypeptide. The biological activities of PD-L3 are described herein. For example, the PD-L3 polypeptides and PD-L3 agonists or antagonists of the present invention can have one or more of the following activities: (1) suppresses or promotes CD4+ and CD8+ T cell proliferation, (2) suppresses or promotes cytokine production (3) functions as a regulatory ligand that negatively regulates T cell responses during cognate interactions between T cells and myeloid derived APCs (4) negatively regulates CD4+ T cell responses by suppressing early TCR activation and arresting cell division, but with minimum direct impact on apoptosis, (5) suppresses or promotes antigen-specific T cell activation during cognate interactions between APCs and T cells and/or (6) suppresses or promotes T cell-mediated immune responses; (7) modulate activation of immune cells, e.g., T lymphocytes, and (8) modulate the immune response, e.g., inflammatory immune response of an organism, e.g., a mouse or human organism.

Accordingly, another embodiment of the invention features isolated PD-L3 proteins and polypeptides that modulate one or more PD-L3 activities. These polypeptides will include PD-L3 polypeptides having one or more of the following domains: a signal peptide domain, an IgV domain, an extracellular domain, a transmembrane domain, and a cytoplasmic domain, and, preferably, a PD-L3 activity.

Additional preferred PD-L3 polypeptides may have at least one extracellular domain, and one or more of a signal peptide domain, an IgV domain, an transmembrane domain, and a cytoplasmic domain, and are, preferably, encoded by a nucleic acid molecule having a nucleotide sequence which hybridizes under stringent hybridization conditions to a nucleic acid molecule comprising a complement of the nucleotide sequence of SEQ ID NO: 1 or 3 herein. The nucleotide and amino acid sequences sequence of the exemplified isolated human and murine PD-L3 cDNA and the predicted amino acid sequence of the human PD-L3 polypeptide are contained in the sequence listing herein.

Various aspects of the invention are described in further detail in the following subsections:

I. PD-L3 Isolated Nucleic Acid Molecules

One aspect of the invention pertains to isolated nucleic acid molecules that encode PD-L3 polypeptides or biologically active portions thereof, as well as nucleic acid fragments sufficient for use as hybridization probes to identify PD-L3-encoding nucleic acid molecules (e.g., PD-L3 mRNA) and fragments for use as PCR primers for the amplification or mutation of PD-L3 nucleic acid molecules. As used herein, the term "nucleic acid molecule" is intended to include DNA molecules (e.g, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, in various embodiments, the isolated PD-L3 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention, e.g., a nucleic acid molecule having the nucleotide sequence of SEQ ID NO: 1, 3, or a portion thereof, can be isolated using standard molecular biology techniques and the sequence information provided herein. Using all or portion of the nucleic acid sequence of SEQ ID NO: 1, 3, 4, or 6 as a hybridization probe, PD-L3 nucleic acid molecules can be isolated using standard hybridization and cloning techniques (e.g., as described in Sambrook, J. et al. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 1, 3, or an ortholog or variant can be isolated by the polymerase chain reaction (PCR) using synthetic oligonucleotide primers designed based upon the sequence of SEQ ID NO: 1, 2, 3, 4 or 5.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to PD-L2 nucleotide sequences can be prepared by standard synthetic techniques, e.g., using an automated DNA synthesizer.

In a preferred embodiment, an isolated PD-L3 encoding nucleic acid molecule of the invention comprises the nucleotide sequence shown in SEQ ID NO: 1, or 3, or a fragment thereof. In another embodiment the nucleic acid molecule of the invention comprises a nucleic acid molecule which is a complement of the nucleotide sequence shown in SEQ ID NO: 1, or 3, or a portion of any of these nucleotide sequences. A nucleic acid molecule which is complementary to the nucleotide sequence shown in SEQ ID NO: 1, or 3, is one which is sufficiently complementary to the nucleotide sequence shown in SEQ ID NO: 1, or 3 such that it can hybridize to the nucleotide sequence shown in SEQ ID NO: 1, or 3 respectively, thereby forming a stable duplex.

In still another preferred embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence shown in SEQ ID NO: 1 or 3, or a portion of any of these nucleotide sequences.

Moreover, the nucleic acid molecule of the invention can comprise only a portion of the nucleic acid sequence of SEQ ID NO: 1, or 3, for example, a fragment which can be used as a probe or primer or a fragment which encodes a portion of a PD-L3 polypeptide, e.g., a biologically active portion of a PD-L3-polypeptide. The nucleotide sequences determined from the cloning of the human PD-L2 gene allow for the generation of probes and primers designed for use in identifying and/or cloning other PD-L2 family members, as well as PD-L3 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO: 1, or 3; of an anti-sense sequence of SEQ ID NO: 1, 3, or a naturally occurring allelic variant or mutant of SEQ ID NO: 1, or 3.

In one embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 800-850, 850-900, 900-950, 950-1000, 1000-1050, 1050-1100, 1100-1150 or more nucleotides in length and hybridizes under stringent hybridization conditions to a nucleic acid molecule of SEQ ID NO: 1, or 3, or the complement thereof. In a further embodiment, a nucleic acid molecule of the present invention comprises a nucleotide sequence which is greater than about 880-900, 900-950, 950-1000, 1000-1050, 1050-1100, 1100-1150 or more nucleotides in length and hybridizes under stringent hybridization conditions to a nucleic acid molecule of SEQ ID NO: 1 or 3, or the complement thereof. In yet another embodiment, a nucleic acid molecule of the present invention comprises a nucleotide sequence which is greater than 50-100, 100-150, 150-200, 200-250, 250-300 or more nucleotides in length and hybridizes under stringent hybridization conditions to a nucleic acid molecule comprising the coding region in SEQ ID NO: 1 or 3, or a complement thereof. In yet a further embodiment, a nucleic acid molecule of the present invention comprises a nucleotide sequence which is greater than about 50-100, 100-150, 150-200, 200-250, 250-300, 300-350, 350-400, 400-450, 450-500, 500-550, 550-600, 600-650, 650-700, 700-750, 750-800, 850-900, 900-950, 950-1000-1050-1100, 1100-1150 or more nucleotides in length, includes at least about 15 (i.e., 15 contiguous) nucleotides of the sequence comprising the coding region of SEQ ID NO: 1 or 3, or a complement thereof, and hybridizes under stringent conditions to a nucleic acid molecule comprising the nucleotide sequence shown in SEQ ID NO: 1, or 3 a complement thereof.

Probes based on the PD-L3 nucleotide sequences can be used to detect transcripts or genomic sequences encoding the same or homologous polypeptides. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PD-L3 polypeptide, such as by measuring a level of a PD-L3-encoding nucleic acid in a sample of cells from a subject e.g., detecting PD-L3 mRNA levels or determining whether a genomic PD-L3 gene has been mutated or deleted.

A nucleic acid fragment encoding a "biologically active portion of a PD-L3 polypeptide" can be prepared by isolating a portion of the nucleotide sequence of SEQ ID NO: 1, or 3 which encodes a polypeptide having a PD-L3 biological activity (e.g., the ability to bind to its natural binding partner(s) and/or modulate immune cell activity), expressing the encoded portion of the PD-L3 polypeptide (e.g., by recombinant expression in vitro) and assessing the activity of the encoded portion of the PD-L3 polypeptide.

The invention further encompasses nucleic acid molecules that differ from the nucleotide sequence shown in SEQ ID NO: 1, or 3 due to degeneracy of the genetic code and thus encode the same PD-L3 polypeptides as those encoded by the nucleotide sequence shown in SEQ ID NO: 1, or 3. In another embodiment, an isolated nucleic acid molecule of the invention has a nucleotide sequence encoding a polypeptide having an amino acid sequence shown in SEQ ID NO: 2, 4 or 5.

In addition to the PD-L3 nucleotide sequences shown in SEQ ID NO: 1, and 3, it will be appreciated by those skilled in the art that DNA sequence polymorphisms that lead to changes in the amino acid sequences of the PD-L3 polypeptides may exist within a population (e.g., the human population). Such genetic polymorphism in the PD-L3 genes may exist among individuals within a population due to natural allelic variation. As used herein, the terms "gene" and "recombinant gene" refer to nucleic acid molecules which include an open reading frame encoding a PD-L3 polypeptide, preferably a mammalian PD-L3 polypeptide, and can further include non-coding regulatory sequences, and introns.

Allelic variants of human or mouse PD-L3 include both functional and non-functional PD-L3 polypeptides. Functional allelic variants are naturally occurring amino acid sequence variants of the human or mouse PD-L3 polypeptide that maintain the ability to bind natural PD-L3 binding partner(s) and/or modulate CD4+ and CD8+ T cell proliferation and cytokine production and lymphocyte activation. Functional allelic variants will typically contain only conservative substitution of one or more amino acids of SEQ ID NO: 2, 4 or 5, or substitution, deletion or insertion of non-critical residues in non-critical regions of the polypeptide.

Non-functional allelic variants are naturally occurring amino acid sequence variants of the human or mouse PD-L3 polypeptide that do not have the ability to either bind natural PD-L3 binding partners, and/or modulate any of the PD-L3 activities described herein. Non-functional allelic variants will typically contain a non-conservative substitution, deletion, or insertion or premature truncation of the amino acid sequence of SEQ ID NO: 2, 4 or 5, or a substitution, insertion or deletion in critical residues or critical regions of the polypeptide, e.g., in an IgV domain.

The present invention further provides non-human, non-mouse orthologs of the human or mouse PD-L3 polypeptide. Orthologs of the human or mouse PD-L3 polypeptide are polypeptides that are isolated from non-human, non-mouse organisms and possess the same binding activity and/or lymphocyte activation-modulating activity, and ability to modulate CD4+ and CD8+ T cell proliferation and cytokine production as the human and murine PD-L3 polypeptides disclosed herein. Orthologs of the human or mouse PD-L2 polypeptide can readily be identified as comprising an amino acid sequence that is substantially identical to SEQ ID NO: 2, 4 or 5.

Moreover, nucleic acid molecules encoding other PD-L3 family members and, thus, which have a nucleotide sequence which differs from the PD-L3 sequences of SEQ ID NO: 1, or 3 are intended to be within the scope of the invention. For example, another PD-L3 cDNA can be identified based on the nucleotide sequence of mouse or human PD-L3. Moreover, nucleic acid molecules encoding PD-L3 polypeptides from different species, and which, thus, have a nucleotide sequence which differs from the PD-L3 sequences of SEQ ID NO: 1, or 3 are intended to be within the scope of the invention. For example, a monkey PD-L3 cDNA can be identified based on the nucleotide sequence of the mouse or human PD-L3.

Nucleic acid molecules corresponding to natural allelic variants and homologues of the PD-L3 cDNAs of the invention can be isolated based on their homology to the PD-L2 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the PD-L3 cDNAs of the invention can further be isolated by mapping to the same chromosome or locus as the PD-L3 gene.

Accordingly, in another embodiment, an isolated nucleic acid molecule of the invention is at least 15, 20, 25, 30 or more nucleotides in length and hybridizes under stringent conditions to the nucleic acid molecule comprising the coding region of the nucleotide sequence of SEQ ID NO: 1 or 3. In other embodiment, the nucleic acid is at least 880-900, 900-950, 950-1000, 1000-1050, 1050-1100, 1100-1150 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, InC (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4 times or 6 times sodium chloride/sodium citrate (SSC), at about 65-70 degrees C. (or hybridization in 4 times SSC plus 50% formamide at about 42-50 degrees C.) followed by one or more washes in 1×SSC, at about 65-70 degrees C. A further preferred, non-limiting example of stringent hybridization conditions includes hybridization at 6 times SSC at 45 degrees C., followed by one or more washes in 0.2 times SSC, 0.1% SDS at 65 degrees C. A preferred, non-limiting example of highly stringent hybridization conditions includes hybridization in 1 times SSC, at about 65-70 degrees C. (or hybridization in 1 times SSC plus 50% formamide at about 42-50 degrees C.) followed by one or more washes in 0.3 times SSC, at about 65-70 degrees C. A preferred, non-limiting example of reduced stringency hybridization conditions includes hybridization in 4 times or 6 times SSC, at about 50-60 degrees C. (or alternatively hybridization in 6 times SSC plus 50% formamide at about 40-45 degrees C.) followed by one or more washes in 2 times SSC, at about 50-60 degrees C. Ranges intermediate to the above-recited values, e.g., at 65-70 degrees C. or at 42-50 degrees C. are also intended to be encompassed by the present invention. SSPE (1 times SSPE is 0.15M NaCl, 10 mM NaH2PO4, and 1.25 mM EDTA, pH 7.4) can be substituted for SSC (1 times SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10 degrees C. less than the melting temperature (Tm) of the hybrid, where Tm is determined according to the following equations. For hybrids less than 18 base pairs in length, Tm (degrees C.)=2(# of A+T bases)+4(# of G+C bases). For hybrids between 18 and 49 base pairs in length, Tm(degrees C.)=81.5+16.6(log 10[Na+])+0.41(% G+C)−(600/N), where N is the number of bases in the hybrid, and [Na+] is the concentration of sodium ions in the hybridization buffer ([Na.sup.+] for 1 times SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M NaH2PO4, 7% SDS at about 65 degrees C., followed by one or more washes at 0.02M NaH2PO4, 1% SDS at 65 degrees C., see e.g., Church and Gilbert (1984) Proc. Natl. Acad. Sci. USA 81:1991-1995 (or alternatively 0.2 times SSC, 1% SDS).

Preferably, an isolated nucleic acid molecule of the invention that hybridizes under stringent conditions to the sequence of SEQ ID NO: 1, or 3 or corresponds to a naturally-occurring nucleic acid molecule. As used herein, a "naturally-occurring" nucleic acid molecule refers to an RNA or DNA molecule having a nucleotide sequence that occurs in nature (i.e., encodes a natural polypeptide).

In addition to naturally-occurring allelic variants of the PD-L3 sequences that may exist in the population, the skilled artisan will further appreciate that changes can be introduced by mutation into the nucleotide sequences of SEQ ID NO: 1 or 3, thereby leading to changes in the amino acid sequence of the encoded PD-L3 polypeptides, without altering the functional ability of the PD-L3 polypeptides. For example, nucleotide substitutions leading to amino acid substitutions at "non-essential" amino acid residues can be made in the sequence of SEQ ID NO: 1, or 3. A "non-essential" amino acid residue is a residue that can be altered from the wild-type sequence of PD-L3 (e.g., the sequence of SEQ ID NO: 2, 4 or 5) without altering the biological activity, whereas an "essential" amino acid residue is required for biological activity. For example, amino acid residues that are conserved among the PD-L3 polypeptides of the present invention, e.g., those present in an extracellular domain, are predicted to be particularly unamenable to alteration. Furthermore, additional amino acid residues that are conserved between the PD-L3 polypeptides of the present invention and other members of the PD-L3 family are not likely to be amenable to alteration.

Accordingly, another aspect of the invention pertains to nucleic acid molecules encoding PD-L3 polypeptides that contain changes in amino acid residues that are not essential for activity. Such PD-L3 polypeptides differ in amino acid sequence from SEQ ID NO: 2, 4 or 5, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to SEQ ID NO: 2, 4 or 5.

An isolated nucleic acid molecule encoding a PD-L2 polypeptide identical to the polypeptide of SEQ ID NO: 2, 4 or 5 can be created by introducing one or more nucleotide substitutions, additions or deletions into the nucleotide sequence of SEQ ID NO: 1 or 3 such that one or more amino acid substitutions, additions or deletions are introduced into the encoded polypeptide. Mutations can be introduced into SEQ ID NO: 1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PD-L3 polypeptide is preferably replaced with another amino acid residue from the same side chain family. Alternatively, in another embodiment, mutations can be introduced randomly along all or part of a PD-L3 coding sequence, such as by saturation mutagenesis, and the resultant mutants can be screened for PD-L3 biological activity to identify mutants that retain activity. Following mutagenesis of SEQ ID NO: 1, or 3, the encoded polypeptide can be expressed recombinantly and the activity of the polypeptide can be determined.

In a preferred embodiment, a mutant PD-L3 polypeptide can be assayed for the ability to bind to and/or modulate the activity of a natural PD-L3 binding partner, to modulate intra- or intercellular signaling, modulate activation of T lymphocytes, and/or modulate the immune response of an organism.

Yet another aspect of the invention pertains to isolated nucleic acid molecules encoding a PD-L3 fusion proteins. Such nucleic acid molecules, comprising at least a first nucleotide sequence encoding a PD-L3 protein, polypeptide or peptide operatively linked to a second nucleotide sequence encoding a non-PD-L3 protein, polypeptide or peptide, can be prepared by standard recombinant DNA techniques.

In addition to the nucleic acid molecules encoding PD-L2 polypeptides described above, another aspect of the invention pertains to isolated nucleic acid molecules which are antisense thereto. An "antisense" nucleic acid comprises a nucleotide sequence which is complementary to a "sense" nucleic acid encoding a polypeptide, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PD-L3 coding strand, or to only a portion thereof. In one embodiment, an antisense nucleic acid molecule is antisense to a "coding region" of the coding strand of a nucleotide sequence encoding a PD-L3. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PD-L. The term "noncoding region" refers to 5' and 3' sequences which flank the coding region that are not translated into amino acids (also referred to as 5' and 3' untranslated regions). Given the coding strand sequences encoding human or mouse PD-L3 disclosed herein, antisense nucleic acids of the invention can be designed according to the rules of Watson and Crick base pairing. The antisense nucleic acid molecule can be complementary to the entire coding region of PD-L3 mRNA, but more preferably is an oligonucleotide which is antisense to only a portion of the coding or noncoding region of PD-L3 mRNA. For example, the antisense oligonucleotide can be complementary to the region surrounding the translation start site of PD-L3 mRNA. An antisense oligonucleotide can be, for example, about 5, 10, 15, 20, 25, 30, 35, 40, 45 or 50 nucleotides in length. An antisense nucleic acid molecule of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PD-L3 polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an .alpha.-anomeric nucleic acid molecule. An .alpha.-anomeric nucleic acid molecule forms specific double-stranded hybrids with complementary RNA in which, contrary to the usual .beta.-units, the strands run parallel to each other (Gaultier et al. (1987) Nucleic Acids Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585-591)) can be used to catalytically cleave PD-L3 mRNA transcripts to thereby inhibit translation of PD-L3 mRNA. A ribozyme having specificity for a PD-L3-encoding nucleic acid can be designed based upon the nucleotide sequence of a PD-L3 cDNA disclosed herein (i.e., SEQ ID NO: 1 or 3). For example, a derivative of a Tetrahymena L-19 IVS RNA can be constructed in which the nucleotide sequence of the active site is complementary to the nucleotide sequence to be cleaved in a PD-L3-encoding mRNA. See, e.g., Cech et al., U.S. Pat. No. 4,987,071 and Cech et al., U.S. Pat. No. 5,116,742. Alternatively, PD-L3 mRNA can be used to select a catalytic RNA having a specific ribonuclease activity from a pool of RNA molecules. See, e.g., Bartel, D. and Szostak, J. W. (1993) Science 261:1411-1418.

Alternatively, PD-L3 gene expression can be inhibited by targeting nucleotide sequences complementary to the regulatory region of the PD-L3 (e.g., the PD-L3 promoter and/or enhancers; to form triple helical structures that prevent transcription of the PD-L3 gene in target cells. See generally, Helene, C (1991) Anticancer Drug Des. 6(6):569-84; Helene, C et al. (1992) Ann. N.Y. Acad. Sci. 660:27-36; and Maher, L. J. (1992) Bioessays 14(12):807-15.

In yet another embodiment, the PD-L3 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) Bioorg. Med. Chem. 4(1):5-23). As used herein, the terms "peptide nucleic acids" or "PNAs" refer to nucleic acid mimics, e.g, DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) Proc Natl. Acad. Sci. USA 93:14670-675.

PNAs of PD-L3 nucleic acid molecules can be used in therapeutic and diagnostic applications. For example, PNASscan be used as antisense or antigene agents for sequence-specific modulation of gene expression by, for example, inducing transcription or translation arrest or inhibiting replication. PNAs of PD-L3 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup and Nielsen (1996) supra)); or as probes or primers for DNA sequencing or hybridization (Hyrup and Nielsen (1996) supra; Perry-O'Keefe et al. (1996) supra).

In another embodiment, PNAs of PD-L3 can be modified (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PD-L3 nucleic acid molecules can be generated which may combine the advantageous properties of PNA and DNA. Such chimeras allow DNA recognition enzymes (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup and Nielsen (1996) supra). The synthesis of PNA-DNA chimeras can be performed as described in Hyrup and Nielsen (1996) supra and Finn P. J. et al. (1996) Nucleic Acids Res. 24 (17):3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a bridge between the PNA and the 5' end of DNA (Mag, M. et al. (1989) Nucleic Acids Res. 17:5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al. (1989) Proc Natl. Acad. Sci. USA 86:6553-6556; Lemaitre et al. (1987) Proc Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (See, e.g., Krol et al. (1988) Biotechniques 6:958-976) or intercalating agents (See, e.g., Zon (1988) Pharm. Res. 5:539-549). To this end, the oligonucleotide may be conjugated to another molecule (e.g., a peptide, hybridization triggered cross-linking agent, transport agent, or hybridization-triggered cleavage agent).

Alternatively, the expression characteristics of an endogenous PD-L3 gene within a cell line or microorganism may be modified by inserting a heterologous DNA regulatory element into the genome of a stable cell line or cloned microorganism such that the inserted regulatory element is operatively linked with the endogenous PD-L3 gene. For example, an endogenous PD-L3 gene which is normally "transcriptionally silent", i.e., a PD-L3 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous PD-L3 gene may be activated by insertion of a promiscuous regulatory element that works across cell types.

A heterologous regulatory element may be inserted into a stable cell line or cloned microorganism, such that it is operatively linked with an endogenous PD-L3 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated PD-L3 Polypeptides and Anti-PD-L3 Antibodies

One aspect of the invention pertains to isolated PD-L3 polypeptides, and biologically active portions thereof, as well as polypeptide fragments suitable for use as immunogens to raise anti-PD-L3 antibodies. In one embodiment, native PD-L3 polypeptides can be isolated from cells or tissue sources by an appropriate purification scheme using standard protein purification techniques. In another embodiment, PD-L3 polypeptides are produced by recombinant DNA techniques. Alternative to recombinant expression, a PD-L3 protein or polypeptide can be synthesized chemically using standard peptide synthesis techniques.

An "isolated" or "purified" polypeptide or biologically active portion thereof is substantially free of cellular material or other contaminating proteins from the cell or tissue source from which the PD-L3 polypeptide is derived, or substantially free from chemical precursors or other chemicals when chemically synthesized. The language "substantially free of cellular material" includes preparations of PD-L3 polypeptide in which the polypeptide is separated from cellular components of the cells from which it is isolated or recombinantly produced. In one embodiment, the language "substantially free of cellular material" includes preparations of PD-L3 polypeptide having less than about 30% (by dry weight) of non-PD-L3 protein (also referred to herein as a "contaminating protein"), more preferably less than about 20% of non-PD-L3 protein, still more preferably less than about 10% of non-PD-L3 protein, and most preferably less than about 5% non-PD-L3 protein. When the PD-L3 polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PD-L3 polypeptide in which the polypeptide is separated from chemical precursors or other chemicals which are involved in the synthesis of the polypeptide. In one embodiment, the language "substantially free of chemical precursors or other chemicals" includes preparations of PD-L3 polypeptide having less than about 30% (by dry weight) of chemical precursors or non-PD-L3 chemicals, more preferably less than about 20% chemical precursors or non-PD-L3 chemicals, still more preferably less than about 10% chemical precursors or non-PD-L3 chemicals, and most preferably less than about 5% chemical precursors or non-PD-L3 chemicals.

As used herein, a "biologically active portion" of a PD-L3 polypeptide includes a fragment of a PD-L3 polypeptide which participates in an interaction between a PD-L3 molecule and a non-PD-L3 molecule, e.g., a natural ligand of PD-L3. Biologically active portions of a PD-L3 polypeptide include peptides comprising amino acid sequences sufficiently identical to or derived from the amino acid sequence of the PD-L3 polypeptide, e.g., the amino acid sequence shown in SEQ ID NO: 2, 4 or 5, which include fewer amino acids than the full length PD-L3 polypeptides, and exhibit at least one activity of a PD-L3 polypeptide. Typically, biologically active portions comprise a domain or motif with at least one activity of the PD-L3 polypeptide, e.g., modulating (suppressing)CD4 T cell proliferative responses to anti-CD3, suppression of the proliferative response of cognate CD4 T cells in an antigen specific manner, effects on the expression of specific cytokines, et al. A biologically active portion of a PD-L3 polypeptide can be a polypeptide which is, for example, 25, 50, 75, 100, 125, 150, 175, 200, 225 or more amino acids in length. Biologically active portions of a PD-L3 polypeptide can be used as targets for developing agents which modulate a PD-L3-mediated activity, e.g., immune cell activation.

In one embodiment, a biologically active portion of a PD-L3 polypeptide comprises at least a portion of an extracellular domain. It is to be understood that a preferred biologically active portion of a PD-L3 polypeptide of the present invention may contain at least a portion of an extracellular domain (e.g., comprising an IgV), and one or more of the following domains: a signal peptide domain, a transmembrane domain, and a cytoplasmic domain. Moreover, other biologically active portions, in which other regions of the polypeptide are deleted, can be prepared by recombinant techniques and evaluated for one or more of the functional activities of a native PD-L3 polypeptide.

In a preferred embodiment, the PD-L3 polypeptide has an amino acid sequence shown in SEQ ID NO: 2, 4 or 5. In other embodiments, the PD-L3 polypeptide is substantially identical to SEQ ID NO: 2, 4 or 5, and retains the functional activity of the polypeptide of SEQ ID NO: 2, 4 or 5, yet differs in amino acid sequence due to natural allelic variation or mutagenesis, as described above.

The nucleic acid and polypeptide sequences of the present invention can further be used as a "query sequence" to perform a search against public databases to, for example, identify other family members or related sequences. Such searches can be performed using the NBLAST and XBLAST programs (version 2.0) of Altschul et al. (1990) J. Mol. Biol. 215:403-10. BLAST nucleotide searches can be performed with the NBLAST program, score=100, wordlength=12 to obtain nucleotide sequences homologous to PD-L3 nucleic acid molecules of the invention. BLAST protein searches can be performed with the XBLAST program, score=100, wordlength=3 to obtain amino acid sequences homologous to PD-L3 polypeptide molecules of the invention. To obtain gapped alignments for comparison purposes, Gapped BLAST can be utilized as described in Altschul et al. (1997) Nucleic Acids Res. 25(17):3389-3402. When utilizing BLAST and Gapped BLAST programs, the default parameters of the respective programs (e.g., XBLAST and NBLAST) can be used. See the Internet website for the National Center for Biotechnology Information.

The invention also provides PD-L3 chimeric or fusion proteins. As used herein, a PD-L3 "chimeric protein" or "fusion protein" comprises a PD-L3 polypeptide operatively linked to a non-PD-L3 polypeptide. A "PD-L3 polypeptide" refers to a polypeptide having an amino acid sequence corresponding to a PD-L3 molecule, whereas a "non-PD-L3 polypeptide" refers to a polypeptide having an amino acid sequence corresponding to a polypeptide which is not substantially homologous to the PD-L3 polypeptide, e.g., a polypeptide which is different from the PD-L3 polypeptide and which is derived from the same or a different organism. Within a PD-L3 fusion protein, the PD-L3 polypeptide can correspond to all or a portion of a PD-L3 polypeptide. In a preferred embodiment, a PD-L3 fusion protein comprises at least one biologically active portion of a PD-L3 polypeptide. In another preferred embodiment, a PD-L3 fusion protein comprises at least two domains of a PD-L3 polypeptide.

Within the fusion protein, the term "operatively linked" is intended to indicate that the PD-L3 polypeptide and the non-PD-L3 polypeptide are fused in-frame to each other. The non-PD-L3 polypeptide can be fused to the N-terminus or C-terminus of the PD-L3 polypeptide and corresponds to a moiety that alters the solubility, binding affinity, stability, or valency of the PD-L3 polypeptide.

For example, in one embodiment, the fusion protein is a GST-PD-L3 fusion protein in which the PD-L3 sequences are fused to the C-terminus of the GST sequences. Such fusion proteins can facilitate the purification of recombinant PD-L3. In another embodiment, the fusion protein is a PD-L3 polypeptide containing a heterologous signal sequence at its N-terminus. In certain host cells (e.g., mammalian host cells), expression and/or secretion of PD-L3 can be increased through use of a heterologous signal sequence. In a preferred embodiment, the fusion protein is an Ig-PD-L3 fusion protein in which the PD-L3 sequences are fused to a portion of an Ig molecule. The Ig portion of the fusion protein can include and immunoglobulin constant region, e.g., a human Cgamma1 domain or a C gamma4 domain (e.g., the hinge, CH2, and CH3 regions of human IgC gamma1 or human IgC gamma4 (see, e.g., Capon et al., U.S. Pat. Nos. 5,116,964; 5,580,756; 5,844,095, and the like, incorporated herein by reference). A resulting fusion protein may have altered PD-L3 solubility, binding affinity, stability and/or valency (i.e., the number of binding sites per molecule) and may increase the efficiency of protein purification.

Particularly preferred PD-L31 g fusion proteins include an extracellular domain portion of PD-L3 coupled to an immunoglobulin constant region (e.g, the Fc region). The immunoglobulin constant region may contain genetic modifications which reduce or eliminate effector activity inherent in the immunoglobulin structure. For example, DNA encoding an extracellular portion of a PD-L3 polypeptide can be joined to DNA encoding the hinge, CH2, and CH3 regions of human IgG gamma1 and/or IgG gamma4 modified by site-directed mutagenesis, e.g., as taught in WO 97/28267. The PD-L3 fusion proteins of the invention can be incorporated into pharmaceutical compositions and administered to a subject in vivo. The PD-L3 fusion proteins can be used to affect the bioavailability of a PD-L3 binding partner. Use of PD-L3 fusion proteins may be useful therapeutically for the treatment of conditions or disorders that would benefit from modulation of the immune response. Moreover, the PD-L3-fusion proteins of the invention can be used as immunogens to produce anti-PD-L3 antibodies in a subject, to purify PD-L3-binding proteins, and in screening assays to identify molecules which inhibit the interaction of PD-L3 with its natural binding partner, Preferably, a PD-L3 chimeric or fusion protein of the invention is produced by standard recombinant DNA techniques.

The present invention also pertains to variants of the PD-L3 polypeptides which function as either PD-L3 agonists (mimetics) or as PD-L3 antagonists. Variants of the PD-L3 polypeptides can be generated by mutagenesis, e.g., discrete point mutation or truncation of a PD-L3 polypeptide. An agonist of the PD-L3 polypeptides can retain substantially the same, or a subset, of the biological activities of the naturally occurring form of a PD-L3 polypeptide. An antagonist of a PD-L3 polypeptide can inhibit one or more of the activities of the naturally occurring form of the PD-L3 polypeptide by, for example, competitively modulating a PD-L3-mediated activity of a PD-L3 polypeptide. Thus, specific biological effects can be elicited by treatment with a variant of limited function.

In one embodiment, treatment of a subject with a variant having a subset of the biological activities of the naturally occurring form of the polypeptide has fewer side effects in a subject relative to treatment with the naturally occurring form of the PD-L3 polypeptide.

In one embodiment, variants of a PD-L3 polypeptide which function as either PD-L3 agonists (mimetics) or as PD-L3 antagonists can be identified by screening combinatorial libraries of mutants, e.g., truncation mutants, of a PD-L3 polypeptide for PD-L3 polypeptide agonist or antagonist activity. In one embodiment, a variegated library of PD-L3 variants is generated by combinatorial mutagenesis at the nucleic acid level and is encoded by a variegated gene library. A variegated library of PD-L3 variants can be produced by, for example, enzymatically ligating a mixture of synthetic oligonucleotides into gene sequences such that a degenerate set of potential PD-L3 sequences is expressible as individual polypeptides, or alternatively, as a set of larger fusion proteins (e.g., for phage display) containing the set of PD-L3 sequences therein. There are a variety of methods which can be used to produce libraries of potential PD-L3 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PD-L3 sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acids Res. 11:477).

In addition, libraries of fragments of a PD-L3 polypeptide coding sequence can be used to generate a variegated population of PD-L3 fragments for screening and subsequent selection of variants of a PD-L3 polypeptide. In one embodiment, a library of coding sequence fragments can be generated by treating a double stranded PCR fragment of a PD-L3 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PD-L3 polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PD-L3 polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PD-L3 variants (Arkin and Youvan (1992) Proc Natl. Acad. Sci. USA 89:7811-7815; Delagrave et al. (1993) Protein Eng. 6(3):327-331).

In addition to PD-L3 polypeptides consisting only of naturally-occurring amino acids, PD-L3 peptidomimetics are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) Adv. Drug Res. 15:29; Veber and Freidinger (1985) TINS p. 392; and Evans et al. (1987) J. Med. Chem. 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human or mouse PD-L3, but have one or more peptide linkages optionally replaced by a linkage selected from the group consisting of: —CH2NH—, —CH2S—, —CH2-CH2-, —CH.dbd.CH— (cis and trans), —COCH2-, —CH(OH)CH2-, and —CH2SO—, by methods known in the art and further described in the following references: Spatola, A. F. in Chemistry and Biochemistry of Amino Acids, Peptides, and Proteins Weinstein, B., ed., Marcel Dekker, New York, p. 267 (1983); Spatola, A. F., Vega Data (March 1983), Vol. 1, Issue 3, "Peptide Backbone Modifications"; Morley, J. S. (1980) Trends. Pharm. Sci. pp. 463-468; Hudson, D. et al. (1979) Int. J. Pept. Prot. Res. 14:177-185 (—CH2NH—, CH2CH2-); Spatola, A. F. et al. (1986) Life. Sci. 38:1243-1249 (—CH2-S); Hann, M. M. (1982) J. Chem. SoC Perkin. Trans. 1307-314 (—CH—CH—, cis and trans); Almquist, R. G. et al. (1980) J. Med. Chem. 23:1392-1398 (—COCH2-); Jennings-White, C et al. (1982) Tetrahedron Lett. 23:2533 (—COCH2-); Szelke, M. et al., European Patent Application No. EP 45665 (1982) CA: 97:39405 (—CH(OH)CH2-); Holladay, M. W. et al. (1983) Tetrahedron. Lett. 24:4401-4404 (—C(OH)CH2-); and Hruby, V. J. (1982) Life Sci. 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetiC Systematic substitution of one or more amino acids of a PD-L3 amino acid sequence with a D-amino acid of the same type (e.g., D-lysine in place of L-lysine) can be used to generate more stable peptides. In addition, constrained peptides comprising a PD-L3 amino acid sequence or a substantially identical sequence variation can be generated by methods known in the art (Rizo and Gierasch (1992) Annu. Rev. Biochem. 61:387, incorporated herein by reference); for example, by adding internal cysteine residues capable of forming intramolecular disulfide bridges which cyclize the peptide. The amino acid sequences of the PD-L3 polypeptides identified herein will enable those of skill in the art to produce polypeptides corresponding to PD-L3 peptide sequences and sequence variants thereof. Such polypeptides can be produced in prokaryotic or eukaryotic host cells by expression of polynucleotides encoding a PD-L3 peptide sequence, frequently as part of a larger polypeptide. Alternatively, such peptides can be synthesized by chemical methods. Methods for expression of heterologous polypeptides in recombinant hosts, chemical synthesis of polypeptides, and in vitro translation are well known in the art. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

An isolated PD-L3 polypeptide, or a portion or fragment thereof, can be used as an immunogen to generate antibodies that bind PD-L3 using standard techniques for polyclonal and monoclonal antibody preparation. A full-length PD-L3 polypeptide can be used or, alternatively, the invention provides antigenic peptide fragments of PD-L3 for use as immunogens. In one embodiment, an antigenic peptide of PD-L3 comprises at least 8 amino acid residues of the amino acid sequence shown in SEQ ID NO: 2, 4 or 5 and encompasses an epitope of PD-L3 such that an antibody raised against the peptide forms a specific immune complex with the PD-L3 polypeptide. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of PD-L3 that are located in the extracellular domain of the polypeptide, e.g., hydrophilic regions, as well as regions with high antigenicity.

A PD-L3 immunogen typically is used to prepare antibodies by immunizing a suitable subject (e.g., rabbit, goat, mouse, or other mammal) with the immunogen. An appropriate immunogenic preparation can contain, for example, recombinantly expressed PD-L3 polypeptide or a chemically synthesized PD-L3 polypeptide. The preparation can further include an adjuvant, such as Freund's complete or incomplete adjuvant, or similar immunostimulatory agent. Immunization of a suitable subject with an immunogenic PD-L3 preparation induces a polyclonal anti-PD-L3 antibody response.

Accordingly, another aspect of the invention pertains to anti-PD-L3 antibodies. The term "antibody" as used herein refers to immunoglobulin molecules and immunologically active portions of immunoglobulin molecules, i.e., molecules that contain an antigen binding site which specifically binds (immunoreacts with) an antigen, such as a PD-L3. Examples of immunologically active portions of immunoglobulin molecules include F(ab) and F(ab')2 fragments which can be generated by treating the antibody with an enzyme such as pepsin. The invention provides polyclonal and monoclonal antibodies that bind PD-L3 molecules. The term "monoclonal antibody" or "monoclonal antibody composition", as used herein, refers to a population of antibody molecules that contain only one species of an antigen binding site capable of immunoreacting with a particular epitope of PD-L3. A monoclonal antibody composition thus typically displays a single binding affinity for a particular PD-L3 polypeptide with which it immunoreacts.

Polyclonal anti-PD-L3 antibodies can be prepared as described above by immunizing a suitable subject with a PD-L3 immunogen, e.g., a PD-L3-Ig fusion protein. The anti-PD-L3 antibody titer in the immunized subject can be monitored over time by standard techniques, such as with an enzyme linked immunosorbent assay (ELISA) using immobilized PD-L3. If desired, the antibody molecules directed against PD-L3 can be isolated from the mammal (e.g., from the blood) and further purified by well known techniques, such as protein A chromatography to obtain the IgG fraction. At an appropriate time after immunization, e.g, when the anti-PD-L3 antibody titers are highest, antibody-producing cells can be obtained from the subject and used to prepare monoclonal antibodies by standard techniques, such as the hybridoma technique originally described by Kohler and Milstein (1975) Nature 256:495-497 (see also Brown et al. (1981) J. Immunol. 127:539-46; Brown et al. (1980) J. Biol. Chem. 255:4980-83; Yeh et al. (1976) Proc Natl. Acad. Sci. USA 76:2927-31; and Yeh et al. (1982) Int. J. Cancer 29:269-75), the more recent human B cell hybridoma technique (Kozbor et al. (1983) Immunol. Today 4:72), the EBV-hybridoma technique (Cole et al. (1985) Monoclonal Antibodies and Cancer Therapy, Alan R. Liss, Inc., pp. 77-96) or trioma techniques. The technology for producing monoclonal antibody hybridomas is well known (see generally Kenneth, R. H. in Monoclonal Antibodies: A New Dimension In Biological Analyses, Plenum Publishing Corp., New York, N.Y. (1980); Lerner, E. A. (1981) Yale J. Biol. Med. 54:387-402; Gefter, M. L. et al. (1977) Somatic Cell Genet. 3:231-36). Briefly, an immortal cell line (typically a myeloma) is fused to lymphocytes (typically splenocytes) from a mammal immunized with a PD-L3 immunogen as described above, and the culture supernatants of the resulting hybridoma cells are screened to identify a hybridoma producing a monoclonal antibody that binds PD-L3. Any of the many well known protocols used for fusing lymphocytes and immortalized cell lines can be applied for the purpose of generating an anti-PD-L3 monoclonal antibody (see, e.g., Galfre, G. et al. (1977) Nature 266:55052; Gefter et al. (1977) supra; Lerner (1981) supra; and Kenneth (1980) supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PD-L3, e.g., using a standard ELISA assay.

Specific methods for producing antibodies that bind PD-L3 are described in the examples. Alternative to preparing monoclonal antibody-secreting hybridomas, a monoclonal anti-PD-L2 antibody can be identified and isolated by screening a recombinant combinatorial immunoglobulin library (e.g., an antibody phage display library) with PD-L3 to thereby isolate immunoglobulin library members that bind PD-L3. Kits for generating and screening phage display libraries are commercially available As noted these antibodies re screened to identif those tht bind to specific epitopes of PD-L3, e.g. in the Igv domain or other specific domains and/or to select antibodies possessing high affinity and avidity to PD-L3 protein. In addition these antibodies are screened to identify those of which modulate specific functions and effects of PD-L3 on immunity and immune cells in vitro and in vivo. For example assays can be conducted to ascertain the modulatory effect, if any, of a particular anti-PD-L3 antibody on immune functions negatively regulated by PD-L3 including cytokine production by CD4+ or CD8+ T cells, CD28 costimulation, CD4+ T cell proliferation, and the proliferation of naïve and memory CD4+ T cells, et al. In a preferred embodiment assays are conducted to identify potential therapeutic anti-PD-L3 antibodies which in vitro, when the presence of PD-L3-Ig enhance the suppression by PD-L3-Ig as these anti-PD-L3 antibodies behave oppositely in vivo, i.e., they are immunosuppressive.

Additionally, recombinant anti-PD-L3 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al., International Application No. PCT/US86/02269; Akira et al., European Patent Application 184,187; Taniguchi, M., European Patent Application 171,496; Morrison et al., European Patent Application 173,494; Neuberger et al., PCT International Publication No. WO 86/01533; Cabilly et al., U.S. Pat. No. 4,816,567; Cabilly et al., European Patent Application 125,023; Better et al. (1988) Science 240:1041-1043; Liu et al. (1987) Proc Natl. Acad. Sci. USA 84:3439-3443; Liu et al. (1987) J. Immunol. 139:3521-3526; Sun et al. (1987) Proc Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559; Morrison, S. L. (1985) Science 229:1202-1207; Oi et al. (1986) Biotechniques 4:214; Winter, U.S. Pat. No. 5,225,539; Jones et al. (1986) Nature 321:552-525; Verhoeyen et al. (1988) Science 239:1534; and Beidler et al. (1988) J. Immunol. 141:4053-4060.

An anti-PD-L3 antibody (e.g., monoclonal antibody) can be used to isolate PD-L3 by standard techniques, such as affinity chromatography or immunoprecipitation. An anti-PD-L3 antibody can facilitate the purification of natural PD-L3 from cells and of recombinantly produced PD-L3 expressed in host cells. Moreover, an anti-PD-L3 antibody can be used to detect PD-L3 polypeptide (e.g., in a cellular lysate or cell supernatant) in order to evaluate the abundance and pattern of expression of the PD-L3 polypeptide. Anti-PD-L3 antibodies can be used diagnostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, .beta.-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

III. Recombinant Expression Vectors and Host Cells

Another aspect of the invention pertains to vectors, preferably expression vectors, containing a nucleic acid molecule encoding a PD-L3 polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PD-L3 polypeptides, mutant forms of PD-L3 polypeptides, fusion proteins, and the like).

The recombinant expression vectors of the invention can be designed for expression of PD-L3 polypeptides in prokaryotic or eukaryotic cells. For example, PD-L3 polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase. Purified fusion proteins can be utilized in PD-L3 activity assays (e.g., direct assays or competitive assays described in detail below), or to generate antibodies specific for PD-L3 polypeptides, for example. In another embodiment, the PD-L3 expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.). Alternatively, PD-L3 polypeptides can be expressed in insect cells using baculovirus expression vectors. Baculovirus vectors available for expression of polypeptides in cultured insect cells (e.g., Sf9 cells) include the pAc series (Smith et al. (1983) Mol. Cell. Biol. 3:2156-2165) and the pVL series (Lucklow and Summers (1989) Virology 170:31-39). In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PD-L3 mRNA. Regulatory sequences operatively linked to a nucleic acid molecule cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub, H. et al., Antisense RNA as a molecular tool for genetic analysis, Reviews—Trends in Genetics, Vol. 1(1) 1986.

Another aspect of the invention pertains to host cells into which a PD-L3 nucleic acid molecule of the invention is introduced, e.g., a PD-L3 nucleic acid molecule within a recombinant expression vector or a PD-L3 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. A host cell of the invention, such as a prokaryotic or eukaryotic host cell in culture, can be used to produce (i.e., express) a PD-L3 polypeptide. Accordingly, the invention further provides methods for producing a PD-L3 polypeptide using the host cells of the invention. In one embodiment, the method comprises culturing the host cell of the invention (into which a recombinant expression vector encoding a PD-L3 polypeptide has been Introduced) in a suitable medium such that a PD-L3 polypeptide is produced. In another embodiment, the method further comprises isolating a PD-L3 polypeptide from the medium or the host cell.

The host cells of the invention can also be used to produce non-human transgenic animals. For example, in one embodiment, a host cell of the invention is a fertilized oocyte or an embryonic stem cell into which PD-L3-coding sequences have been introduced. Such host cells can then be used to create non-human transgenic animals in which exogenous PD-L3 sequences have been introduced into their genome or homologous recombinant animals in which endogenous PD-L3 sequences have been altered. Such animals are useful for studying the function and/or activity of a PD-L3 and for identifying and/or evaluating modulators of PD-L3 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PD-L3 gene has been altered by homologous recombination between the endogenous gene and an exogenous DNA molecule introduced into a cell of the animal, e.g., an embryonic cell of the animal, prior to development of the animal. A transgenic animal of the invention can be created by introducing a PD-L3-encoding nucleic acid into the male pronuclei of a fertilized oocyte, e.g., by microinjection, retroviral infection, and allowing the oocyte to develop in a pseudopregnant female foster animal. The PD-L3 cDNA sequence of SEQ ID NO: 1 or 4 can be introduced as a transgene into the genome of a non-human animal. Alternatively, a nonhuman homologue of a human PD-L3 gene, such as a monkey or rat PD-L3 gene, can be used as a transgene. Alternatively, a PD-L3 gene homologue, such as another PD-L3 family member, can be isolated based on hybridization to the PD-L3 cDNA sequences of SEQ ID NO: 1, or 3 (described further in subsection I above) and used as a transgene. Intronic sequences and polyadenylation signals can also be included in the transgene to increase the efficiency of expression of the transgene. A tissue-specific regulatory sequence(s) can be operably linked to a PD-L3 transgene to direct expression of a PD-L3 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a PD-L3 transgene in its genome and/or expression of PD-L3 mRNA in tissues or cells of the animals. A transgenic founder animal can then be used to breed additional animals carrying the transgene. Moreover, transgenic animals carrying a transgene encoding a PD-L3 polypeptide can further be bred to other transgenic animals carrying other transgenes.

To create a homologous recombinant animal, a vector is prepared which contains at least a portion of a PD-L3 gene into which a deletion, addition or substitution has been introduced to thereby alter, e.g., functionally disrupt, the PD-L3 gene. The PD-L3 gene can be a human or murine gene (e.g., the cDNA of SEQ ID NO: 1 or 3)

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc Natl. Acad. Sci. USA 89:6232-6236. Another example of a recombinase system is the FLP recombinase system of *S. cerevisiae* (O'Gorman et al. (1991) Science 251:1351-1355. If a cre/loxP recombinase system is used to regulate expression of the transgene, animals containing transgenes encoding both the Cre recombinase and a selected polypeptide are required. Such animals can be provided through the construction of "double" transgenic animals, e.g., by mating two transgenic animals, one containing a transgene encoding a selected polypeptide and the other containing a transgene encoding a recombinase.

Clones of the non-human transgenic animals described herein can also be produced according to the methods described in Wilmut, I. et al. (1997) Nature 385:810-813 and PCT International Publication Nos. WO 97/07668 and WO 97/07669. In brief, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to the morula or blastocyte stage and then transferred to pseudopregnant female foster animal. The offspring borne of this female foster animal will be a clone of the animal from which the cell, e.g., the somatic cell, is isolated.

IV. Pharmaceutical Compositions

The PD-L3 molecules, e.g, the PD-L3 nucleic acid molecules, fragments of PD-L3 polypeptides, and anti-PD-L3 antibodies (also referred to herein as "active compounds" or "modulating agents") of the invention can be incorporated into pharmaceutical compositions suitable for administration. Such compositions typically comprise the nucleic acid molecule, polypeptide, or antibody and a carrier, e.g., a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., modulating agents such as a PD-L3 nucleic acid molecule, a fragment of a PD-L3 polypeptide, an anti-PD-L3 antibody, or a combination of an anti-PD-L3 antibody and an anti-PD-L1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, InC Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity of PD-L3. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such polypeptides may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Techniques for conjugating such therapeutic moiety to antibodies are well known.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see, e.g., Chen et al. (1994) Proc Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. The pharmaceutical compositions can be included in a container, pack, or dispenser together with instructions for administration.

V. Uses and Methods of the Invention

The PD-L3 molecules, e.g., the PD-L3 nucleic acid molecules, polypeptides, polypeptide homologues, and antibodies described herein can be used in one or more of the following methods: a) screening assays; b) predictive medicine (e.g., diagnostic assays, prognostic assays, and monitoring clinical trials); and c) methods of treatment (e.g., therapeutic and prophylactic, e.g., by up- or down-modulating the immune response). As described herein, a PD-L3 polypeptide of the invention has one or more of the following activities: 1) binds to and/or modulates the activity of its natural binding partner(s), 2) modulates intra- or intercellular signaling, 3) modulates activation of T lymphocytes, 4) modulates the immune response of an organism, e.g., a mammalian organism, such as a mouse or human. The isolated nucleic acid molecules of the invention can be used, for example, to express PD-L3 polypeptide (e.g., via a recombinant expression vector in a host cell in gene therapy applications), to detect PD-L3 mRNA (e.g., in a biological sample) or a genetic alteration in a PD-L3 gene, and to modulate PD-L3 activity, as described further below. The PD-L3 polypeptides can be used to treat conditions or disorders characterized by insufficient or excessive production of a PD-L3 polypeptide or production of PD-L3 inhibitors. In addition, the PD-L3 polypeptides can be used to screen for naturally occurring PD-L3 binding partner(s), to screen for drugs or compounds which modulate PD-L3 activity, as well as to treat conditions or disorders characterized by insufficient or excessive production of PD-L3 polypeptide or production of PD-L3 polypeptide forms which have decreased, aberrant or unwanted activity compared to PD-L3 wild-type polypeptide (e.g., immune system disorders such as severe combined immunodeficiency, multiple sclerosis, systemic lupus erythematosus, type I diabetes mellitus, lymphoproliferative syndrome, inflammatory bowel disease, allergies, asthma, graft-versus-host disease, and transplant rejection; immune responses to infectious pathogens such as bacteria and viruses; and immune system cancers such as lymphomas and leukemias). Moreover, the anti-PD-L3 antibodies of the invention can be used to detect and isolate PD-L3 polypeptides, regulate the bioavailability of PD-L3 polypeptides, and modulate PD-L3 activity, e.g., by modulating the interaction between PD-L3 and its natural binding partner(s)

A. Screening Assays:

The invention provides a method (also referred to herein as a "screening assay") for identifying modulators, i.e., candidate or test compounds or agents (e.g., peptides, peptidomimetics, small molecules or other drugs) which bind to PD-L3 polypeptides, have a stimulatory or inhibitory effect on, for example, PD-L3 expression or PD-L3 activity, or have a stimulatory or inhibitory effect on the interaction between PD-L3 and its natural binding partner(s).

In one embodiment, the invention provides assays for screening candidate or test compounds which bind to the PD-L3 protein or polypeptide or biologically active portion thereof, e.g., modulate the ability of the PD-L3 polypeptide to interact with its natural binding partner(s). In another embodiment, the invention provides assays for screening candidate or test compounds which bind to or modulate the activity of a PD-L3 protein or polypeptide or biologically active portion thereof. In a preferred embodiment, the invention provides assays for screening candidate or test compounds which have a stimulatory or inhibitory effect on immune functions negatively regulated by PD-L3 such as are identified herein or based on its effect on the interaction of between PD-L3 and its natural binding partner(s). These PD-L3 related functions include by way of example inhibiting cytokine production (e.g., 11-2, gamma interferon by T cells, suppressing moderate CD28 costimulation, inhibiting CD4+ and CD8+ T cell proliferation, suppressing proliferation of naïve and memory CD4+ T cells, and suppressing TCR activation without inducing apoptosis. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

In one embodiment, an assay is a cell-based assay in which a cell which expresses a PD-L3 polypeptide or biologically active portion thereof is contacted with a test compound, and the ability of the test compound to modulate PD-L3 activity is determined. Determining the ability of the test compound to modulate PD-L3 activity can be accomplished by monitoring, for example, the ability of PD-L3 to bind to its natural binding partner(s), and modulate immune cell activity. The immune cell can be, e.g., a T cell, a B cell, or a myeloid cell. Determining the ability of the test compound to modulate PD-L3 binding to its counter-receptor (to be determined) can be accomplished, for example, by coupling PD-L3 with a radioisotope or enzymatic label to monitor the ability of a test compound to modulate PD-L3 binding to T cells which express the PD-L3 counter-receptor. Determining the ability of the test compound to bind PD-L3 can be accomplished, for example, by coupling the compound with a radioisotope or enzymatic label such that binding of the compound to PD-L3 can be determined by detecting the labeled PD-L3 compound in a complex.

It is also within the scope of this invention to determine the ability of a compound to interact with PD-L3 without the labeling of any of the interactants. For example, a microphysiometer can be used to detect the interaction of a compound with PD-L3 without the labeling of either the compound or the PD-L3 (McConnell, H. M. et al. (1992) Science 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PD-L3.

In another embodiment, an assay is a cell-based assay comprising contacting a T cell expressing a PD-L3 binding partner with a test compound and determining the ability of the test compound to modulate (e.g., stimulate or inhibit) the activity of the PD-L3 binding partner. Determining the ability of the test compound to modulate the activity of a PD-L3 binding partner can be accomplished, for example, by determining the ability of the PD-L3 polypeptide to bind to or interact with the PD-L3 binding partner.

Determining the ability of the PD-L3 polypeptide, or a biologically active fragment thereof, to bind to or interact with a PD-L3 binding partner, can be accomplished by one of the methods described above for determining direct binding. In a preferred embodiment, determining the ability of the PD-L3 polypeptide to bind to or interact with a PD-L3 binding partner can be accomplished by determining the activity of the binding partner. For example, the activity of the binding partner can be determined by detecting induction of a cellular second messenger (e.g., tyrosine kinase or phosphatase activity), detecting catalytic/enzymatic activity of an appropriate substrate, detecting the induction of a reporter gene (comprising a target-responsive regulatory element operatively linked to a nucleic acid encoding a detectable marker, e.g., luciferase), or detecting a target-regulated cellular response. For example, determining the ability of the PD-L3 polypeptide to bind to or interact with a natural PD-L3 binding partner, can be accomplished by measuring the ability of a compound to modulate immune cell costimulation or inhibition in a proliferation assay, or by interfering with the ability of a PD-L3 polypeptide to bind to antibodies that recognize a portion of the PD-L3 polypeptide. In one embodiment, compounds that modulate T cell activation can be identified by determining the ability of a compound to modulate T cell proliferation or cytokine production. In a preferred embodiment, compounds that modulate T cell activation can be identified by determining the ability of a compound to modulate T cell proliferation or cytokine production at more than one antigen concentration.

In yet another embodiment, an assay of the present invention is a cell-free assay in which a PD-L3 polypeptide or biologically active portion thereof is contacted with a test compound and the ability of the test compound to bind to the PD-L3 polypeptide or biologically active portion thereof is determined. Preferred biologically active portions of the PD-L3 polypeptides to be used in assays of the present invention include fragments which participate in interactions with non-PD-L3 molecules, e.g., at least a portion of an extracellular domain which binds to a PD-L3 binding partner. Binding of the test compound to the PD-L3 polypeptide can be determined either directly or indirectly as described above.

In another embodiment, the assay is a cell-free assay in which a PD-L3 polypeptide or biologically active portion thereof is contacted with a test compound and the ability of the test compound to modulate (e.g., stimulate or inhibit) the activity of the PD-L3 polypeptide or biologically active portion thereof is determined. Determining the ability of the test compound to modulate the activity of a PD-L3 polypeptide can be accomplished, for example, by determining the ability of the PD-L3 polypeptide to bind to a PD-L3 binding partner by one of the methods described above for determining direct binding. The cell-free assays of the present invention are amenable to use of both soluble and/or membrane-bound forms of polypeptides (e.g., PD-L3 polypeptides or biologically active portions thereof, or binding partners to which PD-L3 binds). In the case of cell-free assays in which a membrane-bound form a polypeptide is used (e.g., a cell-surface PD-L3), it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl.dbd.N,N-dimethyl-3-ammonio-1-propane sulfonate.

In more than one embodiment of the above assay methods of the present invention, it may be desirable to immobilize either PD-L3 or its binding partner to facilitate separation of complexed from uncomplexed forms of one or both of the polypeptides, as well as to accommodate automation of the assay. Binding of a test compound to a PD-L3 polypeptide, or interaction of a PD-L3 polypeptide with its binding partner in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/PD-L3 fusion proteins or glutathione-S-transferase/binding partner fusion proteins can be adsorbed onto glutathione sepharose beads (Sigma Chemical, St. Louis, Mo.) or glutathione derivatized microtitre plates, which are then combined with the test compound or the test compound and either the non-adsorbed binding partner polypeptide or PD-L3 polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of PD-L3 binding or activity determined using standard techniques. Other techniques for immobilizing polypeptides on matrices can also be used in the screening assays of the invention. In an alternative embodiment, determining the ability of the test compound to modulate the activity of a PD-L3 polypeptide can be accomplished by determining the ability of the test compound to modulate the activity of a molecule that functions downstream of PD-L3, e.g., by interacting with the cytoplasmic domain of a PD-L3 binding partner. For example, levels of second messengers, the activity of the interacting molecule on an appropriate target, or the binding of the interactor to an appropriate target can be determined as previously described.

In another embodiment, modulators of PD-L3 expression are identified in a method wherein a cell is contacted with a candidate compound and the expression of PD-L3 mRNA or polypeptide in the cell is determined. The level of expression of PD-L3 mRNA or polypeptide in the presence of the candidate compound is compared to the level of expression of PD-L3 mRNA or polypeptide in the absence of the candidate compound. The candidate compound can then be identified as a modulator of PD-L3 expression based on this comparison if the change is statistically significant.

In yet another aspect of the invention, the PD-L3 polypeptides can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other polypeptides which bind to or interact with PD-L3 ("PD-L3-binding proteins", "PD-L3 binding partners", or "PD-L3-bp") and are involved in PD-L3 activity. Such PD-L3-binding proteins are also likely to be involved in the propagation of signals by the PD-L3 polypeptides or PD-L3 targets as, for example, downstream elements of a PD-L3-mediated signaling pathway. Alternatively, such PD-L3-binding polypeptides may be PD-L3 inhibitors. The two-hybrid system is based on the modular nature of most transcription factors, which consist of separable DNA-binding and activation domains. Briefly, the assay utilizes two different DNA constructs. In one construct, the gene that codes for a PD-L3 polypeptide is fused to a gene encoding the DNA binding domain of a known transcription factor (e.g, GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a PD-L3-dependent complex, the DNA-binding and activation domains of the transcription factor are brought into close proximity. This proximity allows transcription of a reporter gene (e.g, LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which Interacts with the PD-L3 polypeptide.

In another aspect, the invention pertains to a combination of two or more of the assays described herein. For example, a modulating agent can be identified using a cell-based or a cell-free assay, and the ability of the agent to modulate the activity of a PD-L3 polypeptide can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein (e.g., a PD-L3 modulating agent, an antisense PD-L3 nucleic acid molecule, a PD-L3-specific antibody, or a PD-L3 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PD-L3 nucleotide sequences, described herein, can be used to map the location of the PD-L3 genes on a chromosome. The mapping of the PD-L3 sequences to chromosomes is an important first step in correlating these sequences with genes associated with disease. Briefly, PD-L3 genes can be mapped to chromosomes by preparing PCR primers (preferably 15-25 bp in length) from the PD-L3 nucleotide sequences. Computer analysis of the PD-L3 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PD-L3 sequences will yield an amplified fragment. Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio, P. et al. (1983) Science 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PD-L3 nucleotide sequences to design oligonucleotide primers, sublocalization can be achieved with panels of fragments from specific chromosomes. Other mapping strategies which can similarly be used to map a PD-L3 sequence to its chromosome include in situ hybridization (described in Fan, Y. et al. (1990) Proc Natl. Acad. Sci. USA 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time. For a review of this technique, see Verma et al., Human Chromosomes: A Manual of basic Techniques (Pergamon Press, New York 1988). Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridization during chromosomal mapping.

Once a sequence has been mapped to a precise chromosomal location, the physical position of the sequence on the chromosome can be correlated with genetic map data Ultimately, complete sequencing of genes from several individuals can be performed to confirm the presence of a mutation and to distinguish mutations from polymorphisms.

2. Tissue Typing

The PD-L3 sequences of the present invention can also be used to identify individuals from minute biological samples. Furthermore, the sequences of the present invention can be used to provide an alternative technique which determines the actual base-by-base DNA sequence of selected portions of an individual's genome. Thus, the PD-L3 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PD-L3 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO: 1 or 4 can comfortably provide positive individual identification with a panel of perhaps 10 to 1,000 primers which each yield a noncoding amplified sequence of 100 bases. If predicted coding sequences, such as those in SEQ ID NO: 3 or 6 are used, a more appropriate number of primers for positive individual identification would be 500-2000.

If a panel of reagents from PD-L3 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of PD-L3 Sequences in Forensic Biology

DNA-based identification techniques can also be used in forensic biology. The sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1 or 3 are particularly appropriate for this use as greater numbers of polymorphisms occur in the noncoding regions, making it easier to differentiate individuals using this technique. Examples of polynucleotide reagents include the PD-L3 nucleotide sequences or portions thereof, e.g., fragments derived from the noncoding regions of SEQ ID NO: 1 or 3 having a length of at least 20 bases, preferably at least 30 bases. The PD-L3 nucleotide sequences described herein can further be used to provide polynucleotide reagents, e.g., labeled or labelable probes which can be used in, for example, an in situ hybridization technique, to identify a specific tissue, e.g., lymphocytes. This can be very useful in cases where a forensic pathologist is presented with a tissue of unknown origin. Panels of such PD-L3 probes can be used to identify tissue by species and/or by organ type. In a similar fashion, these reagents, e.g., PD-L3 primers or probes can be used to screen tissue culture for contamination (i.e., screen for the presence of a mixture of different types of cells in a culture).

C Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PD-L3 polypeptide and/or nucleic acid expression as well as PD-L3 activity, in the context of a biological sample (e.g., blood, serum, cells, or tissue) to thereby determine whether an individual is afflicted with a disease or disorder, or is at risk of developing a disorder, associated with aberrant or unwanted PD-L3 expression or activity. The invention also provides for prognostic (or predictive) assays for determining whether an individual is at risk of developing a disorder associated with PD-L3 polypeptide, nucleic acid expression or activity. For example, mutations in a PD-L3 gene can be assayed in a biological sample.

Such assays can be used for prognostic or predictive purpose to thereby prophylactically treat an individual prior to the onset of a disorder characterized by or associated with PD-L3 polypeptide, nucleic acid expression or activity.

Another aspect of the invention pertains to monitoring the influence of agents (e.g., drugs, compounds) on the expression or activity of PD-L3 in clinical trials. These and other agents are described in further detail in the following sections.

1. Diagnostic Assays

An exemplary method for detecting the presence or absence of PD-L3 polypeptide or nucleic acid in a biological sample involves obtaining a biological sample from a test subject and contacting the biological sample with a compound or an agent capable of detecting PD-L3 polypeptide or nucleic acid (e.g., mRNA or genomic DNA) that encodes PD-L3 polypeptide such that the presence of PD-L3 polypeptide or nucleic acid is detected in the biological sample. A preferred agent for detecting PD-L3 mRNA or genomic DNA is a labeled nucleic acid probe capable of hybridizing to PD-L3 mRNA or genomic DNA. The nucleic acid probe can be, for example, the PD-L3 nucleic acid set forth in SEQ ID NO: 1, or 3, or a portion thereof, such as an oligonucleotide of at least 15, 30, 50, 100, 250 or 500 nucleotides in length and sufficient to specifically hybridize under stringent conditions to PD-L3 mRNA or genomic DNA. Other suitable probes for use in the diagnostic assays of the invention are described herein. A preferred agent for detecting PD-L3 polypeptide is an antibody capable of binding to PD-L3 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect PD-L3 mRNA, polypeptide, or genomic DNA in a biological sample in vitro as well as in vivo. For example, in vitro techniques for detection of PD-L2 mRNA include Northern hybridizations and in situ hybridizations. In vitro techniques for detection of PD-L3 polypeptide include enzyme linked immunosorbent assays (ELISAs), Western blots, immunoprecipitations and immunofluorescence. In vitro techniques for detection of PD-L3 genomic DNA include Southern hybridizations. Furthermore, in vivo techniques for detection of PD-L3 polypeptide include introducing into a subject a labeled anti-PD-L3 antibody. For example, the antibody can be labeled with a radioactive marker whose presence and location in a subject can be detected by standard imaging techniques. In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject. In another embodiment, the methods further involve obtaining a control biological sample from a control subject, contacting the control sample with a compound or agent capable of detecting PD-L3 polypeptide, mRNA, or genomic DNA, such that the presence of PD-L3 polypeptide, mRNA or genomic DNA is detected in the biological sample, and comparing the presence of PD-L3 polypeptide, mRNA or genomic DNA in the control sample with the presence of PD-L3 polypeptide, mRNA or genomic DNA in the test sample.

The invention also encompasses kits for detecting the presence of PD-L3 in a biological sample. For example, the kit can comprise a labeled compound or agent capable of detecting PD-L3 polypeptide or mRNA in a biological sample; means for determining the amount of PD-L3 in the sample; and means for comparing the amount of PD-L3 in the sample with a standard. The compound or agent can be packaged in a suitable container. The kit can further comprise instructions for using the kit to detect PD-L3 polypeptide or nucleic acid.

2. Prognostic Assays

The diagnostic methods described herein can furthermore be utilized to identify subjects having or at risk of developing a disease or disorder associated with aberrant or unwanted PD-L3 expression or activity. As used herein, the term "aberrant" includes a PD-L3 expression or activity which deviates from the wild type PD-L3 expression or activity. Aberrant expression or activity includes increased or decreased expression or activity, as well as expression or activity which does not follow the wild type developmental pattern of expression or the subcellular pattern of expression. For example, aberrant PD-L3 expression or activity is intended to include the cases in which a mutation in the PD-L3 gene causes the PD-L3 gene to be under-expressed or over-expressed and situations in which such mutations result in a non-functional PD-L3 polypeptide or a polypeptide which does not function in a wild-type fashion, e.g., a polypeptide which does not interact with a PD-L3 binding partner, or one which interacts with a non-PD-L3 binding partner. As used herein, the term "unwanted" includes an unwanted phenomenon involved in a biological response such as immune cell activation. For example, the term unwanted includes a PD-L3 expression or activity which is undesirable in a subject.

The assays described herein, such as the preceding diagnostic assays or the following assays, can be utilized to identify a subject having or at risk of developing a disorder associated with a misregulation in PD-L3 polypeptide activity or nucleic acid expression, such as an autoimmune disorder, an immunodeficiency disorder, an immune system disorder such as autoimmunity, allergic or inflammatory disorder or cancer. Thus, the present invention provides a method for identifying a disease or disorder associated with aberrant or unwanted PD-L3 expression or activity in which a test sample is obtained from a subject and PD-L3 polypeptide or nucleic acid (e.g., mRNA or genomic DNA) is detected, wherein the presence of PD-L3 polypeptide or nucleic acid is diagnostic for a subject having or at risk of developing a disease or disorder associated with aberrant or unwanted PD-L3 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant or unwanted PD-L3 expression or activity. For example, such methods can be used to determine whether a subject can be effectively treated with an agent for an autoimmune disorder, immunodeficiency disorder, immune system cancer, or allergic or inflammatory disorder. Thus, the present invention provides methods for determining whether a subject can be effectively treated with an agent for a disorder associated with aberrant or unwanted PD-L3 expression or activity in which a test sample is obtained and PD-L3 polypeptide or nucleic acid expression or activity is detected (e.g., wherein the abundance of PD-L3 polypeptide or nucleic acid expression or activity is diagnostic for a subject that can be administered the agent to treat a disorder associated with aberrant or unwanted PD-L3 expression or activity). The methods of the invention can also be used to detect genetic alterations in a PD-L3 gene, thereby determining if a subject with the altered gene is at risk for a disorder characterized by misregulation in PD-L3 polypeptide activity or nucleic acid expression, such as an autoimmune disorder, an immunodeficiency disorder, an immune system cancer, an allergic disorder, or an inflammatory disorder. The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PD-L3 gene. Furthermore, any cell type or tissue in which PD-L3 is expressed may be utilized in the prognostic assays described herein.

3. Monitoring of Effects During Clinical Trials

Monitoring the influence of agents (e.g., drugs) on the expression or activity of a PD-L3 polypeptide (e.g., the modulation of cell proliferation and/or migration) can be applied not only in basic drug screening, but also in clinical trials. For example, the effectiveness of an agent determined by a screening assay as described herein to increase PD-L3 gene expression, polypeptide levels, or upregulate PD-L3 activity, can be monitored in clinical trials of subjects exhibiting decreased PD-L3 gene expression, polypeptide levels, or downregulated PD-L3 activity. Alternatively, the effectiveness of an agent determined by a screening assay to decrease PD-L3 gene expression, polypeptide levels, or downregulate PD-L3 activity, can be monitored in clinical trials of subjects exhibiting increased PD-L3 gene expression, polypeptide levels, or PD-L3 activity. As noted PD-L3 is expressed on many hematopoietic cell types including APCs (macrophages and myeloid dendritic cells), and CD4+ T cells, and more specifically is expressed on $CD11c^+$ DCs, CD4+ T cells (including both $Foxp3^-$ effector T cells and $Foxp3^+$ nTregs), $CD8^+$ T cells, and $Gr1^+$ granulocytes, and expressed at low levels on B cells and NK cells In such clinical trials, the expression or activity of a PD-L3 gene, and preferably, other genes that have been implicated in, for example, a PD-L3-associated disorder can be used as a "read out" or marker of the phenotype of a particular cell.

For example, and not by way of limitation, genes, including PD-L3, that are modulated in cells by treatment with an agent (e.g., compound, drug or small molecule) which modulates PD-L3 activity (e.g., identified in a screening assay as described herein) can be identified. Thus, to study the effect of agents on PD-L3-associated disorders, for example, in a clinical trial, cells can be isolated and RNA prepared and analyzed for the levels of expression of PD-L3 and other genes implicated in the PD-L3-associated disorder, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of PD-L3 or other genes. In this way, the gene expression pattern can serve as a marker, indicative of the physiological response of the cells to the agent. Accordingly, this response state may be determined before, and at various points during treatment of the individual with the agent. In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a PD-L3 polypeptide, mRNA, or genomic DNA in the preadministration sample; (iii) obtaining one or more post-administration samples from the subject; (iv) detecting the level of expression or activity of the PD-L3 polypeptide, mRNA, or genomic DNA in the post-administration samples; (v) comparing the level of expression or activity of the PD-L3 polypeptide, mRNA, or genomic DNA in the pre-administration sample with the PD-L3 polypeptide, mRNA, or genomic DNA in the post administration sample or samples; and (vi) altering the administration of the agent to the subject accordingly. For example, increased administration of the agent may be desirable to increase the expression or activity of PD-L3 to higher levels than detected, i.e., to increase the effectiveness of the agent. Alternatively, decreased administration of the agent may be desirable to decrease expression or activity of PD-L3 to lower levels than detected, i.e., to decrease the effectiveness of the agent. According to such an embodiment, PD-L3 expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder characterized by insufficient or excessive production of PD-L3 protein or production of PD-L3 protein forms which have decreased or aberrant activity compared to PD-L3 wild type protein. Moreover, the anti-PD-L3 antibodies of the invention can be used to detect and isolate PD-L3 proteins, regulate the bioavailability of PD-L3 proteins, and modulate PD-L3 activity e.g., by modulating the interaction of PD-L3 with its counter receptor.

1. Prophylactic Methods

In one aspect, the invention provides a method for preventing in a subject, a disease or condition associated with an aberrant or unwanted PD-L3 expression or activity, by administering to the subject a PD-L3 polypeptide or an agent which modulates PD-L3 expression or at least one PD-L3 activity. Subjects at risk for a disease or disorder which is caused or contributed to by aberrant or unwanted PD-L3 expression or activity can be identified by, for example, any or a combination of diagnostic or prognostic assays as described herein. Administration of a prophylactic agent can occur prior to the manifestation of symptoms characteristic of the PD-L3 aberrancy, such that a disease or disorder is prevented or, alternatively, delayed in its progression. Depending on the type of PD-L3 aberrancy, for example, a PD-L3 polypeptide, PD-L3 agonist or PD-L3 antagonist (e.g., an anti-PD-L3 antibody) agent can be used for treating the subject. The appropriate agent can be determined based on screening assays described herein.

2. Therapeutic Methods

An important aspect of the invention pertains to methods of modulating PD-L3 expression or activity or interaction with its natural binding partners, Relevant to therapy PD-L3 has been demonstrated to inhibit CD28 costimulation, to inhibit TCR activation of immune cells, to inhibit proliferation of activated immune cells (CD4+ and CD8+ T cells), to inhibit cytokine production by T cells (IL-2, gamma interferon) and to transmit an inhibitory signal to immune cells. Accordingly, the activity and/or expression of PD-L3, as well as the interaction between PD-L3 and its binding partner)s) on T cells can be modulated in order to modulate the immune response. Because PD-L3 binds to inhibitory receptors (on T cells), upregulation of PD-L3 activity should result in downregulation of immune responses, whereas downregulation of PD-L3 activity should results in upregulation of immune responses. In a preferred embodiment, PD-L3 binds to inhibitory receptors. As noted previously, counterintuitively PD-L3 specific antibodies produced by Applicant which in vitro (in the presence of PD-L3-Ig) enhance the suppressive activities of PD-L3-Ig fusion proteins (i.e., these antibodies enhance the suppression of PD-L3 related activities such as effects of PD-L3 on cytokine production, T cell proliferation, differentiation or activation and other functions noted previously), behave oppositely to what would be expected in vivo, i.e., these antibodies have been found to be immunosuppressive in vivo.

Modulatory methods of the invention involve contacting a cell with a PD-L3 polypeptide or agent that modulates one or more of the activities of PD-L3 polypeptide activity associated with the cell, e.g., an agent that modulates expression or activity of PD-L3 and/or modulates the interaction of PD-L3 and its natural binding partner(s). An agent that modulates PD-L3 polypeptide activity can be an agent as described herein, such as a nucleic acid or a polypeptide, a naturally-occurring binding partner of a PD-L3 polypeptide a PD-L3 antibody, a PD-L3 agonist or antagonist, a peptidomimetic of a PD-L3 agonist or antagonist, a PD-L3 peptidomimetic, or other small molecule. Soluble forms of PD-L3 may also be used to interfere with the binding of PD-L3 to any of its natural binding partner(s) or ligands.

An agent that modulates the expression of PD-L3 is, e.g., an antisense nucleic acid molecule, triplex oligonucleotide, ribozyme, or recombinant vector for expression of a PD-L3 polypeptide. For example, an oligonucleotide complementary to the area around a PD-L3 polypeptide translation initiation site can be synthesized. One or more antisense oligonucleotides can be added to cell media, typically at 200 mug/ml, or administered to a patient to prevent the synthesis of a PD-L3 polypeptide. The antisense oligonucleotide is taken up by cells and hybridizes to a PD-L3 mRNA to prevent translation. Alternatively, an oligonucleotide which binds double-stranded DNA to form a triplex construct to prevent DNA unwinding and transcription can be used. As a result of either, synthesis of PD-L3 polypeptide is blocked. When PD-L3 expression is modulated, preferably, such modulation occurs by a means other than by knocking out the PD-L3 gene.

Agents which modulate expression, by virtue of the fact that they control the amount of PD-L3 in a cell, also modulate the total amount of PD-L3 activity in a cell. In one embodiment, the agent the modulates PD-L3 stimulates one or more PD-L3 activities. Examples of such stimulatory agents include active PD-L3 polypeptide and a nucleic acid molecule encoding PD-L3 that has been introduced into the cell. In another embodiment, the agent inhibits one or more PD-L3 activities. Examples of such inhibitory agents include antisense PD-L3 nucleic acid molecules, anti-PD-L3 antibodies, PD-L3 inhibitors, and compounds identified in the subject screening assays. In a further preferred embodiment, an inhibitory agent is a combination of an anti-PD-L3 antibody and an anti-PD-L1 or anti-PD-L2 antibody. These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of a PD-L3 polypeptide, e.g., a disorder characterized by unwanted, insufficient, or aberrant expression or activity of a PD-L3 polypeptide or nucleic acid molecule. In one embodiment, the method involves administering an agent (e.g., an agent identified by a screening assay described herein), or combination of agents that modulates (e.g., upregulates or downregulates) PD-L3 expression or activity. In another embodiment, the method involves administering a PD-L3 polypeptide or nucleic acid molecule as therapy to compensate for reduced, aberrant, or unwanted PD-L3 expression or activity.

Diseases treatable with the subject PD-L3 binding agents are identified previously and include various inflammatory, autoimmune, cancer, allergic and infectious disorders. A particularly preferred indication is multiple sclerosis.

Stimulation of PD-L3 activity is desirable in situations in which PD-L3 is abnormally downregulated and/or in which increased PD-L3 activity is likely to have a beneficial effect. Likewise, inhibition of PD-L3 activity is desirable in situations in which PD-L3 is abnormally upregulated and/or in which decreased PD-L3 activity is likely to have a beneficial effect. Exemplary agents for use in downmodulating PD-L3 (i.e., PD-L3 antagonists) include, e.g., antisense nucleic acid molecules, antibodies that recognize and block PD-L3, combinations of antibodies that recognize and block PD-L3 and antibodies that recognize and block PD-L3 counter receptors, and compounds that block the interaction of PD-L3 with its naturally occurring binding partner(s) on an immune cell (e.g., soluble, monovalent PD-L3 molecules; soluble forms of PD-L3 molecules that do not bind Fc receptors on antigen presenting cells; soluble forms of PD-L3 binding partners; and compounds identified in the subject screening assays). Exemplary agents for use in upmodulating PD-L3 (i.e., PD-L3 agonists) include, e.g., nucleic acid molecules encoding PD-L3 polypeptides, multivalent forms of PD-L3, compounds that increase the expression of PD-L3, compounds that enhance the interaction of PD-L3 with its naturally occurring binding partners and cells that express PD-L3.

3. Downregulation of Immune Responses

There are numerous embodiments of the invention for upregulating the inhibitory function of a PD-L3 polypeptide to thereby downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both. For example, in embodiments where PD-L3 binds to an inhibitory receptor, forms of PD-L3 that bind to the inhibitory receptor, e.g., multivalent PD-L3 on a cell surface, can be used to downmodulate the immune response. In one embodiment of the invention, an activating antibody used to stimulate PD-L3 activity is a bispecific antibody. For example, such an antibody can comprise a PD-L3 binding site and another binding site which targets a cell surface receptor on an immune cell, e.g., a T cell, a B cell, or a myeloid cell. In one embodiment, such an antibody, in addition to comprising a PD-L3 binding site, can further comprise a binding site which binds to a B cell antigen receptor, a T cell antigen receptor, or an Fc receptor, in order to target the molecule to a specific cell population. Selection of this second antigen for the bispecific antibody provides flexibility in selection of cell population to be targeted for inhibition. Agents that promote a PD-L3 activity or which enhance the interaction of PD-L3 with its natural binding partners (e.g., PD-L3 activating antibodies or PD-L3 activating small molecules) can be identified by their ability to inhibit immune cell proliferation and/or effector function, or to induce anergy when added to an in vitro assay. For example, cells can be cultured in the presence of an agent that stimulates signal transduction via an activating receptor. A number of art-recognized readouts of cell activation can be employed to measure, e.g., cell proliferation or effector function (e.g., antibody production, cytokine production, phagocytosis) in the presence of the activating agent. The ability of a test agent to block this activation can be readily determined by measuring the ability of the agent to effect a decrease in proliferation or effector function being measured. In one embodiment, at low antigen concentrations, PD-L3 immune cell interactions inhibit strong B7-CD28 signals. In another embodiment, at high antigen concentrations, PD-L3 immune cell interactions may reduce cytokine production but not inhibit T cell proliferation. Accordingly, the ability of a test compound to block activation can be determined by measuring cytokine production and/or proliferation at different concentrations of antigen.

In one embodiment of the invention, tolerance is induced against specific antigens by co-administering an antigen with a PD-L3 agonist. For example, tolerance can be induced to specific polypeptides. In one embodiment, immune responses to allergens or foreign polypeptides to which an immune response is undesirable can be inhibited. For example, patients that receive Factor VIII frequently generate antibodies against this clotting factor. Co-administration of an agent that stimulates PD-L3 activity or interaction with its natural binding partner, with recombinant factor VIII (or physically linking PD-L3 to Factor VIII, e.g., by cross-linking) can result in immune response downmodulation.

In one embodiment, a PD-L3 agonist and another agent that can block activity of costimulatory receptors on an immune cell can be used to downmodulate immune responses. Exemplary molecules include: agonists forms of other PD ligands, soluble forms of CTLA-4, anti-B7-1 antibodies, anti-B7-2 antibodies, or combinations thereof. Alternatively, two separate peptides (for example, a PD-L3 polypeptide with blocking forms of B7-2 and/or B7-1 polypeptides), or a combination of antibodies (e.g., activating antibodies against a PD-L3 polypeptide with blocking anti-B7-2 and/or anti-B7-1 monoclonal antibodies) can be combined as a single composition or administered separately (simultaneously or sequentially) to downregulate immune cell mediated immune responses in a subject. Furthermore, a therapeutically active amount of one or more peptides having a PD-L3 polypeptide activity, along with one or more polypeptides having B7-1 and/or B7-1 activity, can be used in conjunction with other downmodulating reagents to influence immune responses. Examples of other immunomodulating reagents include antibodies that block a costimulatory signal (e.g., against CD28 or ICOS), antibodies that activate an inhibitory signal via CTLA4, and/or antibodies against other immune cell markers (e.g., against CD40, CD40 ligand, or cytokines), fusion proteins (e.g., CTLA4-Fc or PD-1-Fc), and immunosuppressive drugs (e.g., rapamycin, cyclosporine A, or FK506). The PD-L3 polypeptides may also be useful in the construction of therapeutic agents which block immune cell function by destruction of cells. For example, portions of a PD-L3 polypeptide can be linked to a toxin to make a cytotoxic agent capable of triggering the destruction of cells to which it binds.

For making cytotoxic agents, polypeptides of the invention may be linked, or operatively attached, to toxins using techniques that are known in the art. A wide variety of toxins are known that may be conjugated to polypeptides or antibodies of the invention. Examples include: numerous useful plant-, fungus- or even bacteria-derived toxins, which, by way of example, include: various A chain toxins, particularly ricin A chain; ribosome inactivating proteins such as saporin or gelonin; alpha-sarcin; aspergillin; restrictocin; and ribonucleases such as placental ribonuclease, angiogenic, diphtheria toxin, or pseudomonas exotoxin. A preferred toxin moiety for use in connection with the invention is toxin A chain which has been treated to modify or remove carbohydrate residues, deglycosylated A chain. (U.S. Pat. No. 5,776,427).

Infusion of one or a combination of such cytotoxic agents (e.g., PD-L3 ricin (alone or in combination with PD-L1-ricin), into a patient may result in the death of immune cells, particularly in light of the fact that activated immune cells that express higher amounts of PD-L3 binding partners. For example, because PD-1 is induced on the surface of activated lymphocytes, a PD-L3 polypeptide can be used to target the depletion of these specific cells by Fc-R dependent mechanisms or by ablation by conjugating a cytotoxic drug (e.g., ricin, saporin, or calicheamicin) to the PD-L3 polypeptide. In one another embodiment, the toxin can be conjugated to an anti-PD-L3 antibody in order to target for death PD-L3-expressing antigen-presenting cell. In a further embodiment, the PD-L3-antibody-toxin can be a bispecific antibody. Such bispecific antibodies are useful for targeting a specific cell population, e.g., using a marker found only on a certain type of cell, e.g., B lymphocytes, monocytes, dendritic cells, or Langerhans cells. Downregulating immune responses by activating PD-L3 activity or the PD-L3-immune cell interaction (and thus stimulating the negative signaling function of PD-L3) is useful in downmodulating the immune response, e.g., in situations of tissue, skin and organ transplantation, in graft-versus-host disease (GVHD), or allergies, or in autoimmune diseases such as systemic lupus erythematosus and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which promotes the activity of PD-L3 or the interaction of PD-L3 with its natural binding partner(s), on immune cells (such as a soluble, multimeric form of a PD-L3 polypeptide) alone or in conjunction with another downmodulatory agent prior to or at the time of transplantation can inhibit the generation of a costimulatory signal. Moreover, promotion of PD-L3 activity may also be sufficient to anergize the immune cells, thereby inducing tolerance in a subject.

To achieve sufficient immunosuppression or tolerance in a subject, it may also be desirable to block the costimulatory function of other molecules. For example, it may be desirable to block the function of B7-1 and B7-2 by administering a soluble form of a combination of peptides having an activity of each of these antigens or blocking antibodies against these antigens (separately or together in a single composition) prior to or at the time of transplantation. Alternatively, it may be desirable to promote inhibitory activity of PD-L3 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers, or soluble forms of other receptor ligand pairs (e.g., agents that disrupt the interaction between CD40 and CD40 ligand (e.g., anti CD40 ligand antibodies)), antibodies against cytokines, or immunosuppressive drugs.

For example, activating PD-L3 activity or the interaction of PD-L3 with its natural binding partner(s), is useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents that promote activity of PD-L3 or PD-L3 interaction with its natural binding partner(s), may induce antigen-specific tolerance of autoreactive immune cells which could lead to long-term relief from the disease. Additionally, co-administration of agents which block costimulation of immune cells by disrupting receptor-ligand interactions of B7 molecules with costimulatory receptors may be useful in inhibiting immune cell activation to prevent production of autoantibodies or cytokines which may be involved in the disease process. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840-856).

Inhibition of immune cell activation is useful therapeutically in the treatment of allergies and allergic reactions, e.g., by inhibiting IgE production. An agent that promotes PD-L3 activity or PD-L3 interaction with its natural binding partner(s) can be administered to an allergic subject to inhibit immune cell-mediated allergic responses in the subject. Stimulation PD-L3 activity or interaction with its natural binding partner(s), can be accompanied by exposure to allergen in conjunction with appropriate MHC molecules. Allergic reactions can be systemic or local in nature, depending on the route of entry of the allergen and the pattern of deposition of IgE on mast cells or basophils. Thus, immune cell-mediated allergic responses can be inhibited locally or systemically by administration of an agent that promotes PD-L3 activity or PD-L3-immune cell interactions.

Inhibition of immune cell activation through stimulation of PD-L3 activity or PD-L3 interaction with its natural binding partner(s), may also be important therapeutically in pathogenic infections of immune cells (e.g., by viruses or bacteria). For example, in the acquired immune deficiency syndrome (AIDS), viral replication is stimulated by immune cell activation. Stimulation of PD-L3 activity may result in inhibition of viral replication and thereby ameliorate the course of AIDS.

Downregulation of an immune response via stimulation of PD-L3 activity or PD-L3 interaction with its natural binding partner(s), may also be useful in treating an autoimmune attack of autologous tissues. Thus, conditions that are caused or exacerbated by autoimmune attack (e.g., heart disease, myocardial infarction or atherosclerosis) may be ameliorated or improved by increasing PD-L3 activity or PD-L3 biding to its natural binding partner. It is therefore within the scope of the invention to modulate conditions exacerbated by autoimmune attack, such as autoimmune disorders (as well as conditions such as heart disease, myocardial infarction, and atherosclerosis) by stimulating PD-L3 activity or PD-L3 interaction with its counter receptor.

4. Upregulation of Immune Responses

Inhibition of PD-L3 activity or PD-L3 interaction with its natural binding partner(s), as a means of upregulating immune responses is also useful in therapy. Upregulation of immune responses can be in the form of enhancing an existing immune response or eliciting an initial immune response. For example, enhancing an immune response through inhibition of PD-L3 activity is useful in cases of infections with microbes, e.g., bacteria, viruses, or parasites, or in cases of immunosuppression. For example, in one embodiment, an agent that inhibits PD-L3 activity, e.g., a non-activating antibody (i.e., a blocking antibody) against PD-L3, or a soluble form of PD-L3, is therapeutically useful in situations where upregulation of antibody and cell-mediated responses, resulting in more rapid or thorough clearance of a virus, bacterium, or parasite, would be beneficial. These conditions include viral skin diseases such as Herpes or shingles, in which case such an agent can be delivered topically to the skin. In addition, systemic viral diseases such as influenza, the common cold, and encephalitis might be alleviated by the administration of such agents systemically. In certain instances, it may be desirable to further administer other agents that upregulate immune responses, for example, forms of B7 family members that transduce signals via costimulatory receptors, in order further augment the immune response.

Alternatively, immune responses can be enhanced in an infected patient by removing immune cells from the patient, contacting immune cells in vitro with an agent that inhibits the PD-L3 activity or PD-L3 interaction with its natural binding partner(s), and reintroducing the in vitro-stimulated immune cells into the patient. In another embodiment, a method of enhancing immune responses involves isolating infected cells from a patient, e.g., virally infected cells, transfecting them with a nucleic acid molecule encoding a form of PD-L3 that cannot bind its natural binding partner(s), such that the cells express all or a portion of the PD-L3 molecule on their surface, and reintroducing the transfected cells into the patient. The transfected cells may be capable of preventing an inhibitory signal to, and thereby activating, immune cells in vivo.

A agent that inhibits PD-L3 activity or PD-L3 interaction with its natural binding partner(s), can be used prophylactically in vaccines against various polypeptides, e.g., polypeptides derived from pathogens. Immunity against a pathogen, e.g., a virus, can be induced by vaccinating with a viral polypeptide along with an agent that inhibits PD-L3 activity, in an appropriate adjuvant. Alternately, a vector comprising genes which encode for both a pathogenic antigen and a form of PD-L3 that blocks PD-L3 interaction with immune cells can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) J. Biotechnol. 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubert (1997) Proc Natl. Acad. Sci. USA 94:961). Attenuated microorganisms can be used for delivery to mucosal surfaces (Sizemore et al. (1995) Science 270:29).

In another embodiment, the antigen in the vaccine is a self-antigen. Such a vaccine is useful in the modulation of tolerance in an organism. Immunization with a self antigen and an agent that blocks PD-L3 activity or PD-L3 interaction with its natural binding partner can break tolerance (i.e., interfere with tolerance of a self antigen). Such a vaccine may also include adjuvants such as alum or cytokines (e.g., GM-CSF, IL-12, B7-1, or B7-2). In one embodiment, an agent which inhibits PD-L3 activity or PD-L3 interaction with its natural binding partner(s), can be administered with class I MHC polypeptides by, for example, a cell transfected to coexpress a PD-L3 polypeptide or blocking antibody and MHC class I .alpha. chain polypeptide and beta2 microglobulin to result in activation of T cells and provide immunity from infection. For example, viral pathogens for which vaccines are useful include: hepatitis B, hepatitis C, Epstein-Barr virus, cytomegalovirus, HIV-1, HIV-2, tuberculosis, malaria and schistosomiasis.

In another application, inhibition of PD-L3 activity or PD-L3 interaction with its natural binding partner(s), can be useful in the treatment of tumor immunity. Tumor cells (e.g., sarcoma, melanoma, lymphoma, leukemia, neuroblastoma, or carcinoma) can be transfected with a nucleic acid molecule that inhibits PD-L3 activity. These molecules can be, e.g., nucleic acid molecules which are antisense to PD-L3, or can encode non-activating anti-PD-L3 antibodies. These molecules can also be the variable region of an anti-PD-L3 antibody. If desired, the tumor cells can also be transfected with other polypeptides which activate costimulation (e.g., B7-1 or B7-2). The transfected tumor cells are returned to the patient, which results in inhibition (e.g., local inhibition) of PD-L3 activity Alternatively, gene therapy techniques can be used to target a tumor cell for transfection in vivo.

Stimulation of an immune response to tumor cells can also be achieved by inhibiting PD-L3 activity or PD-L3 interaction with its natural binding partner(s), by treating a patient with an agent that inhibits PD-L3 activity or PD-L3 interaction with its natural binding partner(s). Preferred examples of such agents include, e.g., antisense nucleic acid molecules, antibodies that recognize and block PD-L3, and compounds that block the interaction of PD-L3 with its naturally occurring binding partner(s) on an immune cell (e.g., soluble, monovalent PD-L3 molecules; soluble forms of PD-L3 molecules that do not bind to Fc receptors on antigen presenting cells; soluble forms of PD-L3 binding partner(s); and compounds identified in the subject screening assays). In addition, tumor cells which lack MHC class I or MHC class II molecules, or which fail to express sufficient amounts of MHC class I or MHC class II molecules, can be transfected with nucleic acid encoding all or a portion of (e.g., a cytoplasmic-domain truncated portion) of an MHC class I .alpha. chain polypeptide and beta2 microglobulin polypeptide or an MHC class II .alpha. chain polypeptide and an MHC class II .beta. chain polypeptide to thereby express MHC class I or MHC class II polypeptides on the cell surface. Expression of the appropriate class I or class II MHC in conjunction with an PD-L3 inhibiting polypeptide or antisense nucleic acid induces a T cell mediated immune response against the transfected tumor cell. Optionally, a gene encoding an antisense construct which blocks expression of an MHC class II-associated polypeptide, such as the invariant chain, can also be cotransfected with a DNA encoding a PD-L3 inhibiting polypeptide or antisense nucleic acid to promote presentation of tumor associated antigens and induce tumor specific immunity. Expression of B7-1 by B7-negative murine tumor cells has been shown to induce T cell mediated specific immunity accompanied by tumor rejection and prolonged protection to tumor challenge in mice (Chen, L. et al. (1992) Cell 71:1093-1102; Townsend, S. E. and Allison, J. P. (1993) Science 259:368-370; Baskar, S. et al. (1993) Proc Natl. Acad. Sci. 90:5687-5690). Thus, the induction of an immune cell-mediated immune response in a human subject can be sufficient to overcome tumor-specific tolerance in the subject.

In another embodiment, the immune response can be stimulated by the inhibition of PD-L3 activity or PD-L3 interaction with its natural binding partner(s), such that preexisting tolerance is overcome. For example, immune responses against antigens to which a subject cannot mount a significant immune response, e.g., tumor-specific antigens, can be induced by administering an agent that inhibits the activity of PD-L3 activity or the ability of PD-L3 to bind to its natural binding partner, can be used as adjuvants to boost responses to foreign antigens in the process of active immunization.

In one embodiment, immune cells are obtained from a subject and cultured ex vivo in the presence of an agent that that inhibits PD-L3 activity or PD-L3 interaction with its natural binding partner(s), to expand the population of immune cells. In a further embodiment the immune cells are then administered to a subject. Immune cells can be stimulated to proliferate in vitro by, for example, providing the immune cells with a primary activation signal and a costimulatory signal, as is known in the art. Various forms of PD-L3 polypeptides or agents that inhibit PD-L3 activity can also be used to costimulate proliferation of immune cells. In one embodiment, immune cells are cultured ex vivo according to the methods described in PCT Application No. WO 94/29436. The costimulatory molecule can be soluble, attached to a cell membrane or attached to a solid surface, such as a bead.

In an additional embodiment, in performing any of the methods described herein, it is within the scope of the invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that inhibits PD-L3 activity or PD-L3 interaction with its natural binding partner(s).

E. Identification of Cytokines Modulated by Modulation of PD-L3 Activity or PD-L3-Interactions with its Counter Receptor on T Cells The PD-L3 molecules described herein can be used to identify cytokines which are produced by or whose production is enhanced or inhibited in immune cells in response to modulation of PD-L3 activity or PD-L3 interaction with its natural binding partner(s). Immune cells can be suboptimally stimulated in vitro with a primary activation signal, for example, T cells can be stimulated with phorbol ester, anti-CD3 antibody or preferably, antigen, in association with an MHC class II molecule, and given a costimulatory signal, e.g., by a stimulatory form of B7 family antigen, for instance by a cell transfected with nucleic acid encoding a B7 polypeptide and expressing the peptide on its surface, or by a soluble, stimulatory form of the peptide. The cells can then be contacted with cells expressing PD-L3 (e.g., antibodies against PD-L3 Known cytokines released into the media can be identified by ELISA or by the ability of an antibody which blocks the cytokine to inhibit immune cell proliferation or proliferation of other cell types that are induced by the cytokine. For example, an IL-4 ELISA kit is available from Genzyme (Cambridge, Mass.), as is an IL-7 blocking antibody. Blocking antibodies against IL-9 and IL-12 are available from Genetics Institute (Cambridge, Mass.). The effect of stimulating or blocking PD-L3 activity or the interaction of PD-L3 and its binding partner(s) on the cytokine profile can then be determined. As noted supra and shown in the examples PD-L3 apparently suppresses the expression of IL-2 and gamma interferon by immune cells.

An in vitro immune cell costimulation assay as described above can also be used in a method for identifying novel cytokines which can be modulated by modulation of PD-L3 activity. For example, where stimulation of the CD28/CTLA4 pathway seems to enhance IL-2 secretion, stimulation of the ICOS pathway seems to enhance IL-10 secretion (Hutloff et al. (1999) Nature 397:263). If a particular activity induced upon costimulation, e.g., immune cell proliferation, cannot be inhibited by addition of blocking antibodies to known cytokines, the activity may result from the action of an unknown cytokine. Following costimulation, this cytokine can be purified from the media by conventional methods and its activity measured by its ability to induce immune cell proliferation.

To identify cytokines which may play a role the induction of tolerance, an in vitro T cell costimulation assay as described above can be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance can be targeted for blockage in vivo in conjunction with reagents which block B lymphocyte antigens as a more efficient means to induce tolerance in transplant recipients or subjects with autoimmune diseases. For example, one could administer a cytokine blocking antibody to a subject along with an agent that promotes PD-L3 activity or PD-L3 interaction with a binding partner.

Thus, to summarize a novel member of the Programmed Death Ligand (PDL) family has now been identified which is expressed by Treg cells. This novel protein has been designated PD-L3. The receptors of this PD-L family are type I transmembrane proteins containing a single IgV domain, while the ligands are type I transmembrane proteins expressing both an IgV and an IgC extracellular domains. Like other members of the PDL family, PD-L3 co-stimulates αCD3 proliferation of T cells in vitro. In addition, the expression of PD-L3 is increased in αCD3 activated Treg and reduced in the presence of αGITR.

A second, TNF-like, protein has also been identified as being upregulated upon αCD3/αGITR stimulation. This protein has been designated Treg-sTNF. These proteins may be involved in contact-dependent and paracrine suppression of immunity and therefore are useful for modulating (e.g., inhibiting or stimulating) an immune response and in the treatment of diseases and conditions involving Treg signaling. For example, the PD-L3 protein can be used as a co-stimulatory signal for stimulating or enhancing immune cell activation. PD-L3 proteins and PD-L3 binding agents and PD-L3 agonists and antagonists are especially useful in treating immune conditions wherein regulation of T cell immunity is desired, e.g., modulation of T cell activation, differentiation and proliferation, and in particular modulation of CD4+ and CD8+ T cell proliferation, cytokine production, and T cell responses during cognate interactions between T cells and myeloid derived APCs.

This invention is further illustrated by the following examples, which should not be construed as limiting. The contents of all references, patents, and published patent applications cited throughout this application, as well as the Figures and Sequence Listing, are incorporated herein by reference.

EXAMPLES

The following Materials and Methods were used in the examples which follow: Materials and Methods
Expression Profiling To facilitate comparisons with established expression profiles of Treg cells, standard growth and activation conditions were employed (McHugh, et al. (2002) supra). Briefly, fresh isolated Treg cells (~96% positive) were inoculated at 106/mL into complete RPMI medium supplemented with 10% fetal bovine serum and 100 units IL-2 in a 24-well plate precoated with anti-CD3 with or without anti-GITR (DTA-1) (Shimizu, et al. (2002) supra). The cells were cultured at 37° C. for 0 and 12 hours, RNA was purified and subsequently analyzed using an Affymetrix® mouse genome A430 oligonucleotide array.

By comparing the data from resting or activated CD4+ CD25+ T cell groups, gene expression patterns were found to be similar to those established in the art (Gavin, et al. (2002) supra; McHugh, et al. (2002) supra). To identify genes regulated by GIRT signaling, gene expression profiles were compared between the different cell populations with or without anti-GITR treatment. A list of known as well as unknown genes were compiled including the previously uncharacterized PD-L3 and Treg-sTNF.

Mice

C57BL/6 mice, and OTII CD4 transgenic mice were purchased from the Jackson Laboratory. FoxP3-GFP reporter mice were as previously described Fontenot, J. D., Rasmussen, J. P., Williams, L. M., Dooley, J. L., Farr, A. G., and Rudensky, A. Y. (2005). Regulatory T cell lineage specification by the forkhead transcription factor foxp3. Immunity 22, 329-341 and were generously provided by Alexander Rudensky, University of Washington School of Medicine, Seattle, Wash. PD-1 KO mice were generously provided by Dr. Tasuku Honjo (Kyoto University, Japan) Nishimura, H., Nose, M., Hiai, H., Minato, N., and Honjo, T. (1999). Development of lupus-like autoimmune diseases by disruption of the PD-1 gene encoding an ITIM motif-carrying immunoreceptor. Immunity 11, 141-151; Nishimura, H., Okazaki, T., Tanaka, Y., Nakatani, K., Hara, M., Matsumori, A., Sasayama, S., Mizoguchi, A., Hiai, H., Minato, N., and Honjo, T. (2001). Autoimmune dilated cardiomyopathy in PD-1 receptor-deficient mice. Science 291, 319-322. All animals were maintained in a pathogen-free facility at Dartmouth Medical School.

Abs, Cell Lines, and Reagent:

Antibodies αCD3 (2C11), αCD28 (PV-1), αCD4 (GK1.5), αCD8 (53-6.7), αCD11b (M1/70), αF4/80 (BM8), αCD11c (N418), αNK1.1 (PK136), αGr1 (RB6-8C5), αPD-L1 (MIN5), αPD-L2 (TY25), αB7-H3 (M3.2D7), αB7-H4 (188) were purchased from Ebioscience. LPS (Sigma), recombinant murine IFN . . . Peprotech), human IL-2 (Peprotech), soluble PD-L1-Ig fusion protein (R&D systems) were used at indicated concentrations. Complete Freund's adjuvant (CFA) and chicken ovalbumin (OVA) were purchased from Sigma. The CHO cell line expressing MHCII molecule I-Ad and costimulatory molecule B7-2 was kindly provided by Dr. Arlene Sharpe (Harvard Medical School).

Molecular Cloning of PD-L3, Retrovirus Production and Retroviral Transduction of Cells Full length PD-L3 was cloned from purified murine CD4+ T cells. Total RNA was isolated from CD4+ T cells using Qiagen RNAmini kit. cDNA was generated using Bio-Rad iScript™ cDNA synthesis kit. Full-length PD-L3 was amplified and cloned into the ECORI-XhoI site of a retroviral vector pMSCV-IRES-GFP Zhang, X., and Ren, R. (1998). Bcr-Abl efficiently induces a myeloproliferative disease and production of excess interleukin-3 and granulocyte-macrophage colony-stimulating factor in mice: a novel model for chronic myelogenous leukemia. Blood 92, 3829-3840, in which the IRES-GFP fragment was replaced by RFP, thus resulting in a fusion protein of PD-L3 fused to the N-terminus of RFP. Helper free retroviruses were generated in HEK293T cells by transient transfection of the PD-L3-RFP retroviral vector together with an ecotrophic packaging vector pCL-Eco (IMGENEX corp.). Retroviral transduction of murine T cell line EL4 cells, or bone marrow derived DCs were carried out by spin infection at 2000 rpm at RT for 45 min in the presence of 8 µg/ml polybrene (Sigma).

Production of PD-L3-Ig Fusion Protein

The extracellular domain of PD-L3 (amino acid 32-190) was amplified and cloned into the SpeI-BamHI sites of the parental vector CDM7B Hollenbaugh, D., Douthwright, J., McDonald, V., and Aruffo, A. (1995). J Immunol Methods 188, 1-7.... This vector contains the mutant form of constant and hinge regions of human IgG1, which has much reduced binding to Fc receptors. The resulting vector CDM7B-PD-L3 was co-transfected with a DHFR expression vector pSV-dhfr (McIvor, R. S., and Simonsen, C. C. (1990)). Nucleic Acids Res 18, 7025-7032 into the CHO (dhfr-) cell line (ATCC #CRL-9096). Stable CHO cell clones that express PD-L3-Ig were selected in medium MEM-alpha w/o nucleotides (Invitrogen). Further amplification with 0.5-1 µM methotrexate (Sigma M9929) yielded clones expressing high levels of soluble PD-L3-Ig fusion protein. The fusion protein was further purified from culture supernatant using standard protein-G column affinity chromatography.

Generation of PD-L3 Monoclonal Antibodies

Armenian hamsters were immunized 4× times with EL4 cells over-expressing PD-L3-RFP weekly, then boosted with PD-L3-Ig fusion protein emulsified in CFA. Four weeks after the boost, hamsters were boosted again with soluble PD-L3-Ig fusion protein. Four days after the last boost, hamster spleen cells were harvested and fused to the myeloma cell line SP2/0-Ag14 (ATCC #CRL-1581) using standard hybridoma fusion techniques Shulman, M., Wilde, C. D., and Kohler, G. (1978). A better cell line for making hybridomas secreting specific antibodies. Nature 276, 269-270. Hybridoma clones that secret PD-L3 specific antibodies were selected after limiting dilution and screened by both ELISA and flow cytometric methods.

RNA and RT-PCR

Total RNA from various mouse tissue samples or purified hematopoietic cell types were collected by using Trizol™ (Invitrogen) method following company's instructions. cDNAs were prepared by using the iScript™ cDNA synthesis kit (Bio-Rad). Equal amount of tissue cDNAs (10 ng) were used for RT-PCR reactions to amplify full-length PD-L3. PCR products were viewed after running through a 1% agarose gel.

Flow Cytometry

Flow cytometry analysis was performed on FACSCAN using CellQuest software (BD Bioscience). Data analysis was performed using FlowJo software (Treestar).

Cell Preparation

Total CD4+ T cells were isolated from naïve mice using total CD4+ T cell isolation kit (Miltenyi). When indicated, enriched CD4+ T cells were flow sorted into naïve (CD44low CD25-CD62Lhi) and memory (CD44hi CD25-CD62Llow) populations. For in vitro proliferation assays, CD4+ T cells were labeled with 5 uM CFSE (Molecular Probes) for 10 min at 37 C, and washed twice before being stimulated.

In Vitro Plate-Bound T Cell Activation Assay

Purified CD4+ T cells (100,000 cells per well) were cultured in 96× flat-bottom well plates, in the presence of anti-CD3 (clone 2C11) and either PD-L3-Ig or control-Ig at indicated concentration ratios. For example, for a full-range titration, the 96-well plates were coated with 2.5 µg/ml of αCD3 mixed together with 1.25 µg/ml (ratio 2:1), 2.5 µg/ml (ratio 1:1), 5 µg/ml (ratio 1:2), or 10 µg/ml (ratio 1:4) PD-L3-Ig or control-Ig protein in PBS at 4° C. overnight. Wells were washed 3 times with PBS before adding CD4+ T cells. Replicate cultures were in complete RPMI 1640 medium supplemented with 10% FBS, 10 mM HEPES, 50 µM β-ME, Penicillin/Streptomycin/L-Glutamine. When indicated, either 100 U/ml human IL-2 (PeproTech) or titrated amount of CD28 (clone PV-1, Bio X cell) were coated together with CD3 to rescue the inhibitory effects of PD-L3-Ig. Cultures were analyzed on day 3 for CFSE profiles, or according to a time course as indicated.

Culture of Bone Marrow Derived DCS, Retroviral Transduction, and Stimulation of Transgenic CD4+ T Cells Bone marrow derived DCs were generated as described Lutz, M. B., Kukutsch, N., Ogilvie, A. L., Rossner, S., Koch, F., Romani, N., and Schuler, G. (1999). An advanced culture method for generating large quantities of highly pure dendritic cells from mouse bone marrow. J Immunol Methods 223, 77-92; Son, Y. I., Egawa, S., Tatsumi, T., Redlinger, R. E., Jr., Kalinski, P., and Kanto, T. (2002). A novel bulk-culture method for generating mature dendritic cells from mouse bone marrow cells. J Immunol Methods 262, 145-157 with some modifications. Briefly, on day 0, bone marrow cells were isolated from tibia and femur by flushing with 27 G needle. After red blood cell lysis, 1-2×106 bone-marrow cells were resuspended in 1 ml complete RPMI 1640 medium containing 20 ng/ml GM-CSF (Peprotech Inc), in 6× well cell culture plates (Nunc, Inc.). 2 ml supernatant containing either RFP or PD-L3-RFP retrovirus was added to the bone marrow cells. Polybrene (Sigma) was also added at a final concentration 8 µg/ml. Infection was carried out by spinning the plate at 2000 rpm for 45 min at RT. Cells were then cultured for another 2 hours before fresh medium were added. Similar infection procedure was repeated on day+1, day+3, day+5, and day+7. Loosely adherent cells (90% are CD11c+) were collected on day+10 and CD11c+RFP+ double positive cells were sorted and used to stimulate transgenic OT-II CD4+ T cells. For OT-II T cell proliferation assays, 100,000 CFSE-labeled OT-II CD4+ T cells were cultured in 96 well round-bottom plates with 30,000 sorted RFP+ or PD-L3-RFP+BM-DCs, in the presence of titrated amount of synthetic OVA323-339 peptide (Anaspec). Proliferation of OT-II T cells were analyzed at 72 hrs by examining CFSE profiles.

Expression Studies of PD-L3 in Response to Immunization

To immunize transgenic mice DO11.10, 300 µg OVA (Sigma) were emulsified in CFA (200 µl), and injected subcutaneously into the flanks of mice. The draining and non-draining inguinal lymph nodes were harvested at indicated time points. Single cell suspensions were prepared and analyzed for the expression of PD-L3 and other surface markers by flow cytometry.

Inhibitory Activity of PD-L3.

The inhibitory activity of PD-L1 was revealed by using antigen presenting cells over-expressing PD-L1 in vitro with CD4+ and CD8+ T cell antigen receptor transgenic T cells and antigen stimulation (Carter, et al. (2002) Eur. J. Immunol. 32:634-43). Similarly, the lentivector disclosed herein, which expresses the full-length PD-L3, is transduced into cell lines expressing class II major histocompatibility complex (MHC) and class I MHC. The response of TEa Tg or the 2C transgenic T cells to antigen presented by empty vector-transduced or PD-L3-transduced antigen presenting cells is determined according to established methods.

Protein Expression.

Expression patterns in lymphoid, monocyte and dendritic cell subsets, as well as non-hemoatopoietic tissues, is determined by RT-PCR and western blot analysis using standard protocols in combination with the rabbit αPD-L3 antibody disclosed herein.

Monoclonal Antibody Production.

PD-L3 was overexpressed in the murine B cell line A20, and the recombinant cell line was used to immunize Armenian hamsters. After 5× cell immunization, hamsters were boosted with purified PD-L3-Ig fusion protein emulsified in CFA. Four weeks later, a final boost was provided with soluble PD-L3-Ig. Subsequently, fusions of hamster splenocytes with SP2/0 cells were performed on day 4. Sixteen different clones were identified that recognized PD-L3-Ig fusion protein by ELISA, as well as stained PD-L3 but not PD-L1 overexpressed on the murine T cell line EL4. Eleven of the clones were successfully subcloned and prepared for evaluation of their ability to stain endogenous PD-L3 on cells and tissues, and to block PD-L3 functions.

Proliferation Assays:

In vitro CD4 T cell proliferation assays was designed to screen PD-L3 mAb activity. In this assay, T cells were stimulated by immobilized anti-CD3 in microplate wells, which crosslinks T cell receptors. Using a PD-L3-ig fusion protein, which is composed of the extracellular domain of PD-L3 fused to the Fc portion of human IgG, the activity of PD-L3 mAb was detected in two different configurations. First, when mAb was co-immobilized with αCD3, it potently inhibited T cell proliferation, only in the presence of added soluble PD-L3-Ig fusion protein. This activity was dependent upon the ability of PD-L3-Ig to bind to the immobilized mAb in the well. Using this form of the assay, clones were identified that were of high, intermediate or low suppressive activity. Second, when mAb was added as a soluble reagent to the assay, it exerted potent suppressive activity on T cell proliferation, by synergizing with the immobilized PD-L3-Ig fusion protein. In this form of assay, clones were identified that were of various suppressive activities.

Example 1

Cloning and Sequence Analysis of PD-L3

PD-L3 and Treg-sTNF were identified by global transcriptional profiling of resting Treg, Treg activated with αCD3, and Treg activated with αCD3/αGITR. αGITR was selected for this analysis as triggering of GITR on Treg has been shown to extinguish their contact-dependent suppressive activity (Shimizu, et al. (2002) supra). PD-L3 and Treg-sTNF were identified on AFFIMETRIX® DNA arrays based on their unique expression patterns (Table 1). PD-L3 exhibited an increase in expression in αCD3 activated Treg and reduced expression in the presence of αGITR; and Treg-sTNF exhibited a αCD3/αGITR-dependent increase in expression.

Purified CD4+CD25+ T cells were stimulated in culture overnight with none, αCD3, or αCD3/αGITR, and RNA isolated for real-time PCR analysis. Expression listed is relative to actin.

TABLE 1

| mRNA | Relative Expression | | |
|---|---|---|---|
| | None | αCD3 | αCD3/αGITR |
| PD-L3 | 6 | 10 | 7 |
| T$^{reg}$-sTNF | 0.2 | 0.3 | 1.5 |

As shown by the results in FIG. 1A-1D Affymetrix analysis of activated vs. resting CD25+ CD4+ nTregs revealed the expression of a gene product (RIKEN cDNA 4632428N05, or 4632428N05Rik) with unknown function but with sequence homology to the Ig superfamily.

More specifically, a 930 bp gene product was cloned from the CD4+ T cell cDNA library, which matched the predicted size and sequence. Silico-sequence and structural analysis predicts a transmembrane protein of 309 amino acids upon maturation, with an extracellular domain of 159 amino acids, a transmembrane domain of 22 amino acids and a cytoplasmic tail of 95 amino acids (FIG. 1A). Amino acid sequence alignment reveals an extracellular Immunoglobulin (Ig)-V like domain homologous to B7 family ligands such as PD-L1, PD-L2, B7-H3 and B7-H4, as well as to the B7 family receptors (i.e. PD-1, CTLA-4, CD28, BTLA, ICOS) (FIG. 1B-C). Although the sequence identity of the Ig-V domains between B7 family ligands and receptors in general is not very high (<40%), the Ig-V domain of 4632428N05Rik bears the highest homology with B7 family ligands PD-L1 and PD-L2. Sequence alignment also reveals several highly conserved cysteines (FIG. 1B) that are important for intra-chain disulfide bond formation, which is characteristic of the B7 family ligands Sica et al., (2003). Immunity 18, 849-861.

The extracellular domain of 4632428N05Rik contains only the Ig-V domain but lacks the Ig-C domain (FIG. 1B-C). This unique feature is characteristic of the B7 family receptors, and distinguishes 4632428N05Rik from all other B7 family ligands, which contain both Ig-V and Ig-C domains Freeman, G. J. (2008). Proc Natl Acad Sci USA 105, 10275-10276; Lazar-Molnar et al., (2008). Proc Natl Acad Sci USA 105, 10483-10488; Lin et al., (2008), Proc Natl Acad Sci USA 105, 3011-3016; Schwartz et al., (2001), Nature 410, 604-608; Stamper et al., (2001), Nature 410, 608-61. Consistently, the phylogenic analysis using PhyML algorithm (Phylogenetic Maximum Likelihood) placed 4632428N05Rik in a closer evolutionary distance with B7 family receptors, in particular with PD-1, than the B7 family ligands (FIG. 2) Guindon, S., and Gascuel, O. (2003). A simple, fast, and accurate algorithm to estimate large phylogenies by maximum likelihood. Syst Biol 52, 696-704. However, the cytoplasmic tail of PD-L3 does not contain any signaling domains (e.g. ITIM, ITAM or ITSM), which are the signature domains of B7 family receptors Sharpe, A. H., and Freeman, G. J. (2002). The B7-CD28 superfamily. Nat Rev Immunol 2, 116-126. It is therefore hypothesized that despite its close evolutionary relationship with the inhibitory receptor PD-1, 4632428N05Rik represents a novel member of the B7 ligand family. Based on these structural and phylogenic characteristics, this molecule was named PD-1-eXpressed as Ligand (PD-L3). PD-L3 is also highly conserved between the mouse and human orthologs, sharing 77% sequence identity (FIG. 1D).

The nucleic acid sequence encoding mouse PD-L3 is set forth herein as SEQ ID NO:1 and the mouse PD-L3 protein sequence is set forth as SEQ ID NO:2.

The human homolog of PD-L3 is located on chromosome 10 (72.9 Mb) and composed of 6 exons thereby generating a transcript of 4689 bases in length coding for a 311 residue protein. The human homolog mRNA coding sequence is provided in GENBANK accession number NM_022153 and protein sequence give as NP_071436. The nucleic acid sequence encoding human PD-L3 is set forth herein as SEQ ID NO:3 and the human PD-L3 protein sequence is set forth as SEQ ID NO:4. Mouse and human genes share 74% homology and are 68% identical at the protein level. Homologs were also identified in *Rattus norvegicus* on chromosome 20 (27.7 Mb; GENBANK accession number BC098723), as well as *Fugu rubripes* and *Danio rerio*. In particular embodiments, PD-L3 proteins of the present share the common amino acid sequence set forth in SEQ ID NO:5.

Example 2

Expression Studies of PD-L3 by RT-PCR Analysis and Flow Cytometry

Figure 3A:
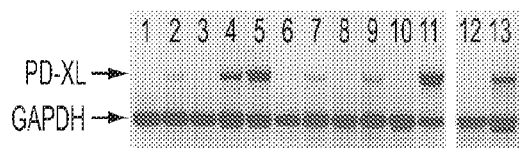
Figure 3B:
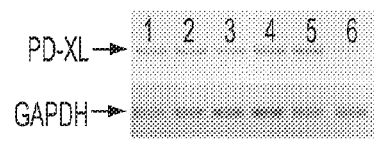

As shown in the experiments in FIG. 3, RT-PCR analysis was used to determine the mRNA expression pattern of PD-L3 in mouse tissues (FIG. 3A). PD-L3 is mostly expressed on hematopoietic tissues (spleen, thymus, bone marrow), or tissues with ample infiltration of leukocytes (i.e. lung). Weak expression was also detected in non-hematopoietic tissues (i.e. heart, kidney, brain, and ovary). Analysis of several hematopoietic cell types reveals expression of PD-L3 on peritoneal macrophages, splenic CD11b+ monocytes, CD11c+ DCs, CD4+ T cells and CD8+ T cells, but lower expression level on B cells (FIG. 3B). This expression pattern is also largely consistent with the GNF (Genomics Institute of Novartis Research Foundation) gene array database Su et al., (2002), Proc Natl Acad Sci USA 99, 4465-4470, as well as NCBI GEO (gene expression omnibus) database (FIG. 4).

In order to study the protein expression, PD-L3 specific hamster monoclonal antibodies were produced. The specificity is demonstrated by positive staining on PD-L3-overexpressing murine EL4 T cells, but negative staining on PD-L1-overexpressing EL4 cells (FIG. 5).

Both polyclonal and monoclonal antibodies were raised against PD-L3. Using a rabbit anti-PD-L3 antibody, PD-L3 protein was localized to lymphoid organs and prominently found in brain tissue. Of the monoclonal antibodies identified, the specificity of αPD-L3 clone 8D8 was further evaluated. In this analysis, clone 8D8 was tested for binding against a panel of PD-L like-Ig fusion protein molecules including CTLA-4, PD-1, PD-L1, PD-L2, B7-1, B7-2, PD-L3 and hIg. The results of this analysis indicated that 8D8 αPDL-3 was highly specific for PD-L3.

Figure 3C:
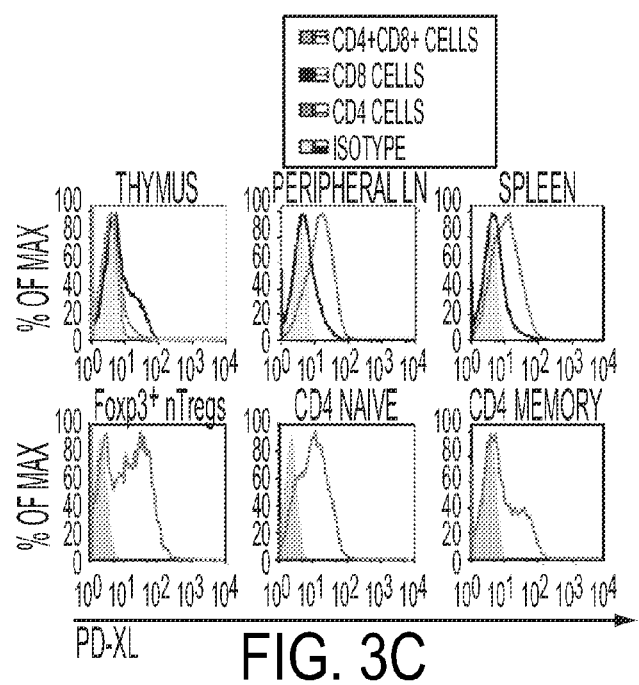
Figure 3D:
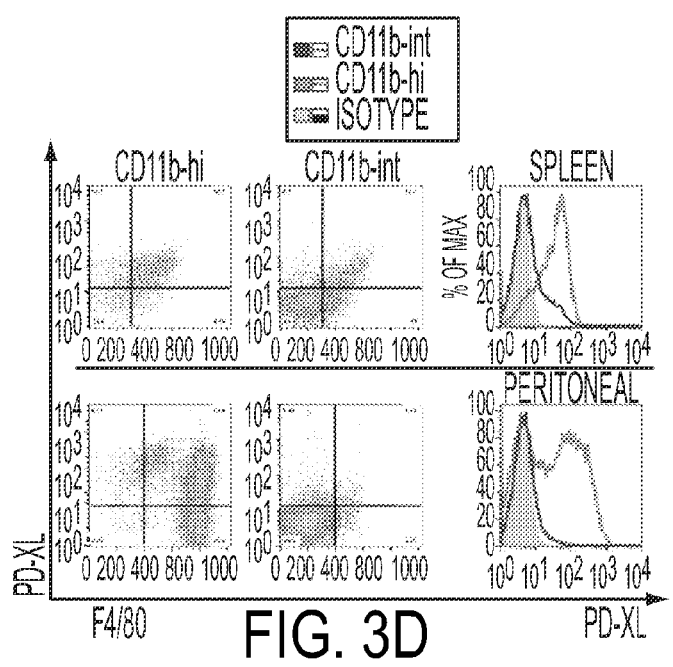
Figure 3E:
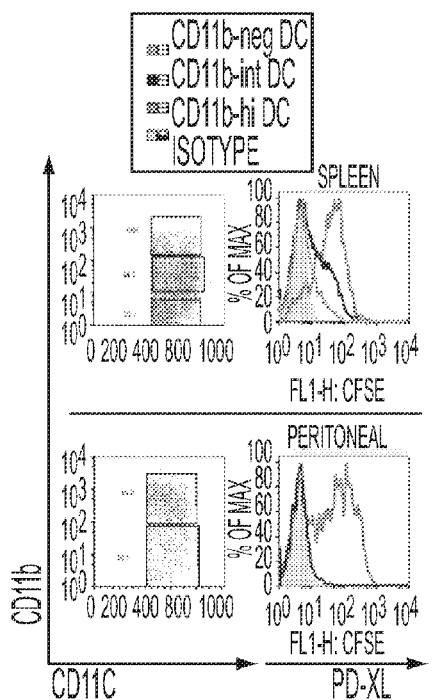
Figure 3F:
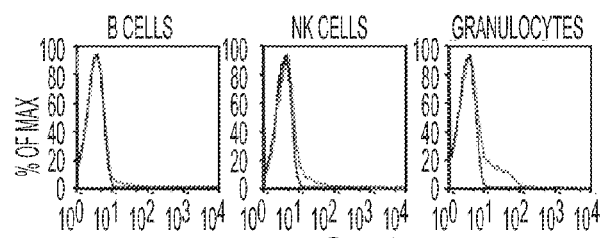

Specifically, using the anti-PD-L3 mAb clone 8D8, PD-L3 expression was analyzed on hematopoietic cells by flow cytometry. Foxp3GFP knock-in reporter mice were used to distinguish CD4+ nTregs (34). In peripheral lymphoid organs (spleen and lymph nodes), significant expression is seen on all CD4+ T cell subsets (see total CD4+ T cells, or Foxp3- naïve T cells and Foxp3+ nTreg cells, and memory CD4+ T cells), whereas CD8+ T cells express markedly lower amount of surface PD-L3 (FIG. 3C). In thymus, PD-L3 expression is negative on CD4+CD8+ double positive thymocytes, low on CD4 single positive cells, and detectable on CD8 single positive cells. Next, a strong correlation of high PD-L3 expression with CD11b marker can be seen for both splenic and peritoneal cells, including both F4/80 macrophages and myeloid CD11c+DCs (FIG. 3D-E). On the other hand, B cells and NK cells are mostly negative for PD-L3 expression. A small percentage of Gr11+ granulocytes also express PD-L3 (FIG. 3F).

Figure 3G:
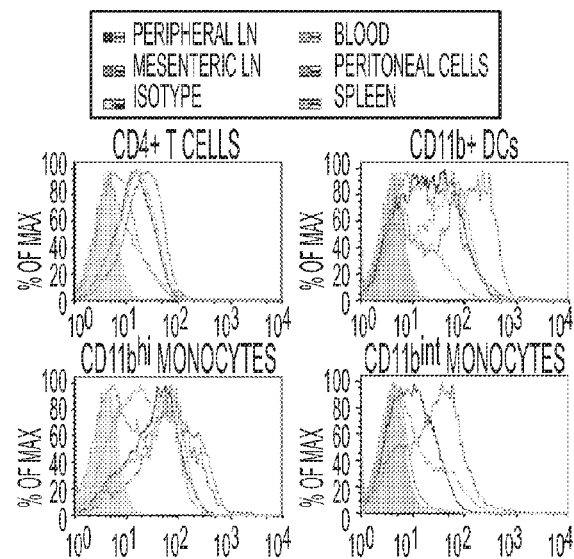
Figure 4A:
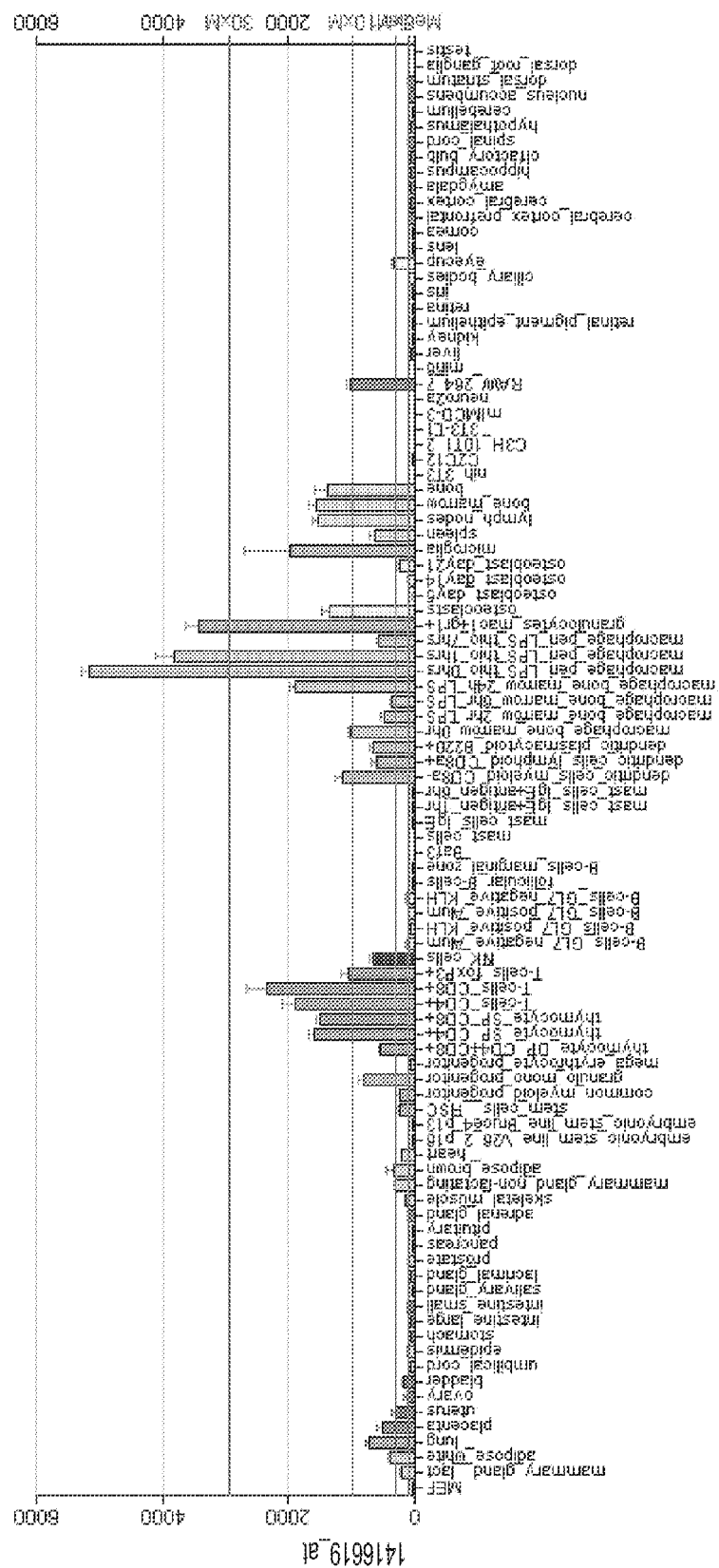
Figure 4B:
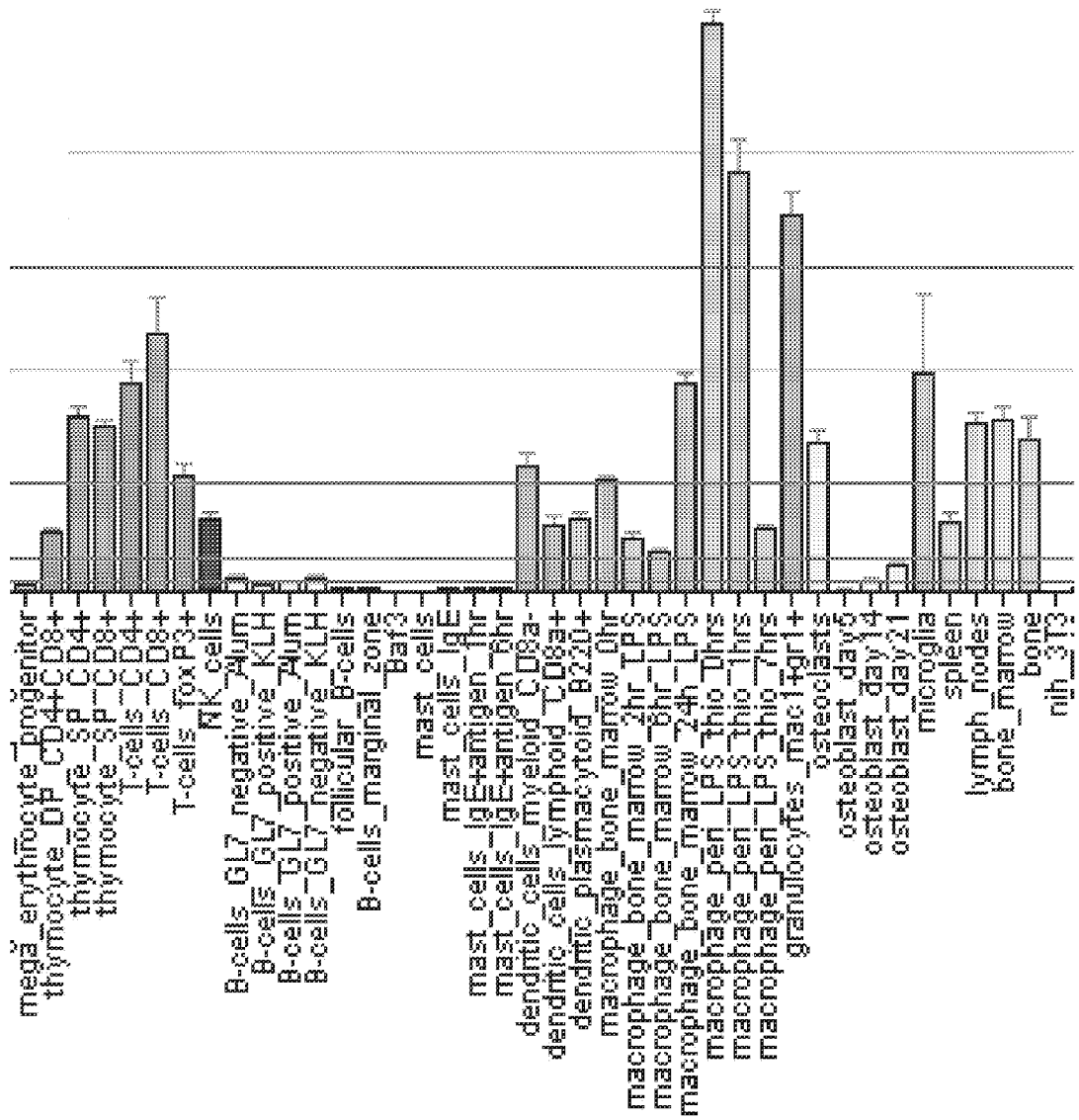
Figure 4C:
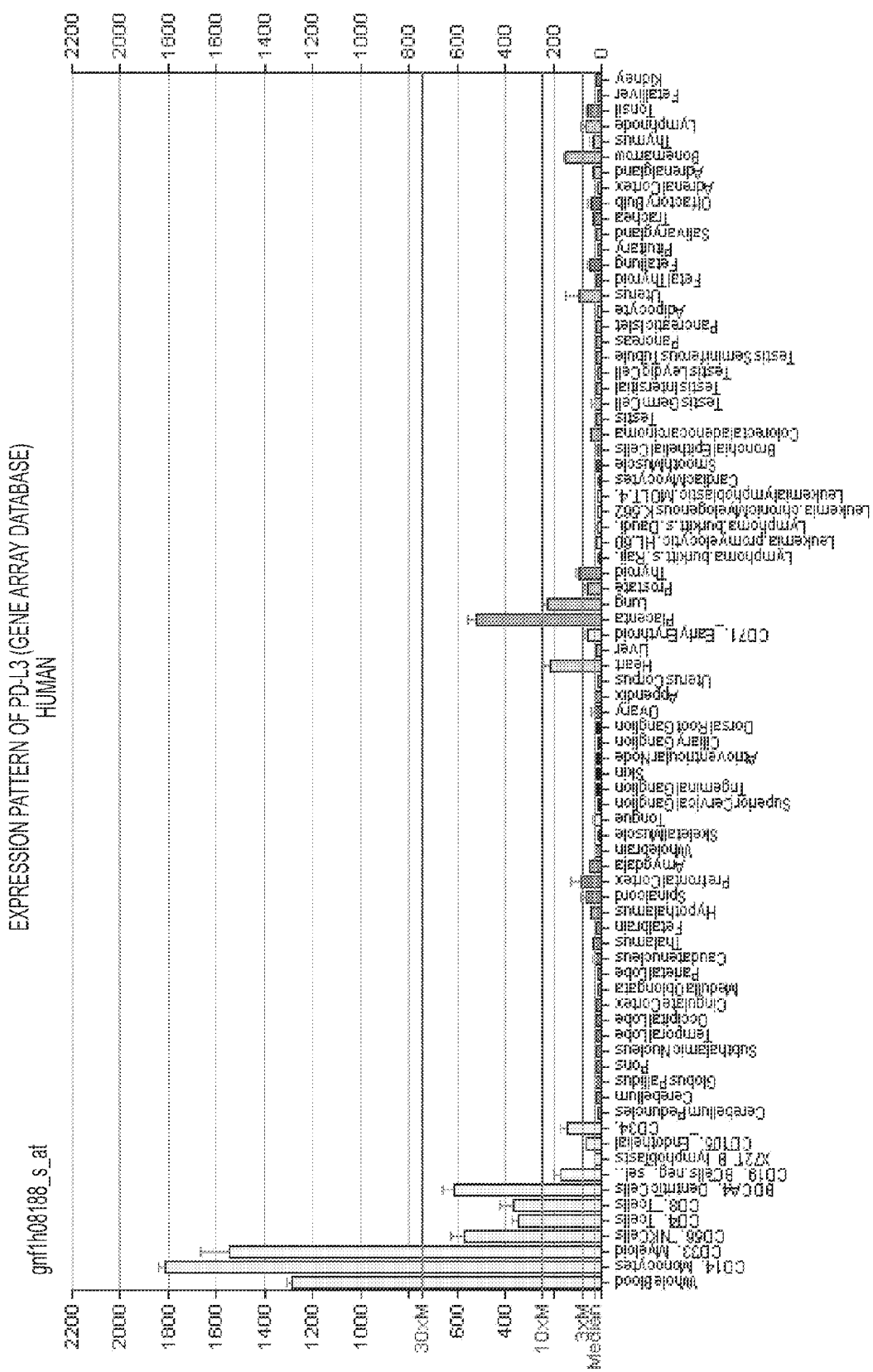
Figure 4D:
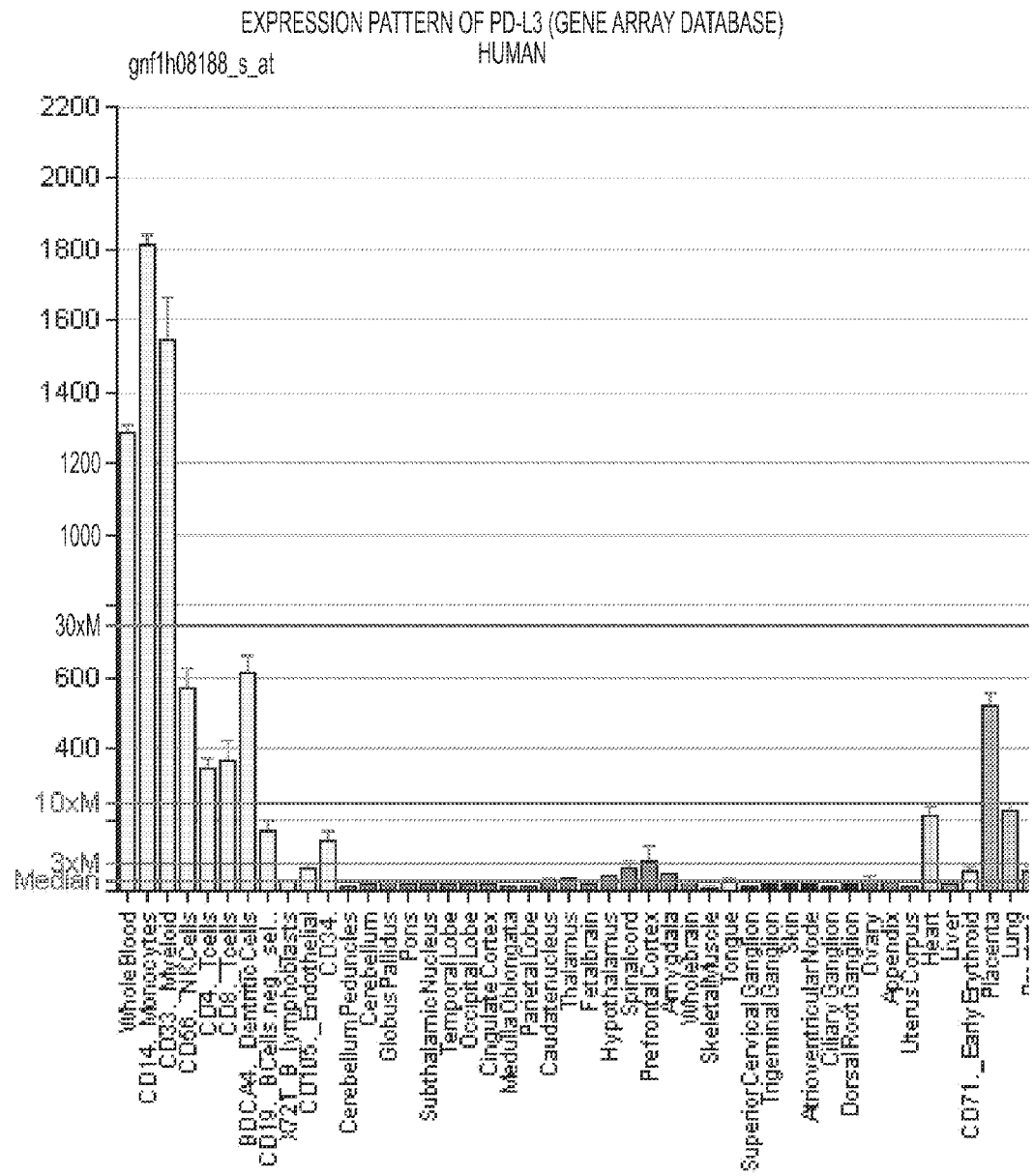

A differential expression pattern is shown on the same lineage of cells from different lymphoid organs (FIG. 3G). For CD4+ T cells and CD11b intermediate monocytes, the expression level follows the pattern of mesenteric lymph node>peripheral LN and spleen>peritoneal cavity and blood. This pattern is less pronounced for CD11bhi cells. This data suggests that PD-L3 expression on certain cell types might be regulated by cell maturity and/or tissue microenvironment.

In addition to freshly isolated cells, PD-L3 expression was analyzed on splenic CD4+ T cells, CD11bhi monocytes and CD11c+ DCs upon in vitro culture with and without activation (FIG. 6). Spleen cells were either cultured with medium, or with anti-CD3 (for activating T cells), or with IFN and LPS (for activating monocytes and DCs) for 24 hrs before being analyzed for the expression of PD-L3 and other B7 family ligands (e.g. PD-L1, PD-L2, B7-H3 and B7-H4). This comparison revealed distinctive expression patterns between these molecules. PD-L3 expression is quickly lost on all cell types upon in vitro culture, regardless of the activation status. In contrast, PD-L1 expression is upregulated on CD4+ T cells upon stimulation, or on CD11bhi monocytes and CD11c+ DCs upon culture in medium alone, and further enhanced in the face of stimulation. The expression of PD-L2, B7-H3 and B7-H4 are not prominent under the culture conditions used. The loss of PD-L3 expression in vitro is unique when compared to other B7 family ligands, but might reflect non-optimal culture conditions that fail to mimic the tissue microenvironment.

Figure 7A:
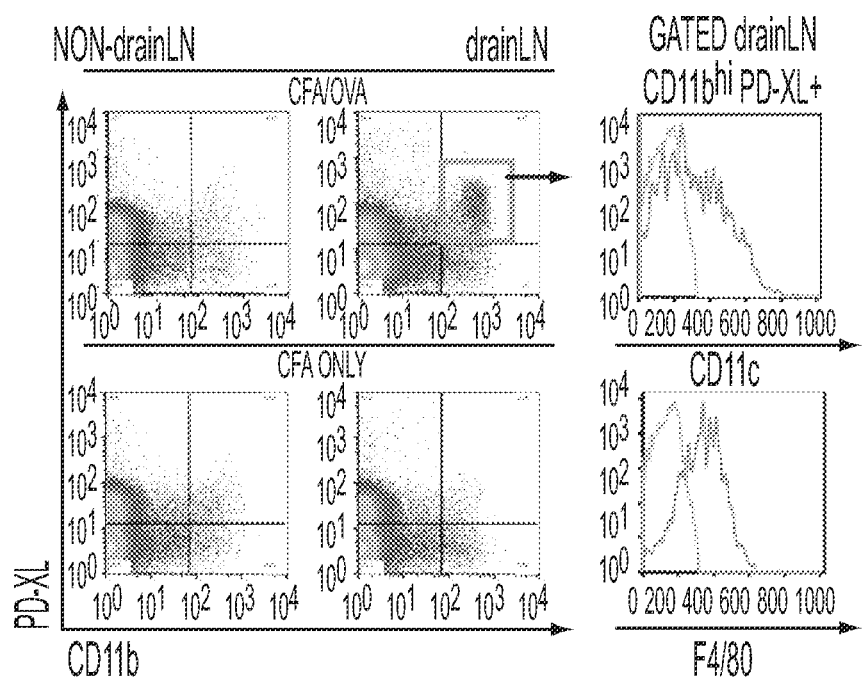
Figure 7B:
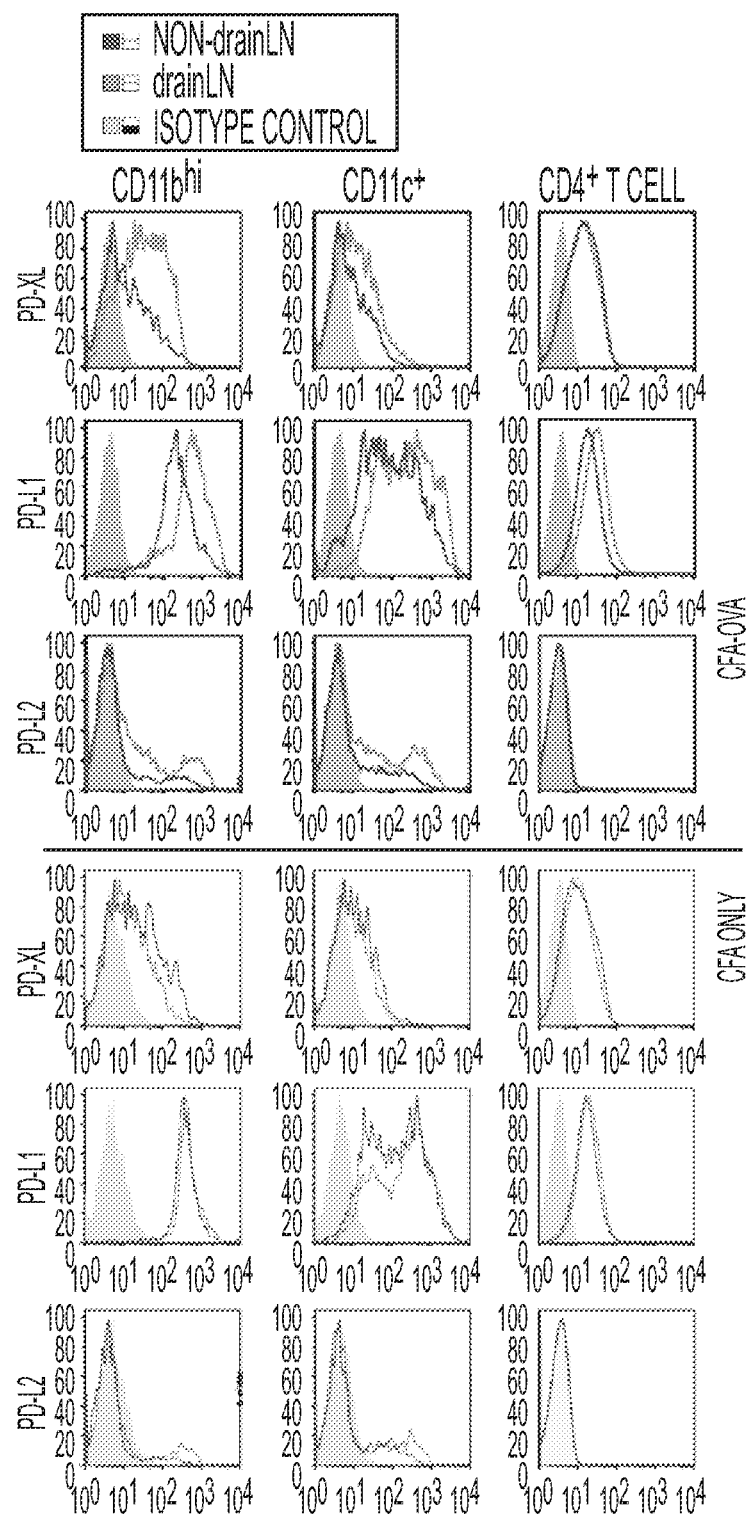

To address how PD-L3 expression might be regulated in vivo, CD4 TCR transgenic mice DO11.10 were immunized with the cognate antigen chicken ovalbumin (OVA) emulsified in complete Freund's adjuvant (CFA). At 24 hrs after immunization, cells from the draining lymph node were analyzed for PD-L3 expression (FIG. 7A). Immunization with antigen (CFA/OVA) but not the adjuvant alone drastically increased the CD11b+ PD-L3+ myeloid cell population, which contained a mixed population of F4/80+ macrophages and CD11c+ DCs. Further comparison with PD-L1 and PD-L2 reveals that even though PD-L1 has the highest constitutive expression level, PD-L3 is the most highly upregulated during such an inflammatory immune response (FIG. 7B). Collectively, these data strongly suggest that the expression of PD-L3 on myeloid APCs is tightly regulated by the immune system, which might contribute to its role in controlling immune responses and regulating T cell immunity.

In contrast to its increased expression on APCs, PD-L3 expression is diminished on activated DO11.10 CD4+ T cells at a later time point upon immunization (i.e. at 48 hr but not at 24 hr) (FIG. 8). This result suggests that PD-L3 expression on CD4 T cells in vivo may be regulated by its activation status and cytokine microenvironment during an active immune response.

Example 3

Functional Impact of PD-L3 Signaling on CD4+ and CD8+ T Cell Responses

Figure 9A:
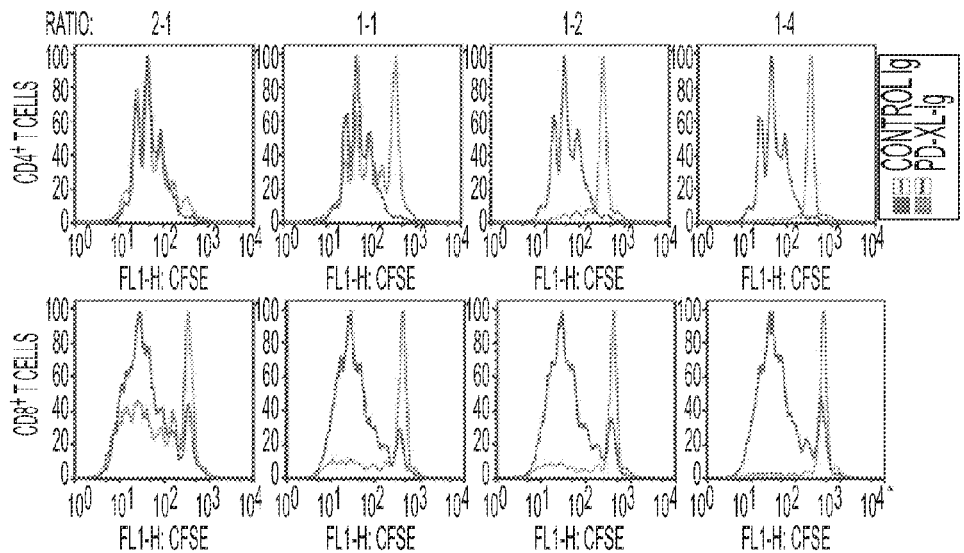
Figure 9B:
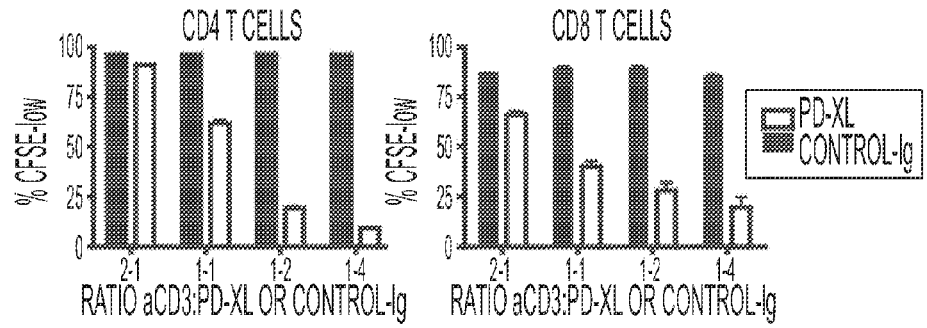
Figure 9C:
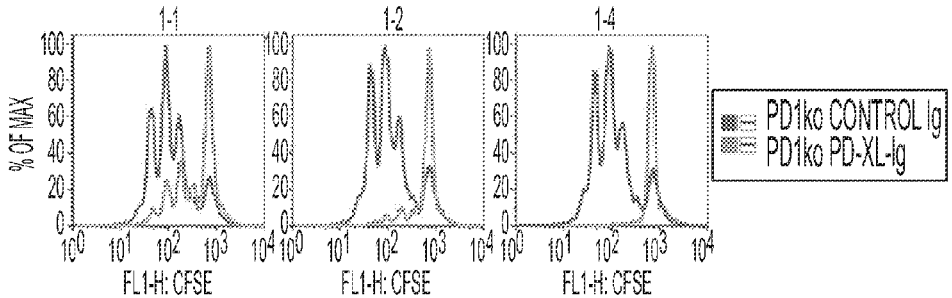

A PD-L3-Ig fusion proteins were was produced to examine the regulatory roles of PD-L3 on CD4+ T cell responses. The PD-L3-Ig fusion protein contains the extracellular domain of PD-L3 fused to the human IgG1 Fc region. When immobilized on the microplate, PD-L3-Ig but not control Ig suppressed the proliferation of bulk purified CD4+ and CD8+ T cells in response to plate-bound anti-CD3 stimulation, as determined by arrested cell division (FIG. 9A-B). The PD-L3 1 g fusion protein did not affect the absorption of anti-CD3 antibody to the plastic wells, as determined by ELISA (data not shown), thus excluding the possibility of non-specific inhibitory effects. PD-1 KO CD4+ T cells were also suppressed (FIG. 9C), indicating that PD-1 is not the receptor for PD-L3. The inhibitory effect of PD-L1-Ig and PD-L3-Ig was also directly compared (FIG. 10). When titrated amounts of Ig fusion proteins were absorbed to the microplates together with CD3 to stimulate CD4+ T cells, PD-L3-Ig showed similar inhibitory efficacy as PD-L1-Ig fusion protein.

Since bulk purified CD4+ T cells contain various subsets, the impact of PD-L3-Ig on sorted naïve (CD25-CD44lowCD62Lhi) and memory (CD25-CD44hiCD62Llow) CD4+ T cell subsets was evaluated (FIG. 11). It is shown that PD-L3 can suppress the proliferation of both subsets, albeit with much less efficacy on the memory cells.

Figure 12B:
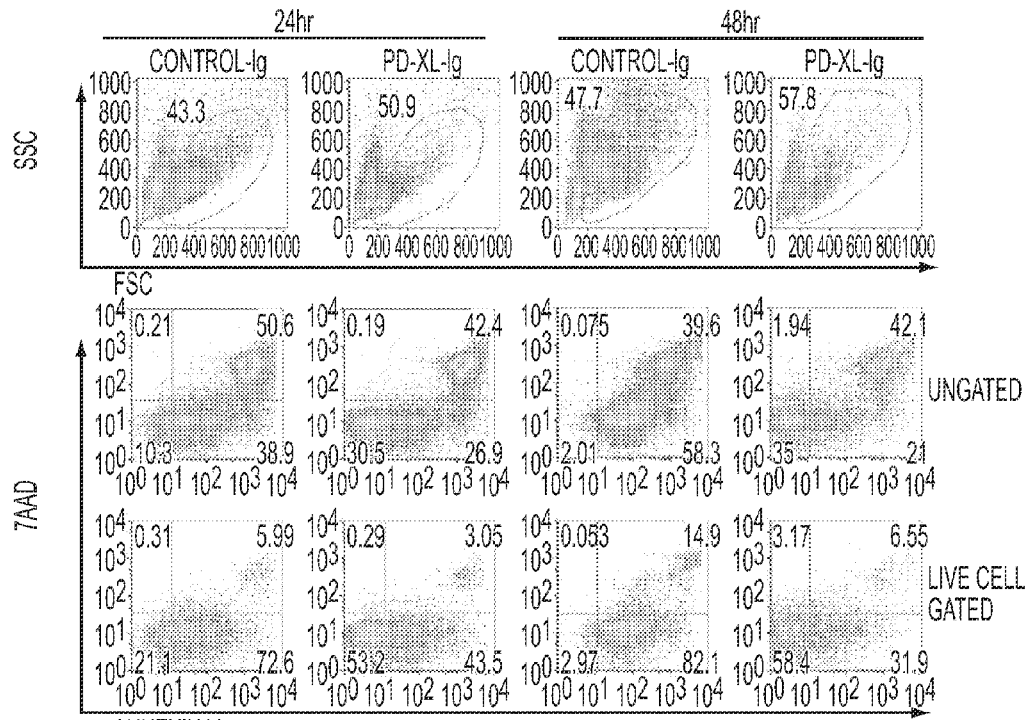

To further understand the mechanism of PD-L3-mediated suppression, the expression of early TCR activation markers and apoptosis were measured following T cell activation in the presence or absence of PD-L3-Ig. Consistent with the negative impact on cell proliferation, there is a global suppression on the expression of the early activation markers CD69, CD44, and CD62L (supplemental FIG. 12A). On the other hand, the PD-L3-Ig fusion protein did not induce apoptosis. On the contrary, less apoptosis (as determined by the percentage of annexin V+7AAD-cells) was seen in the presence of PD-L3-Ig than the control-Ig, at both early (24 hr) and later stage (48 hr) of TCR activation (FIG. 12B). For example, at 24 hr time point, on total "ungated" population, ~27% cells were apoptotic in the presence of PD-L3-Ig, but ~39% control cells were apoptotic When examining the cells within the live cell R1 gate, it is apparent that PD-L3-Ig strongly inhibited activation-induced-cell-death (ACID), because about 72.6% control cells became apoptotic whereas only 43.5% cells were apoptotic when treated with PD-L3-Ig. Similar results were seen for the 48 hr time point. Therefore, it appears that PD-L3 negatively regulates CD4+ T cell responses by suppressing early TCR activation and arresting cell division, but with minimum direct impact on apoptosis. This mechanism of suppression is similar to that of B7-H4 Sica, G. L., Choi, I. H., Zhu, G., Tamada, K., Wang, S. D., Tamura, H., Chapoval, A. I., Flies, D. B., Bajorath, J., and Chen, L. (2003). B7-H4, a molecule of the B7 family, negatively regulates T cell immunity. Immunity 18, 849-861.

Figure 9D:
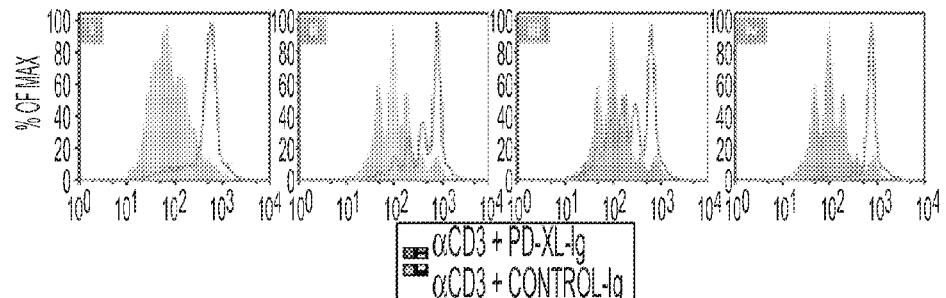

A 2-step assay was developed to determine whether PD-L3-Ig can suppress pre-activated CD4 T cells, and how persistent its suppressive effect is. It is shown that the suppressive effect of PD-L3-Ig fusion protein persists after its removal at 24 hr post activation (FIG. 9D ii). In addition, both naïve and pre-activated CD4+ T cells could be suppressed by PD-L3-Ig (FIG. 9Di, 9-Diii and 9-Div).

Figure 13A:
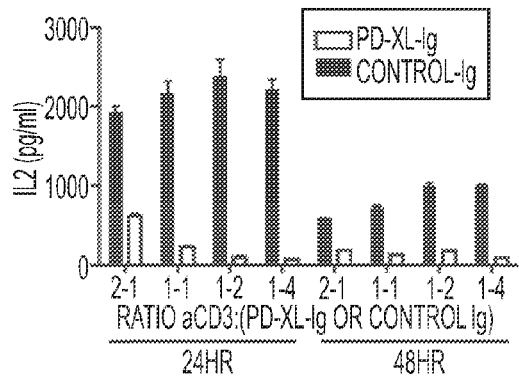
Figure 13B:
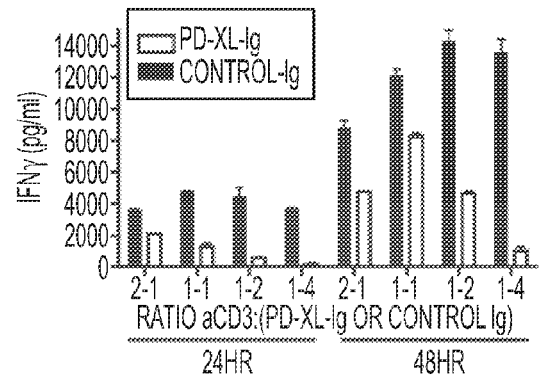
Figure 13C:
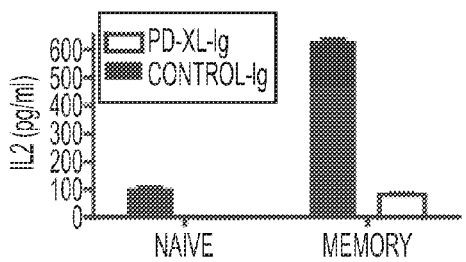
Figure 13D:
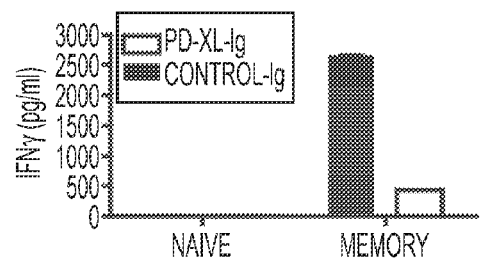
Figure 13E:
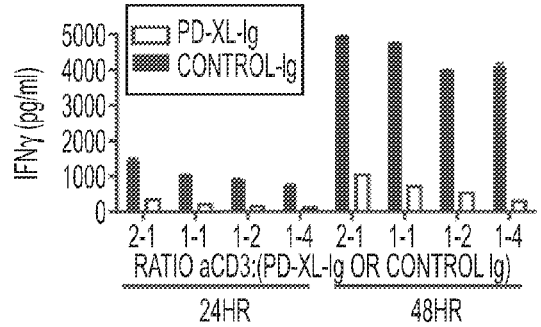

Next, the impact of PD-L3-Ig on CD4+ T cell cytokine production was analyzed. PD-L3-Ig suppressed the production of Th1 cytokines IL-2 and IFN from bulk purified CD4+ T cell culture (FIG. 13A-B). The impact of PD-L3 was further tested on separate naïve (CD25-CD44lowCD62Lhi) and memory (CD25-CD44hiCD62Llow) CD4+ T cell populations. It is shown that memory CD4+ T cells are the major source for cytokine production within the CD4+ T cell compartment, and PD-L3 can suppress this production (FIG. 13C-D). Similar inhibitory effect of PD-L3 on IFN production from CD8+ T cells was also shown (FIG. 13E). This inhibitory effect of PD-L3 on cytokine production by CD4+ and CD8+ T cells is consistent with the hypothesis that PD-L3 is an inhibitory ligand that down-regulates immune responses.

Next, studies were designed to determine the factors that are able to overcome the inhibitory effect of PD-L3. Given that PD-L3 suppressed IL-2 production, and IL-2 is critical for T cell survival and proliferation, we hypothesize that IL-2 might circumvent the inhibitory activity of PD-L3. As shown in FIG. 14A, exogenous IL-2, but not IL-15, IL-7, or IL-23, partially reversed the suppressive effect of PD-L3-Ig on cell proliferation. The incomplete rescue by high levels of IL-2 indicates that PD-L3 signaling targets broader T cell activation pathways than simply IL-2 production. On the other hand, potent co-stimulation signal provided by anti-CD28 agonistic antibody completely reversed PD-L3-Ig mediated suppression (FIG. 14B), whereas intermediate levels of costimulation is still suppressed by PD-L3 signaling (FIG. 14C). This result suggests that PD-L3-mediated immune suppression would be more effective under less inflammatory conditions, but will be inevitably overwhelmed by strong positive costimulatory signals. In this regard, PD-L3 shares this feature with other suppressive B7 family ligands such as PD-L1 and B7-H4 Sica et al., (2003), Immunity 18, 849-861; Carter et al., (2002), Eur J Immunol 32, 634-643.

In addition to PD-L3-Ig fusion protein, it is necessary to confirm that PD-L3 expressed on APCs can suppress antigen-specific T cell activation during cognate interactions between APCs and T cells. For this purpose, PD-L3-RFP or RFP control protein was over-expressed via retroviral transduction in an artificial antigen presenting cell line (CHO-APC) that stably expresses MHCII and B7-2 molecules Latchman et al., (2001), Nat Immunol 2, 261-268. One problem in expressing PD-L3 in CHO is that the majority of PD-L3 failed to localize to the cell surface, perhaps due to the alien environment that lacks support for PD-L3 surface localization (data not shown). Although there are no clear motifs present on the cytoplasmic tail of PD-L3 to suggest the mode of regulation, we speculate that the tail might play a role for its intracellular localization. Consequently, a tail-less PD-L3 mutant was designed and was found to successfully localize to CHO cell surface (data not shown).

To stimulate T cell response, CHO-PD-L3 or CHO-RFP cells were incubated together with DO11.10 CD4+ T cells in the presence of antigenic OVA peptide. As shown in FIG. 15 (A-C), CHO-PD-L3 induced less proliferation of DO11.10 cells than CHO-RFP cells. This suppressive effect is more pronounced at lower peptide concentrations, consistent with the notion that a stronger stimulatory signal would overcome the suppressive impact of PD-L3.

Figure 15A:
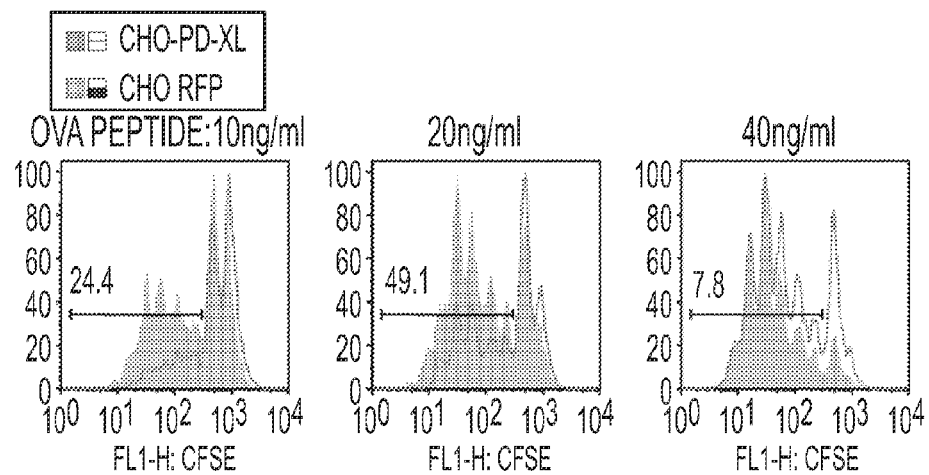
Figure 15B:
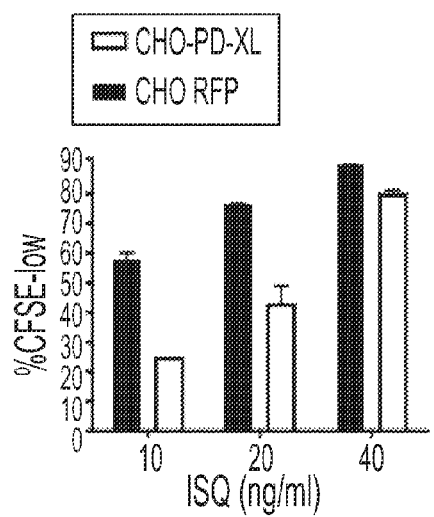
Figure 15C:
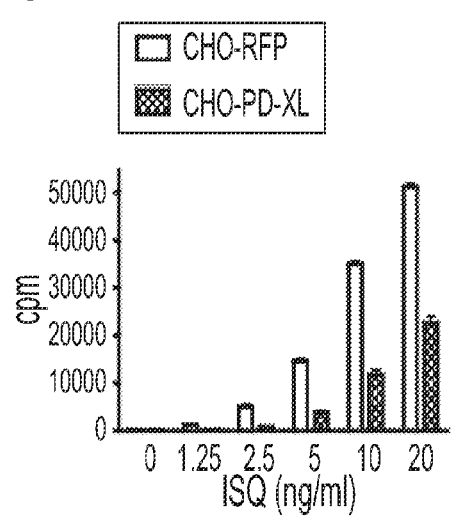
Figure 15D:
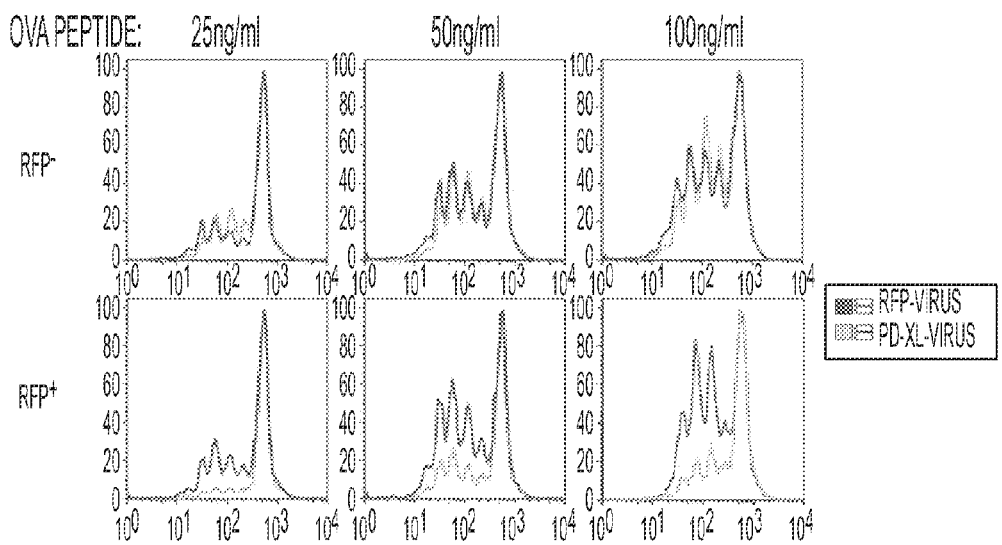

In addition, the inhibitory effect of full-length PD-L3 on natural APCs was confirmed. In vitro cultured bone marrow derived dendritic cells (BMDC) do not express high level of PD-L3 (FIG. 16). PD-L3-RFP or RFP was expressed in BMDCs by retroviral transduction during the 10 day culture period. Transduced cells were sorted to homogeneity based on RFP expression. The expression level of PD-L3 on transduced DCs was estimated by staining with anti-PD-L3 mab, and found to be similar to the level on freshly isolated peritoneal macrophages, thus within the physiological expression range (FIG. 16). Sorted BMDCs were then used to stimulate OVA-specific transgenic CD4+ T cells (OTII) in the presence of OVA peptide (FIG. 15D). It is shown therein that the expression of PD-L3 on BMDCs suppressed the cognate CD4+ T cell proliferative responses. This result is consistent with previous data using PD-L3-Ig fusion protein and CHO-APC cells, suggesting that PD-L3 can suppress T cell-mediated immune responses.

Example 4

Evaluation of Anti-PD-L3 Antibodies in Multiple Sclerosis Animal Model (EAE)

Because the PD-L3 mAbs in vivo appeared to suppress T cell responses, PD-L3 was tested to evaluate if it can inhibit a T cell-mediated autoimmune disease. Using the Experimental Allergic Encephalomyelitis (EAE) model, the functional impact of PDL-L3 mAbs on inflammatory diseases was determined. EAE is a widely used murine model of the human autoimmune disease multiple sclerosis. EAE can be induced by either immunization with myelin antigens in adjuvant or by adoptive transfer of myelin-specific T cells, which results in inflammatory infiltrates of various effector T cells and B cells, and macrophages, and demyelination of central nervous systems.

αPDL-L3 mAb was tested in the passive EAE model to avoid induction of anaphylaxis due to the injection of large amount of mAb as foreign antigen. In this adoptive transfer EAE model, donor SJL mice were immunized with CFA and PLP peptide. On day 10, total lymphocytes from draining LN were isolated, and cultured in vitro with PLP peptide, IL-23 (20 ng/ml) and anti-IFNg (10 μg/ml) for 4 days. Expanded CD4 T cells were then purified and adoptively transferred into naïve recipient mice. This analysis indicated that αPDL-L3 mAb delayed disease onset, as well as reduced disease severity, thereby shifting the disease progression curve significantly (FIG. 17). In addition, it reduced severity in a large percentage of the mice and greatly increased survival from around 22% to over 75%. This demonstrated activity of αPDL-L3 mAb in EAE is consistent with the in vitro data, and demonstrates the use of this reagent as a novel immunoregulatory reagent in various inflammatory diseases.

Example 5

PD-L3 Transgenic and Knock-Out Mice

Using Lentiviral infection of embryos, four transgenic mice ubiquitously expressing PD-L3 have been produced. These mice express full-length PD-L3 under the control of the human elongation factor 1 promoter. These mice were generated using lentiviral vector pWPT. Similar to other PD-L1 family members (Appay, et al. (2002) *J. Immunol.* 168:5954-8), it is contemplated that PD-L3 will function as a negative regulator in vivo while functioning to co-stimulate αCD3 T cell proliferation in vitro. In this respect, these mice are expected to spontaneously develop autoimmunity and in vivo immune responses in the PD-L3 transgenic mice (i.e., humoral immune responses, T cell priming, etc.) are evaluated to assess systemic autoimmune disease development.

For knock-out mice, PD-L3 is inactivated by homologous recombination. A BAC clone containing full-length PD-L3 sequence was purchased from INVITROGEN™ (Carlsbad, Calif.). A PD-L3 targeting vector was generated by inserting a 1.6 kb fragment located at the 5' side of the second exon of PD-L3 gene upstream the neomycin gene and the 5 kb fragment located at the 3' side of the third exon of PD-L3 gene downstream the neomycin gene. B6-derived embryonic stem (ES) cells are electroporated with PD-L3 targeting vector and recombined clones are selected. Selected clones are then injected into C57BL/6 blastocysts and the resulting chimeric male offspring are mated to FLP-deleter mice to remove the neomycin cassette. Transmission of the targeted allele in the offspring is determined by PCR from genomic DNA. The second and the third exon contain the PD-L3 domain, therefore, the resulting mice have only the inactivated form of the PD-L3 molecule.

The overall immune capacity of PD-L3 deficient mice is determined as with other PD-L-/- mice, including assessment of T cell responses to antigen, humoral immune responses, overt autoimmunity (e.g., Systemic Lupus Erythematosus, inflammatory bowel disease), and increased susceptibility to induced autoimmune disease (experimental autoimmune encephalomyelitis) (Chen (2004) supra).

Example 6

Cloning and Characterization of $T^{reg}$-sTNF

As indicated herein, $T^{reg}$-sTNF was identified by global transcriptional profiling of resting $T^{reg}$, $T^{reg}$ activated with αCD3, and $T^{reg}$ activated with αCD3/αGITR. $T^{reg}$-sTNF contains a TNF-like domain similar to those found in C1q family of proteins. Sequence analysis revealed that $T^{reg}$-sTNF corresponded with mouse locus Ricken ID 1110035L05 with an mRNA coding sequence given as GEN-BANK accession number NM_026125 and protein sequence give as NP_080401. The nucleic acid sequence encoding mouse $T^{reg}$-sTNF is set forth herein as SEQ ID NO:6 and the mouse $T^{reg}$-sTNF protein sequence is set forth herein as SEQ ID NO:7. This TNF-like molecule is located on chromosome 4 (154.1 Mb), near OX40 and GITR, and composed of 8 exons, creating a transcript 1301 bases in length coding for a 308 residue soluble protein. Pfam and Interpro protein predict a signal sequence (positions 1-19), a proline rich collagen triple helix-like motif (positions 99-111), and a TNF-like motif (positions 176-306). Collectively, these motifs are similar to those of the C1q family of proteins, although this TNF-like protein does not contain the characteristic C1q-like motif that identifies this family. The human homolog of $T^{reg}$-sTNF is located on chromosome 1 (1.1 Mb) and is composed of 7 exons thereby generating a transcript of 1014 bases in length coding for a 337 residue protein. The human coding sequence for the human homolog of $T^{reg}$-sTNF is provided as GENBANK accession number BC089443 and protein sequence give as AAH89443.1. The nucleic acid sequence encoding human $T^{reg}$-sTNF is set forth herein as SEQ ID NO:8 and the human $T^{reg}$-sTNF protein sequence is set forth as SEQ ID NO:9. Mouse and human genes share 65.3% homology and 66% identify at the protein level. Homologs were also identified in *Rattus norvegicus* on chromosome 5 (172.8 Mb; GENBANK accession number XM_233720.2), as well as *Fugu rubripes* and *Danio rerio*. In particular embodiments, $T^{reg}$-sTNF proteins of the present share the common amino acid sequence set forth in SEQ ID NO:10. In summary, this invention has identified PD-L3 as a novel immune-suppressive ligand that belongs to the B7 family. Similar to its family members such as PD-L1, PD-L2, and B7-H4, expression of PD-L3 on antigen presenting cells suppresses T cell immunity by engaging with a counter-receptor on T cells. Compounds which bind or modulate the activity of this novel B7 family member are useful in the treatment of immune-related diseases such as autoimmunity and cancer. In addition, therapeutic intervention of PD-L3 inhibitory pathway represents a novel approach for modulating immune responses in the field of immunotherapy.

Example 7

PD-L3 Specific Antibodies Tested in Collagen-Induced Arthritis Animal Model As shown in the experiments in FIG. 18, male DBA/1J mice were immunized at the base of their tail with 100 μl of emulsion containing 100 μg chick type-II collagen (C-II) in CFA (*mycobacterium tuberculosis* 3.5 mg/ml) and boosted IP with 100 μg aqueous C-II on day 21 post-immunization. Mice of each treatment group (n=6) were either untreated (NT-black circles), injected with 300 μg hamster IgG (Ham Ig-black squares) or injected with 300 μg of monoclonal-antibody "7c9" (red triangle) or "13F3" (green triangle), as indicated. Injections were given every 2 days. Arthritic swelling was scored on a scale of 0-4 for each paw of each mouse on the days indicated. The arthritis score shown is the total score of all paws of mice in each treatment group divided by the number of mice in the group.

This data reveals that anti-PD-L3 antibodies are effective in reducing the symptoms of arthritis in mice with collagen-induced arthritis which is an accepted animal model for evaluation of putative therapeutic agents for treating arthritis. These results provide further evidence that antibodies against PD-L3 and PD-L3 proteins and modulators may be used to treat inflammatory diseases and inflammatory autoimmune diseases such as rheumatoid arthritis, multiple sclerosis and other arthritic and inflammatory conditions.

Having described the invention the following claims are provided. These claims are intended to cover all generic and specific features described herein, and all statements of the scope which, as a matter of language, might be said to fall there between.

What is claimed is:

1. An anti-PD-L3 antibody containing a human constant domain or a human or humanized antibody fragment that binds human PD-L3 which potentially is suitable for use as a human therapeutic or immune modulatory agent that exhibits one or both of the following properties:
   (i) inhibits (1) PD-L3 mediated suppression of T cell activation or differentiation; or
   (ii) suppresses PD-L3 mediated inhibition of CD4+ or CD8+ T cell proliferation.

2. The antibody or antibody fragment of claim 1, which is monoclonal.

3. The antibody or antibody fragment of claim 1, which is human, humanized, or chimeric.

4. The antibody or antibody fragment of claim 1, which is produced by phage display.

5. The antibody or antibody fragment of claim 1, which is selected from a Fab fragment, a monovalent antibody fragment consisting of the VL, VH, CL and CH1 domains; a F(ab')2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; (v) a dAb fragment which consists of a VH domain; a scFv and a diabody.

6. A pharmaceutical composition comprising an anti-PD-L1 antibody according to claim 1.

7. The antibody or antibody fragment of claim 1, that (i) inhibits (1) PD-L3 mediated suppression of T cell activation or differentiation.

8. The antibody or antibody fragment of claim 1, that (ii) suppresses PD-L3 mediated inhibition of CD4+ or CD8+ T cell proliferation.

* * * * *